US008674084B2

United States Patent
Sainsbury et al.

(10) Patent No.: US 8,674,084 B2
(45) Date of Patent: Mar. 18, 2014

(54) PROTEIN EXPRESSION SYSTEM

(75) Inventors: Frank Sainsbury, Norfolk (GB); George Peter Lomonossoff, Norfolk (GB)

(73) Assignee: Plant Bioscience Limited, Norwich, Norfolk (GB)

( * ) Notice: Subject to any disclaimer, the term of this patent is extended or adjusted under 35 U.S.C. 154(b) by 72 days.

(21) Appl. No.: 12/812,165

(22) PCT Filed: Jan. 8, 2009

(86) PCT No.: PCT/GB2009/000060
§ 371 (c)(1),
(2), (4) Date: Jul. 8, 2010

(87) PCT Pub. No.: WO2009/087391
PCT Pub. Date: Jul. 16, 2009

(65) Prior Publication Data
US 2010/0287670 A1    Nov. 11, 2010

(30) Foreign Application Priority Data
Jan. 8, 2008    (GB) .................................. 0800272.7

(51) Int. Cl.
*C12N 15/83*    (2006.01)
*C12N 15/33*    (2006.01)
*C12N 15/113*    (2010.01)
*A01H 5/00*    (2006.01)

(52) U.S. Cl.
USPC ....... 536/23.72; 536/24.1; 435/440; 435/468; 435/320.1; 435/419; 800/278; 800/288

(58) Field of Classification Search
None
See application file for complete search history.

(56) References Cited

FOREIGN PATENT DOCUMENTS

| WO | 01/96569 | 12/2001 |
|---|---|---|
| WO | 2007/135480 | 11/2007 |
| WO | 2009/087391 | 7/2009 |

OTHER PUBLICATIONS

Sainsbury et al. (2008) Plant Phys. 148: 1212-1218.*
Pouwels et al. (2003) J. Gen. Virol. 84: 3485-3494.*
Welllink et al. (1993) Biochemie 75: 741-747.*
GenBank Accession No. X00729 (1983).*
MacFarlane et al. (2000) Virology 267: 29-35.*
Gleave (1992) Plant Molec. Biol. 20: 1203-1207.*
Canizares, M.C. et al., "A bipartite system for the constitutive and inducible expression of high levels of foreign proteins in plants," Plant Biotech. J. (2006) 4(2):183-193.
Dinesh-Kumar, S.P. et al., "Control of start codon choice on a plant viral RNA encoding overlapping genes," Plant Cell (1993) 5(6):679-692.
Holness, C.L. et al., "Identification of the initiation codons for translation of cowpea mosaic virus middle component RNA using site-directed mutagenesis of an infectious cDNA clone," Virology (1989) 172(1):311-320.
Kozak, M., "Pushing the limits of the scanning mechanism for initiation of translation," Gene (2002) 299(1-2):1-34.
Liu, L. et al., "Cowpea mosaic virus-based systems for the production of antigens and antibodies in plants," Vaccine (2005) 23(15):1788-1792.
Matsuda, D. et al., "Expression of the two nested overlapping reading frames of turnip yellow mosaic virus RNA is enhanced by a 5' cap and by 5' and 3' viral sequences," J. Virol. (2004) 78(17):9325-9335.
Rohll, J.B. et al., "3'-terminal nucleotide sequences important for the accumulation of cowpea mosaic virus M-RNA," Virology (1993) 193(2):672-679.
Sainsbury, F. et al., "Expression and multiple proteins using full-length and deleted versions of cowpea mosaic virus RNA-2," Plant Biotech. J. (2008) 6(1):82-92.
Sainsbury, F. et al., "Extremely high-level and rapid transient protein production in plants without the use of viral replication," Plant Physiol. (2008) 148(3):1212-1218.
Weiland, J.J. et al., "Infectious TYMV RNA from cloned cDNA: effects in-vitro and in vivo of point substitutions in the initiation codons of two extensively overlapping ORFs," Nucl. Acids Res. (1989) 17(12):4675-4688.
Wellink, J. et al., "Mutational analysis of AUG codons of cowpea mosaic virus M RNA," Biochimie (1993) 75 (8):741-747.
International Search Report and Written Opinion for Application No. PCT/GB2009/000060 dated May 7, 2009 (13 pages).

* cited by examiner

*Primary Examiner* — David T Fox
*Assistant Examiner* — Steven Bernacki
(74) *Attorney, Agent, or Firm* — Michael Best & Friedrich LLP

(57) ABSTRACT

The inventions is based on an expression enhancer sequence derived from the RNA-2 genome segment of a bipartite RNA virus, in which a target initiation site in the RNA-2 genome segment has been mutated. Deletion of appropriate start codons upstream of the main RNA2 translation initiation can greatly increase in foreign protein accumulation without the need for viral replication. Also provided are methods, vectors and systems, including the 'hyper-translatable' Cowpea Mosaic Virus ('CPMV-HT') based protein expression system.

25 Claims, 12 Drawing Sheets

FIGURE 14
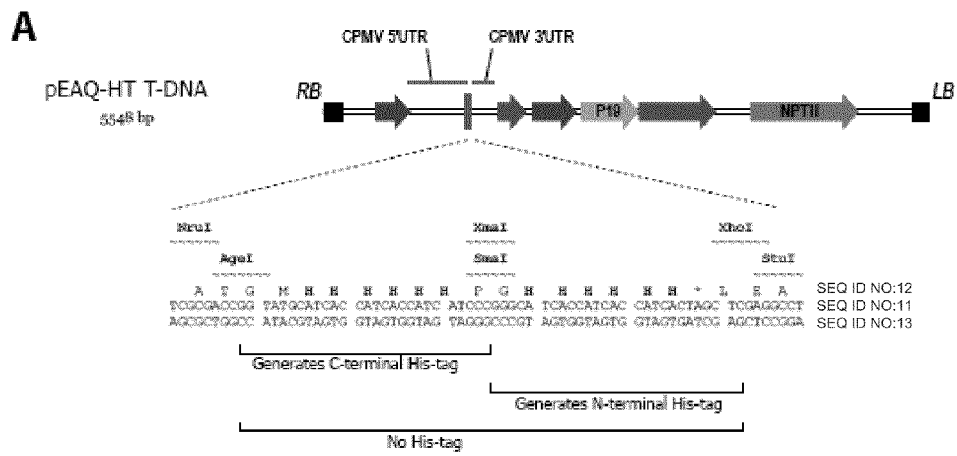
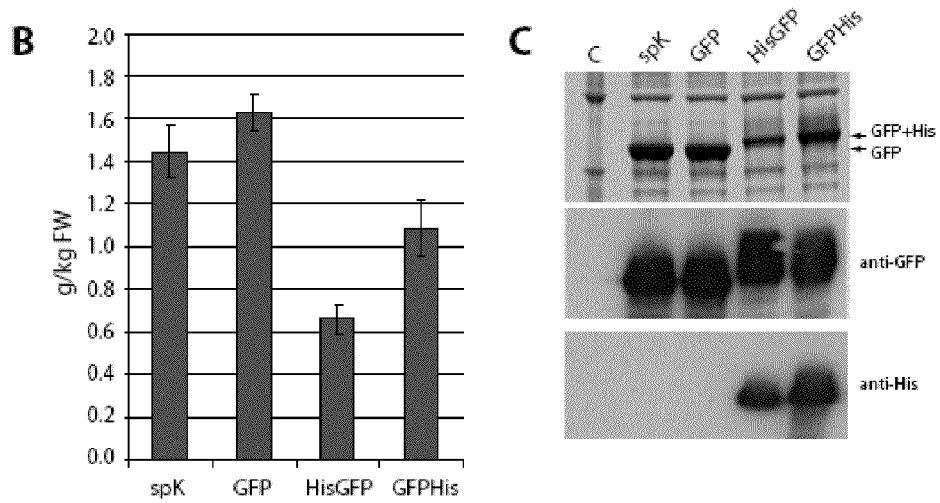
FIGURE 15

PROTEIN EXPRESSION SYSTEM

CROSS-REFERENCE TO RELATED APPLICATIONS

This patent application is a national stage filing under 35 U.S.C. 371 of International Application No. PCT/GB2009/000060, filed on Jan. 8, 2009, which claims foreign priority benefits to United Kingdom Patent Application No. 0800272.7, filed on Jan. 8, 2008. These applications are incorporated herein by reference in their entireties.

FIELD OF THE INVENTION

The present invention relates generally to methods and materials, and particularly viral derived sequences, for boosting gene expression in plants and other eukaryotic cells, for example of heterologous genes encoding proteins of interest.

BACKGROUND OF THE INVENTION

Comoviruses (CPMV)

Comoviruses are RNA viruses with a bipartite genome. The segments of the comoviral RNA genome are referred to as RNA-1 and RNA-2. RNA-1 encodes the VPg, replicase and protease proteins (Lomonossoff & Shanks, 1983). The replicase is required by the virus for replication of the viral genome. The RNA-2 of the comovirus cowpea mosaic virus (CPMV) encodes a 58K and a 48K protein, as well as two viral coat proteins L and S.

Initiation of translation of the RNA-2 of all comoviruses occurs at two different initiation sites located in the same triplet reading frame, resulting in the synthesis of two carboxy coterminal proteins. This double initiation phenomenon occurs as a result of 'leaky scanning' by the ribosomes during translation.

The 5' terminal start codons (AUGs) in RNA-2 of CPMV occur at positions 115, 161, 512 and 524. The start codons at positions 161 and 512 are in the same triplet reading frame. Initiation at the start codon at position 161 results in the synthesis of a 105K polyprotein while initiation at the start codon at position 512 directs the synthesis of a 95K polyprotein. As the synthesis of both polyproteins is terminated at the same stop codon at position 3299, the 105K and the 95K proteins are carboxy coterminal. The AUG codon at position 524 can serve as an initiator if the AUG at 512 is deleted. However, in the presence of the AUG 512 it does not serve this function and simply codes for the amino acid methionine (Holness et al., 1989; Wellink et al., 1993). The start codon at position 115 is not essential for virus replication (Wellink at al., 1993).

The 105K and 95K proteins encoded by CPMV RNA-2 genome segment are primary translation products which are subsequently cleaved by the RNA1-encoded proteolytic activity to yield either the 58K or the 48K protein, depending on whether it is the 105K or 95K polyprotein that is being processed, and the two viral coat proteins, L and S. Initiation of translation at the start codon at position 512 in CPMV is more efficient than initiation at position 161, resulting in the production of more 95K polyprotein than 105K polyprotein.

The start codon at position 115 in CPMV RNA-2 lies upstream of the initiation sites at positions 161 and 512 and is in a different reading frame. As this start codon is in-phase with a stop codon at position 175, initiation at this site could result in the production of a 20 amino acid peptide. However, production of such a peptide has not been detected to date.

Necessity of Maintaining the Frame between AUGs

Mutagenesis experiments have shown that maintenance of the frame between the initiation sites at positions 161 and 512 in CPMV RNA-2 is essential for efficient replication of RNA-2 by the RNA-1-encoded replicase (Holness et al., 1989; van Bokhoven et al., 1993; Rohll et al., 1993; Wellink et al., 1993). This requirement restricts the length of sequences which can be inserted upstream of the 512 start codon in expression vectors based on CPMV RNA-2 (see below), making the cloning of foreign genes into such vectors more difficult than would be ideal. For example it precludes the use of polylinkers as their use will often alter the open reading frame (ORF) between these initiation sites.

CPMV Vectors

CPMV has served as the basis for the development of vector systems suitable for the production of heterologous polypeptides in plants (Liu et al., 2005; Sainsbury et al., 2007). These systems are based on the modification of RNA-2 but differ in whether full-length or deleted versions are used. In both cases, however, replication of the modified RNA-2 is achieved by co-inoculation with RNA-1. Expression systems based on a full-length version of RNA-2 involve the fusion of the foreign protein to the C-terminus of the RNA-2-derived polyproteins. Release of the N-terminal polypeptide is mediated by the action of the 2A catalytic peptide sequence from foot-and-mouth-disease virus (Gopinath et al., 2000). The resulting RNA-2 molecules are capable of spreading both within and between plants. This strategy has been used to express a number of recombinant proteins, such as the Hepatitis B core antigen (HBcAg) and Small Immune Proteins (SIPs), in cowpea plants (Mechtcheriakova et al., 2006; Monger et al., 2006; Alamillo at al., 2006). Though successful, the use of a full-length viral vector has disadvantages in terms of size constraints of inserted sequences and concerns about biocontainment.

To address these, a system based on a deleted version of CPMV RNA-2 has recently been developed (Cañizares et al., 2006). In this system the region of RNA-2 encoding the movement protein and both coat proteins has been removed. However, the deleted molecules still possess the cis-acting sequences necessary for replication by the RNA-1-encoded replicase and thus high levels of gene amplification are maintained without the concomitant possibility of the modified virus contaminating the environment. With the inclusion of a suppressor of gene silencing, such as HcPro from PVY, (Brigneti et al., 1998) in the inoculum in addition to RNA-1, the deleted CPMV vector can be used as a transient expression system (WO/2007/135480) Bipartite System, Method And Composition For The Constitutive And Inducible Expression Of High Levels Of Foreign Proteins In Plants; also Sainsbury et al., 2009). However, in contrast to the situation with a vector based on full-length RNA-2, replication is restricted to inoculated leaves. These CPMV vectors have been used to express multi-chain complexes consisting of a single type of polypeptide.

Multiple copies of vectors based on either full-length or deleted versions of CPMV RNA-2 have also been shown to be suitable for the production of heteromeric proteins in plants (Sainsbury at al., 2008). Co-infiltration of two full-length RNA-2 constructs containing different marker genes into *Nicotiana benthamiana* in the presence of RNA-1 has been used to show that two foreign proteins can be efficiently expressed within the same cell in inoculated tissue. Furthermore, the proteins can be co-localised to the same sub-cellular compartments, which is an essential prerequisite for heteromer formation.

The suitability of different CPMV RNA-2 vectors for the expression of heteromeric proteins in plants has also been investigated. Insertion of the heavy and light chains of an IgG into full-length and deleted versions of RNA-2 showed that both approaches led to the accumulation of full-size IgG molecules in the inoculated tissue but that the levels were significantly higher when deleted RNA-2 vectors were used. The ability of full-length RNA-2 constructs to spread systemically therefore seems to be irrelevant to the production of heteromeric proteins and the use of deleted versions of RNA-2 is clearly advantageous, especially as they also offer the benefit of biocontainment.

Thus, known CPMV based vector systems represent useful tools for the expression of a heterologous gene encoding a protein of interest in plants. However, there is still a need in the art for optimised vector systems which improve, for example, the yield of the heterologous proteins expressed and the ease of use of the vector.

SUMMARY OF INVENTION

The present inventors have surprisingly found that mutation of the start codon at position 161 in a CPMV RNA-2 vector strongly increases the levels of expression of a protein encoded by a gene inserted after the start codon at position 512. The levels of protein expression were increased about 20-30 fold compared with expression of the same protein from a CPMV RNA-2 vector differing only in that the start codon at position 161 was intact (Sainsbury and Lomonossoff, 2008). The present invention allows the production of high levels of foreign proteins without the need for viral replication.

The inventors have also found that mutation of the start codon at position 161 negates the need for maintaining the frame between the position of the mutated start codon at position 161 and the start codon at position 512, thus allowing insertion of sequences of any length after the mutated start codon at position 161. This is particularly advantageous as it allows polylinkers of any length to be inserted into RNA-2 vectors after the mutated start codon, which can then be used to facilitate cloning of a gene of interest into the vector.

In addition, the inventors have found that despite the increase in protein expression, plants transformed with a CPMV RNA-2 vector comprising a mutated start codon at position 161 looked healthier, i.e. showed less necrosis, than plants transformed with known CPMV RNA-2 vectors. Plant health is an important factor in the expression of proteins from plants as healthy plants survive for longer periods of time. In addition, plant health is also important in the purification of proteins from plants as tannins released as a result of necrosis can interfere with protein purification (Sainsbury and Lomonossoff, 2008).

Thus the present invention relates to improved protein production systems and methods, based on modified bipartite virus sequences.

Thus in various aspects of the invention there is provided or utilised an expression enhancer sequence, which sequence is derived from (or shares homology with) the RNA-2 genome segment of a bipartite RNA virus, such as a comovirus, in which a target initiation site has been mutated The present invention further provides processes for increasing the expression or translational enhancing activity of a sequence derived from an RNA-2 genome segment of a bipartite virus, which processes comprise mutating a target initiation site therein.

Some particular definitions and embodiments of the invention will now be described in more detail.

"Enhancer" sequences (or enhancer elements), as referred to herein, are sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

A "target initiation site" as referred to herein, is the initiation site (start codon) in a wild-type RNA-2 genome segment of a bipartite virus (e.g. a comovirus) from which the enhancer sequence in question is derived, which serves as the initiation site for the production (translation) of the longer of two carboxy coterminal proteins encoded by the wild-type RNA-2 genome segment.

As described above, production of the longer of the two carboxy coterminal proteins encoded by CPMV RNA-2, the 105K protein, is initiated at the initiation site at position 161 in the wild-type CPMV RNA-2 genome segment. Thus, the target initiation site in enhancer sequences derived from the CPMV RNA-2 genome segment is the initiation site at position 161 in the wild-type CPMV RNA-2.

Mutations around the start codon at position 161 may have the same (or similar) effect as mutating the start codon at position 161 itself, for example, disrupting the context around this start codon may mean that the start codon is by-passed more frequently.

In one aspect of the present invention, a target initiation site may therefore be 'mutated' indirectly by mutating one or more nucleotides upstream and/or downstream of the target initiation site, but retaining the wild-type target initiation site, wherein the effect of mutating these nucleotides is the same, or similar, to the effect observed when the target initiation site itself is mutated.

As target initiation sites serve as the initiation site for the production of the longer of two carboxy coterminal proteins encoded by a wild-type RNA-2 genome segment, it follows that target initiation sites are in-frame (in phase) with a second initiation site on the same wild-type RNA-2 genome segment, which serves as the initiation site for the production of the shorter of two carboxy coterminal proteins encoded by the wild-type RNA-2. Two initiation sites are in-frame if they are in the same triplet reading frame.

The target initiation site in enhancer sequences derived from the wild-type CPMV RNA-2 genome segment, i.e. the initiation site at position 161, is in frame with the initiation site at position 512, which serves as the initiation site for the production of the shorter of the two carboxy coterminal proteins encoded by CPMV RNA-2 (the 95K protein) in the wild-type CPMV RNA-2 genome segment.

Thus, a target initiation site is located upstream (5') of a second initiation site in the wild-type RNA-2 genome segment from which the enhancer sequence is derived, which serves the initiation site for the production of the shorter of two carboxy coterminal polyproteins encoded by the wild-type RNA-2 genome segment. In addition, a target initiation site may also be located downstream (3') of a third initiation site in the wild-type RNA-2 genome from which the enhancer sequence is derived. In CPMV the target initiation site, i.e. the initiation site at position 161, is located upstream of a second initiation site at position 512 which serves as the initiation site for the production of the 95K protein and downstream of a third initiation site at position 115.

A target initiation site in an enhancer sequence derived from the RNA-2 genome segment of a bipartite virus is therefore the first of two initiation sites for the production of two carboxy coterminal proteins encoded by the wild-type RNA-2. 'First' in this context refers to the initiation site located closer to the 5' end of the wild-type RNA-2 genome segment.

More than one initiation site in the sequence may be mutated, if desired. For example the 'third' initiation site at (or corresponding to) position 115 may also be deleted or altered. It has been shown that removal of AUG 115 in addition to the removal of AUG 161, further enhances expression (Sainsbury and Lomonossoff, 2008).

The enhancer sequences of the present invention are based on modified sequences from the RNA-2 genome segments of bipartite RNA viruses.

A bipartite virus, or virus with a bipartite genome, as referred to herein may be a member of the Comoviridae family. All genera of the family Comoviridae appear to encode two carboxy-coterminal proteins. The genera of the Comoviridae family include Comovirus, Nepovirus, Fabavirus, Cheravirus and Sadwavirus. Comoviruses include Cowpea mosaic virus (CPMV), Cowpea severe mosaic virus (CPSMV), Squash mosaic virus (SqMV), Red clover mottle virus (RCMV), Bean pod mottle virus (BPMV). Preferably, the bipartite virus (or comovirus) is CPMV.

The sequences of the RNA-2 genome segments of these comoviruses and several specific strains are available from the NCBI database under the accession numbers listed in brackets: cowpea mosaic virus RNA-2 (NC_003550), cowpea severe mosaic virus RNA-2 (NC_003544), squash mosaic virus RNA-2 (NC_003800), squash mosaic virus strain Kimble RNA-2 (AF059533), squash mosaic virus strain Arizona RNA-2 (AF059532), red clover mottle virus RNA-2 (NC_003738), bean pod mottle virus RNA-2 (NC_003495), bean pod mottle virus strain K-Hopkins1 RNA-2 (AF394609), bean pod mottle virus strain K-Hancock1 RNA-2 (AF394607), Andean potato mottle virus (APMoV: L16239) and Radish mosaic virus (RaMV; AB295644). There are also partial RNA-2 sequences available from bean rugose mosaic virus (BRMV; AF263548) and a tentative member of the genus Comovirus, turnip ringspot virus (EF191015). Numerous sequences from the other genera in the family Comoviridae are also available.

To date, all comoviruses which have been investigated have been shown to have two alternative start codons for the expression of two carboxy coterminal polyproteins form their RNA-2 genome segments. In particular, the RNA-2 genome segments of CPMV, CPSMV, BPMV, SqMV and RCMV are known to comprise two alternative start codons for the expression of two carboxy coterminal polyproteins.

Target initiation sites in other comoviruses, which are equivalent to the initiation site at position 161 in the wild-type RNA-2 segment of CPMV (i.e. correspond to it) can therefore be identified by methods known in the art. For example, target initiation sites can be identified by a sequence alignment between the wild-type RNA-2 genome segment sequence of CPMV and the RNA-2 genome segment sequence of another comovirus. Such sequence alignments can then be used to identify a target initiation site in the comoviral RNA-2 genome segment sequence by identifying an initiation site which, at least in the alignment, is near, or at the same position as, the target initiation site at position 161 in the wild-type CPMV RNA-2.

Target initiation sites in other comoviruses may also be identified by determining the start codon which serves as the initiation site for the synthesis of the longer of two carboxy coterminal proteins encoded by the wild-type comoviral RNA-2 genome segment. This approach can also be used in combination with an alignment as described above, i.e. this approach can be used to confirm that a comoviral initiation site identified by means of an alignment with CPMV RNA-2 is a target initiation site.

Of course, the above methods can also be used for identifying initiation sites in other comoviral RNA-2 genome segments, which are equivalent to the initiation site at position 512 in the wild-type CPMV RNA-2 genome segment. However, instead of identifying the start codon which serves as the initiation site for the synthesis of the longer of two carboxy coterminal proteins encoded by the wild-type comoviral RNA-2 genome segment, the start codon which serves as the initiation site for the synthesis of the shorter of two carboxy coterminal proteins encoded by the wild-type comoviral RNA-2 genome segment, is identified.

Once two comoviral RNA-2 initiation sites which are likely to be equivalent to the initiation sites at positions 161 and 512 in CPMV RNA-2 have been identified, the identification of the target initiation site can be confirmed by checking that the two initiation sites are in the same frame, i.e. in the same triplet reading frame, as they can only serve as initiation sites for the production of two carboxy coterminal proteins if this is the case.

In one embodiment of the invention, the enhancer sequence comprises nucleotides 1 to 512 of the CPMV RNA-2 genome segment (see Table 1), wherein the target initiation site at position 161 has been mutated. In another embodiment of the invention, the enhancer sequence comprises an equivalent sequence from another comovirus, wherein the target initiation site equivalent to the start codon at position 161 of CPMV has been mutated. The target initiation site may be mutated by substitution, deletion or insertion. Preferably, the target initiation site is mutated by a point mutation.

In alternative embodiments of the invention, the enhancer sequence comprises nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of a comoviral RNA-2 genome segment sequence with a mutated target initiation site. In other embodiments of the invention, the enhancer sequence comprises nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of the CPMV RNA-2 genome segment sequence shown in Table 1, wherein the target initiation site at position 161 in the wild-type CPMV RNA-2 genome segment has been mutated.

In further embodiments of the invention, the enhancer sequence comprises nucleotides 1 to 500, 1 to 490, 1 to 480, 1 to 470, 1 to 460, 1 to 450, 1 to 400, 1 to 350, 1 to 300, 1 to 250, 1 to 200, or 1 to 100 of a comoviral RNA-2 genome segment sequence with a mutated target initiation site.

In alternative embodiments of the invention, the enhancer sequence comprises nucleotides 1 to 500, 1 to 490, 1 to 480, 1 to 470, 1 to 460, 1 to 450, 1 to 400, 1 to 350, 1 to 300, 1 to 250, 1 to 200, or 1 to 100 of the CPMV RNA-2 genome segment sequence shown in Table 1, wherein the target initiation site at position 161 in the wild-type CPMV RNA-2 genome segment has been mutated.

Enhancer sequences comprising at least 100 or 200, at least 300, at least 350, at least 400, at least 450, at least 460, at least 470, at least 480, at least 490 or at least 500 nucleotides of a comoviral RNA-2 genome segment sequence with a mutated target initiation site are also embodiments of the invention.

In addition, enhancer sequences comprising at least 100 or 200, at least 300, at least 350, at least 400, at least 450, at least 460, at least 470, at least 480, at least 490 or at least 500 nucleotides of the CPMV RNA-2 genome segment sequence shown in Table 1, wherein the target initiation site at position 161 in the wild-type CPMV RNA-2 genome segment has been mutated, are also embodiments of the invention.

Alternative embodiments of the invention are enhancer sequences having at least 99%, 98%, 97%, 96%, 95%, 90%, 85%, 80%, 75%, 70%, 65%, 60%, 55%, or 50% identity to the CPMV RNA-2 genome segment sequence shown in Table 1, wherein the target initiation site at position 161 in the wild-type CPMV RNA-2 genome segment has been mutated.

The terms "percent similarity", "percent identity" and "percent homology" when referring to a particular sequence are used as set forth in the University of Wisconsin GCG software program. Enhancer sequences may thus specifically hybridise with the complementary sequence of the CPMV RNA-2 genome segment sequence shown in Table 1, with the proviso that the target initiation site corresponding to position 161 in the wild-type CPMV RNA-2 genome segment has been mutated.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. "Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

A target initiation site in an enhancer sequence of the invention may be mutated by deletion, insertion or substitution, such that it no longer functions as a translation initiation site. For example, a point mutation may be made at the position of the target initiation site in the enhancer sequence. Alternatively, the target initiation site in the enhancer sequence may be deleted either partially or in its entirety. For example, a deletion spanning the target initiation site in the enhancer sequence may be made. Deletions spanning the initiation site may be up to 5, up to 10, up to 15, up to 20, up to 25, up to 30, up to 35, up to 40, up to 45, or up to 50 nucleotides in length, when compared with the sequence of the wild-type RNA-2 genome segment from which the enhancer sequence is derived.

Without wishing to be bound by theory, mutation of the start codon at position 161 in CPMV is thought to lead to the inactivation of a translational suppressor, which results in enhanced initiation of translation from start codons located downstream of the inactivated translational suppressor.

Thus, the present invention further provides an enhancer sequence derived from an RNA-2 genome segment of a bipartite virus, wherein the enhancer sequence comprises an inactivated translational suppressor sequence.

The present invention further provides a process for increasing the expression or translational enhancing activity of a sequence derived from an RNA-2 genome segment of a bipartite virus, which process comprises inactivating a translational suppressor sequence therein.

As already mentioned above, mutation of the initiation site at position 161 in the CPMV RNA-2 genome segment is thought to lead to the inactivation of a translation suppressor normally present in the CPMV RNA-2.

A translational suppressor sequence, as referred to herein, is a sequence in the wild-type RNA-2 genome segment of the bipartite virus (e.g. a comovirus) from which the enhancer sequence in question is derived, which comprises, or consists of, the initiation site for the production (translation) of the longer of two carboxy coterminal proteins encoded by the wild-type RNA-2 genome segment.

Translational suppressor sequences in enhancer sequences derived from the CPMV RNA-2 genome segment, are sequences comprising, or consisting of, the target initiation site described above. Thus, translational suppressor sequences comprise, or consist of, a target initiation site as defined above, and may be inactivated by mutagenesis as described above.

The enhancer sequences defined above may be used in various aspects and embodiments of the invention as follows.

Thus in one aspect of the present invention there is provided or utilised an isolated nucleic acid consisting, or consisting essentially of, an expression enhancer sequence as described above.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" Is sometimes used. This term, when applied to DNA, refers to a DNA molecule that is separated from sequences with which it is immediately contiguous in the naturally occurring genome of the organism in which it originated.

For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The nucleic acid may thus consist or consist essentially of a portion, or fragment, of the RNA-2 genome segment of the bipartite RNA virus from which the enhancer is derived. For example, in one embodiment the nucleic acid does not comprise at least a portion of the coding region of the RNA-2 genome segment from which it is derived. The coding region may be the region of the RNA-2 genome segment encoding the shorter of two carboxy coterminal proteins. The nucleic acid may consist or consist essentially of the portion of an RNA-2 genome segment of a bipartite virus extending from the 5' end of the wild-type RNA-2 genome segment to the initiation site from which production (translation) of the shorter of two carboxy coterminal proteins encoded by the wild-type RNA-2 genome segment is initiated.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence. For example, when used in reference to a nucleic acid, the phrase includes the sequence per se and minor changes and\or extensions that would not affect the enhancer function of the sequence, or provide further (additional) functionality.

The invention further relates to gene expression systems comprising an enhancer sequence of the invention.

Thus, in another aspect the present invention provides a gene expression system comprising an enhancer sequence as described above.

The gene expression system may also comprise a gene encoding a protein of interest inserted downstream of the enhancer sequence. Inserted sequences encoding a protein of interest may be of any size.

In a further aspect the present invention therefore provides a gene expression system comprising:
(a) an enhancer sequence as described above; and (b) a gene encoding a protein of interest, wherein the gene is located downstream of the enhancer sequence.

The gene and protein of interest may be a heterologous i.e. not encoded by the wild-type bipartite RNA virus from which the enhancer sequence is derived.

Gene expression systems may be used to express a protein of interest in a host organism. In this case, the protein of interest may also be heterologous to the host organism in question i.e. introduced into the cells in question (e.g. of a plant or an ancestor thereof) using genetic engineering, i.e. by human intervention. A heterologous gene in an organism may replace an endogenous equivalent gene, i.e. one which normally performs the same or a similar function, or the inserted sequence may be additional to the endogenous gene or other sequence.

Persons skilled in the art will understand that expression of a gene of interest will require the presence of an initiation site (AUG) located upstream of the gene to be expressed. Such initiation sites may be provided either as part of an enhancer sequence or as part of a gene encoding a protein of interest.

The host organism may be a plant. However, as translational mechanisms are well conserved over eukaryotes, the gene expression systems may also be used to express a protein of interest in eukaryotic host organisms other than plants, for example in insect cells as modified baculovirus vectors, or in yeast or mammalian cells.

Gene expression systems may be operably linked to promoter and terminator sequences.

Thus, gene expression systems may further comprise a termination sequence and the gene encoding a protein of interest may be located between the enhancer sequence and the termination sequence, i.e. downstream (3') of the enhancer sequence and upstream (5') of the termination sequence.

Thus the invention further provides an expression cassette comprising:
(i) a promoter, operably linked to
(ii) an enhancer sequence as described above
(iii) a gene of interest it is desired to express
(iv) a terminator sequence.

Preferably the promoter used to drive the gene of interest will be a strong promoter. Examples of strong promoters for use in plants include
(1) p35S: Odell et al., 1985
(2) Cassava Vein Mosaic Virus promoter, pCAS, Verdaguer et al., 1996
(3) Promoter of the small subunit of ribulose biphosphate carboxylase, pRbcS: Outchkourov et al., 2003.

Other strong promoters include pUbi (for monocots and dicots) and pActin.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

The termination (terminator) sequence may be a termination sequence derived from the RNA-2 genome segment of a bipartite RNA virus, e.g. a comovirus. In one embodiment the termination sequence may be derived from the same bipartite RNA virus from which the enhancer sequence is derived. The termination sequence may comprise a stop codon. Termination sequence may also be followed by polyadenylation signals.

Gene expression cassettes, gene expression constructs and gene expression systems of the invention may also comprise an untranslated region (UTR). The UTR may be located upstream of a terminator sequence present in the gene expression cassette, gene expression construct or gene expression system. Where the gene expression cassettes, gene expression constructs or gene expression systems comprises a gene encoding a protein of interest, the UTR may be located downstream of said gene.

Thus, the UTR may be located between a gene encoding a protein of interest and a terminator sequence. The UTR may be derived from a bipartite RNA virus, e.g. from the RNA-2 genome segment of a bipartite RNA virus. The UTR may be the 3' UTR of the same RNA-2 genome segment from which the enhancer sequence present in the gene expression cassette, gene expression construct or gene expression system is derived. Preferably, the UTR is the 3' UTR of a comoviral RNA-2 genome segment, e.g. the 3' UTR of the CPMV RNA-2 genome segment.

As described above, it was previously shown to be essential for efficient replication of CPMV RNA-2 by the CPMV RNA-1-encoded replicase that the frame between the initiation sites at positions 161 and 512 in the RNA-2 was maintained, i.e. that the two initiation sites remained in the same triple reading frame (Holness of al., 1989; van Bokhoven et al., 1993; Rohll at al., 1993). This requirement limited the length of sequences which could be inserted upstream of the initiation site at position 512 in expression vectors based on CPMV. In particular, it precluded the use of polylinkers as their use often altered the open reading frame (ORF) between the two initiation sites.

The present inventors have shown that maintenance of the reading frame between the initiation sites at positions 161 and 512 in CPMV RNA-2 is also required for efficient initiation of translation at the initiation site at position 512, i.e. it is required for efficient expression of the shorter of the two carboxy coterminal proteins encoded by CPMV (the 95K protein).

However, the present inventors have also demonstrated that mutation of the initiation site at position 161 in CPMV RNA-2 allows insertion of sequences upstream of the initiation site at position 512, which alter the frame between the mutated start codon and the initiation site at position 512, without any negative effect on the level of expression of the 95K protein. Consequently, mutation of the initiation site at position 161 means that there is no longer any restriction on the length of sequences that can be inserted upstream of the initiation site at position 512.

Where maintenance of the reading frame between initiation sites coding for two carboxy-coterminal proteins is also required in other bipartite viruses, this requirement may also be overcome by mutating the AUG which serves as the initiation site for productions of the longer of the two carboxy-coterminal proteins encoded by the viral RNA-2 genome segment. Thus, in another aspect the present invention provides a gene expression construct comprising:

(a) an enhancer sequence as described above; and (b) a heterologous sequence for facilitating insertion of a gene encoding a protein of interest into the gene expression system, wherein the heterologous sequence is located downstream of the mutated target initiation site in the enhancer sequence.

The heterologous sequence may be located upstream of the start codon from which production of the shorter of two carboxy coterminal proteins is initiated in the wild-type RNA-2 genome segment from which the enhancer sequence of the gene expression system is derived. Alternatively, the heterologous sequence may be provided around the site of the start codon, or replace the start codon, from which production of the shorter of two carboxy coterminal proteins is initiated in the wild-type RNA-2 genome segment from which the enhancer sequence of the gene expression system is derived. In a gene expression system with an enhancer sequence derived from the RNA-2 of CPMV, the heterologous sequence may be provided upstream of, around the site of, or replace, the start codon which is at position 512 in the wild-type RNA-2 CPMV genome segment.

The heterologous sequence may be a polylinker or multiple cloning site, i.e. a sequence which facilitates cloning of a gene encoding a protein of interest into the expression system.

For example, as described hereinafter, the present inventors have provided constructs including a polylinker between the 5' leader and 3' UTRs of a CPMV-based expression cassette. As described below, any polylinker may optionally encode one or more sets of multiple x Histidine residues to allow the fusion of N- or C terminal His-tags to facilitate protein purification.

Preferably the expression constructs above are present in a vector, and preferably it comprises border sequences which permit the transfer and integration of the expression cassette into the organism genome.

Preferably the construct is a plant binary vector. Preferably the binary transformation vector is based on pPZP (Hajdukiewicz, et al. 1994). Other example constructs include pBin19 (see Frisch, D. A., L. W. Harris-Haller, et al. (1995). "Complete Sequence of the binary vector Bin 19." Plant Molecular Biology 27: 405-409).

As described herein, the invention may be practiced by moving an expression cassette with the requisite components into an existing pBin expression cassette, or in other embodiments a direct-cloning pBin expression vector may be utilised.

For example, as described hereinafter, the present inventors have modular binary vectors designed for (but not restricted to) use with the enhancer sequences described herein. These are based on improvements to the pBINPLUS vector whereby it has been shown that it is possible to drastically reduce the size of the vector without compromising performance in terms of replication and TDNA transfer. Furthermore, elements of the enhancer system (as exemplified by the so-called "CPMV-HT" system) have been incorporated into the resulting vector in a modular fashion such that multiple proteins can be expressed from a single T-DNA. These improvements have led to the creation of a versatile, high-level expression vector that allows efficient direct cloning of foreign genes.

These examples represent preferred binary plant vectors. Preferably they include the ColEI origin of replication, although plasmids containing other replication origins that also yield high copy numbers (such as pRi-based plasmids, Lee and Gelvin, 2008) may also be preferred, especially for transient expression systems.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

Most preferred vectors are the pEAQ vectors described below which permit direct cloning version by use of a polylinker between the 5' leader and 3' UTRs of an expression cassette including a translational enhancer of the invention, positioned on a T-DNA which also contains a suppressor of gene silencing and an NPTII cassettes. The polylinker also encodes one or two sets of 6× Histidine residues to allow the fusion of N- or C terminal His-tags to facilitate protein purification.

An advantage of pEAQ-derived vectors is that each component of a multi-chain protein such as an IgG can automatically be delivered to each infected cell.

The present invention also provides methods of expressing proteins, e.g. heterologous proteins, in host organisms such as plants, yeast, insect or mammalian cells, using a gene expression system of the invention.

The present invention further provides a method of enhancing the translation of a heterologous protein of interest from a gene or ORF encoding the same which is operably linked to an RNA2-derived sequence as described above, the method comprising mutating a target initiation site in the RNA2-derived sequence.

The enhancer sequences described herein may also be used with bipartite expression systems as described in WO/2007/135480. The invention therefore also relates to gene expression systems based on truncated RNA-2 gene segments, optionally further comprising a second gene construct encoding a suppressor of gene silencing operably linked to promoter and terminator sequences.

In a further aspect the present invention therefore relates to a gene expression system comprising:

(a) a first gene construct comprising a truncated RNA-2 of a bipartite virus genome carrying at least one foreign gene encoding a heterologous protein of interest operably linked to promoter and terminator sequences, wherein the gene construct comprises a mutated target initiation site upstream of the foreign gene; and optionally (b) a second gene construct comprising RNA-1 of said bipartite virus genome operably linked to promoter and terminator sequences; and optionally (c) a third gene construct, optionally incorporated within said first gene construct, said second gene construct or both, comprising a suppressor of gene silencing operably linked to promoter and terminator sequences.

The presence of a suppressor of gene silencing in a gene expression system (including any of those described above) of the invention is preferred but not essential. Thus, a gene expression system, as defined above, preferably comprises a third gene construct, optionally incorporated within said first gene construct, said second gene construct or both, comprising a suppressor of gene silencing operably linked to promoter and terminator sequences.

Thus, in another aspect the present invention provides a method of expressing a protein in a plant comprising the steps of:
(a) introducing a gene expression construct of the invention into a plant cell; and optionally
(b) introducing a second gene construct comprising RNA-1 of said bipartite virus genome operably linked to promoter and terminator sequences into the plant cell; and optionally
(c) introducing a third gene construct, optionally incorporated within said first gene construct, said second gene construct or both, comprising a suppressor of gene silencing operably linked to promoter and terminator sequences into the plant cell.

Preferably, a method of expressing a protein in a plant, as defined above, comprises the step of introducing a third gene construct, optionally incorporated within said first gene construct, said second gene construct or both, comprising a suppressor of gene silencing operably linked to promoter and terminator sequences into the plant cell.

The present invention also provides methods comprising introduction of such a construct into a plant cell.

The present inventors have shown very high expression levels by incorporating both a gene of interest and a suppressor of silencing onto the same T-DNA as the translational enhancer. Preferred embodiments may therefore utilise all these components are present on the same T-DNA.

Additionally it should be understood that the RNA-1 is not required for high level expression in the systems described herein, and indeed the "CPMV-HT" system described herein is not by the action of RNA-1.

Thus in a further aspect the present invention therefore relates to a gene expression system comprising:
(a) a first gene construct comprising a truncated RNA-2 of a bipartite virus genome carrying at least one foreign gene encoding a heterologous protein of interest operably linked to promoter and terminator sequences, wherein the gene construct comprises a mutated target initiation site upstream of the foreign gene; and optionally
(b) a second gene construct optionally incorporated within said first gene construct, a suppressor of gene silencing operably linked to promoter and terminator sequences.

Thus, in another aspect the present invention provides a method of expressing a protein in a plant comprising the steps of:
(a) introducing a gene expression construct of the invention into a plant cell; and optionally
(b) introducing a second gene construct optionally incorporated within said first gene construct, comprising a suppressor of gene silencing operably linked to promoter and terminator sequences into the plant cell.

Suppressors of gene silencing useful in these aspects are known in the art and described in WO/2007/135480. They include HcPro from Potato virus Y, He-Pro from TEV, P19 from TBSV, rgsCam, B2 protein from FHV, the small coat protein of CPMV, and coat protein from TCV. Most preferably, the RNA-2 of the system is truncated such that no infectious virus is produced.

A preferred suppressor when producing stable transgenic plants is the P19 suppressor incorporating a R43W mutation.

In a further aspect of the invention, there is disclosed a host cell containing a heterologous construct according to the present invention.

Gene expression vectors of the invention may be transiently or stably incorporated into plant cells.

For small scale production, mechanical agroinfiltration of leaves with constructs of the invention. Scale-up is achieved through, for example, the use of vacuum infiltration.

In other embodiments, an expression vector of the invention may be stably incorporated into the genome of the transgenic plant or plant cell.

In one aspect the invention may further comprise the step of regenerating a plant from a transformed plant cell.

Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809). If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

Nucleic acid can be introduced into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984; the floral dip method of Clough and Bent, 1998), particle or microprojectile bombardment (U.S. Pat. No. 5,100,792, EP-A-444882, EP-A-434616) microinjection (WO 92/09696, WO 94/00583, EP 331083, EP 175966, Green et al. (1987) Plant Tissue and Cell Culture, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11. Ti-plasmids, particularly binary vectors, are discussed in more detail below.

*Agrobacterium* transformation is widely used by those skilled in the art to transform dicotyledonous species. However there has also been considerable success in the routine production of stable, fertile transgenic plants in almost all economically relevant monocot plants (see e.g. Hiei et al. (1994) *The Plant Journal* 6, 271-282)). Microprojectile bombardment, electroporation and direct DNA uptake are preferred where *Agrobacterium* alone is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice.

It will be apparent to the skilled person that the particular choice of a transformation system to introduce nucleic acid into plant cells is not essential to or a limitation of the invention, nor is the choice of technique for plant regeneration. In experiments performed by the inventors, the enhanced expression effect is seen in a variety of integration patterns of the T-DNA.

Thus various aspects of the present invention provide a method of transforming a plant cell involving introduction of a construct of the invention into a plant tissue (e.g. a plant cell) and causing or allowing recombination between the vector and the plant cell genome to introduce a nucleic acid according to the present invention into the genome. This may be done so as to effect transient expression.

Alternatively, following transformation of plant tissue, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals such as rice, maize, wheat, oat, and barley plus many other plant species (reviewed in Shimamoto, K. (1994) *Current Opinion in Biotechnology* 5, 158-162.; Vasil, et al. (1992) Bio/Technology 10, 667-674; Vain et al., 1995, *Biotechnology Advances* 13 (4): 653-671; Vasil, 1996, *Nature Biotechnology* 14 page 702).

Regenerated plants or parts thereof may be used to provide clones, seed, selfed or hybrid progeny and descendants (e.g. F1 and F2 descendants), cuttings (e.g. edible parts), propagules, etc.

The invention further provides a transgenic organism (for example obtained or obtainable by a method described herein) in which an expression vector or cassette has been introduced, and wherein the heterologous gene in the cassette is expressed at an enhanced level, The invention further comprises a method for generating the protein of interest, which method comprises the steps of performing a method (or using an organism) as described above, and optionally harvesting, at least, a tissue in which the protein of interest has been expressed and isolating the protein of interest from the tissue.

Specifically, the present invention therefore provides a transgenic plant or plant cell transiently transfected with an expression vector of the invention.

In a further aspect, the present invention also provides a transgenic plant or plant cell stably transformed with an expression vector of the invention.

The invention also provides a plant propagule from such plants, that is any part which may be used in reproduction or propagation, sexual or asexual, including cuttings, seed and so on. It also provides any part of these plants which includes the plant cells or heterologous DNA described above.

Thus in various aspects (and without limitation) the invention provides:

Nucleic acids consisting or consisting essentially of an enhancer sequence of the invention (which enhancer sequence may (for example) consist of nucleotides 1 to 512 of the CPMV RNA-2 genome segment, or be derived from that, or from another RNA-2 genome segment of a bipartite RNA virus, in each case in which the target initiation site corresponding to CPMV RNA-2 position 161 is mutated).

Gene expression systems comprising such enhancer sequences, for example upstream of an ORF encoding a protein of interest, or a polylinker, and optionally terminator.

Bipartite expression systems as described in WO/2007/135480 modified according to the present invention to use enhancer sequences described herein.

Expression cassettes comprising: (i) a promoter, operably linked to (ii) an enhancer sequence as described above (iii) a polylinker or gene of interest it is desired to express (iv) the cognate 3' UTR (i.e. from the 3' UTR of the CPMV RNA-2 genome segment), (v) a terminator sequence.

Methods of expressing proteins, e.g. heterologous proteins, in host organisms such as plants using gene expression systems or vectors of the invention.

Host cells and organisms (e.g. plants or yeasts) expressing proteins from the gene expression systems or vectors of the invention and methods of producing the same.

"Gene" unless context demands otherwise refers to any nucleic acid encoding genetic information for translation into a peptide, polypeptide or protein. Thus unless context demands otherwise it used interchangeably with "ORF".

The genes which it may be desired to express may be transgenes or endogenes.

Genes of interest include those encoding agronomic traits, insect resistance, disease resistance, herbicide resistance, sterility, grain characteristics, and the like. The genes may be involved in metabolism of oil, starch, carbohydrates, nutrients, etc. Thus genes or traits of interest include, but are not limited to, environmental- or stress-related traits, disease-related traits, and traits affecting agronomic performance. Target sequences also include genes responsible for the synthesis of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

Most preferably the targeted genes in monocots and/or dicots may include those encoding enzymes responsible for oil production in plants such as rape, sunflower, soya bean and maize; enzymes involved in starch synthesis in plants such as potato, maize, cereals; enzymes which synthesise, or proteins which are themselves, natural medicaments such as pharmaceuticals or veterinary products.

Heterologous nucleic acids may encode, inter alia, genes of bacterial, fungal, plant or animal origin. The polypeptides may be utilised in planta (to modify the characteristics of the plant e.g. with respect to pest susceptibility, vigour, tissue differentiation, fertility, nutritional value etc.) or the plant may be an intermediate for producing the polypeptides which can be purified therefrom for use elsewhere. Such proteins include, but are not limited to retinoblastoma protein, p53, angiostatin, and leptin. Likewise, the methods of the invention can be used to produce mammalian regulatory proteins. Other sequences of interest include proteins, hormones, growth factors, cytokines, serum albumin, haemoglobin, collagen, etc.

Thus the target gene or nucleotide sequence preferably encodes a protein of interest which is: an insect resistance protein; a disease resistance protein; a herbicide resistance protein; a mammalian protein.

"Vector" is defined to include, inter alia, any plasmid, cosmid, phage, viral or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication). The constructs used will be wholly or partially synthetic. In particular they are recombinant in that nucleic acid sequences which are not found together in nature (do not run contiguously) have been ligated or otherwise combined artificially. Unless specified otherwise a vector according to the present invention need not include a promoter or other regulatory sequence, particularly if the vector is to be used to introduce the nucleic acid into cells for recombination into the genome.

"Binary Vector": as is well known to those skilled in the art, a binary vector system includes (a) border sequences which permit the transfer of a desired nucleotide sequence into a plant cell genome; (b) desired nucleotide sequence itself, which will generally comprise an expression cassette of (i) a plant active promoter, operably linked to (ii) the target sequence and\or enhancer as appropriate. The desired nucleotide sequence is situated between the border sequences and is capable of being inserted into a plant genome under appropriate conditions. The binary vector system will generally require other sequence (derived from *A. tumefaciens*) to effect the integration. Generally this may be achieved by use of so called "agro-infiltration" which uses *Agrobacterium*-mediated transient transformation. Briefly, this technique is based on the property of *Agrobacterium tumefaciens* to transfer a portion of its DNA ("T-DNA") into a host cell where it may become integrated into nuclear DNA. The T-DNA is defined by left and right border sequences which are around 21-23 nucleotides in length. The infiltration may be achieved e.g. by syringe (in leaves) or vacuum (whole plants). In the present invention the border sequences will generally be included around the desired nucleotide sequence (the T-DNA) with the one or more vectors being introduced into the plant material by agro-infiltration.

"Expression cassette" refers to a situation in which a nucleic acid is under the control of, and operably linked to, an appropriate promoter or other regulatory elements for transcription in a host cell such as a microbial or plant cell.

A "promoter" is a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter.

"Plant" species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria Italica*), finger millet, (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), *Nicotiana benthamiana*, potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. The skilled person will appreciate that the tropism of the viral vectors disclosed herein varies. However, determining susceptibility to such viruses is well within the purview of the skilled person. Moreover, it may be possible to alter such specificity by recombinantly expressing receptors which facilitate viral entry into a plant cell.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

BRIEF DESCRIPTION OF THE DRAWINGS

FIG. 14 shows the cloning and expression of GFP from pEAQ-HT in native and his-tagged variants. (A) Schematic representation of the pEAQ-HT T-DNA with polylinker detail. (B) Spectrofluorometric analysis of GFP expression. spK=pEAQspecialK-GFP-HT, GFP, HisGFP, and GFPHis=pEAQ-HT clones. (C) 12% SDS-PAGE and western analysis of GFP expression. C=control extract.

FIG. 15 shows a nucleic construct of the present invention which is suitable for use in insect cells as part of a baculovirus vector.

EXAMPLES

Example 1

1.1 Methods
Creation of Expression Vector FSC2 and its Derivatives

A useful cloning vector for the expression of foreign proteins from a pBinP-1-GFP-based plasmid (Cañizares et al., 2006) was created by excising the complete sequence of RNA-2 flanked by the Cauliflower mosaic virus (CaMV) 35S promoter and nopaline synthase (nos) terminator from pBinP-S2NT (Liu and Lomonossoff, 2002) and inserting it into mutagenesis plasmid pM81W (Liu and Lomonossoff, 2006) as an AscI/PacI fragment. The resulting plasmid, pM81W-S2NT, was subjected to a single round of mutagenesis which simultaneously introduced four changes (see method in Liu and Lomonossoff, 2006) to give pM81B-S2NT-1. The mutagenesis removed two BspHI sites from the vector backbone and introduced a BspHI site (T/CATGA) around AUG 512 and a StuI site (AGG/CCT) after UAA 3299, the termination codon for the RNA-2-encoded polyprotein. Subsequently, the BamHI/AscI fragment was excised from pBinP-NS-1 (Liu et al., 2005) and ligated into similarly digested pM81B-S2NT-1, yielding pM81-FSC-1. This vector allows the whole of the RNA-2 ORF downstream of AUG 512 to be excised by digestion with BspHI and StuI and replaced with any sequence with BspHI and StuI (blunt)-compatible ends. The use of the BspHI site is important as it preserves the AUG at 512 and this initiator is used to drive translation of the inserted gene. To express the foreign gene in plants, the pM81-FSC-1-derived plasmid is digested with AscI and PacI and the fragment containing the expression cassette including the foreign sequences transferred to similarly digested pBIN-PLUS and the resulting plasmids are finally transformed into A. tumefaciens.

Figure 2:
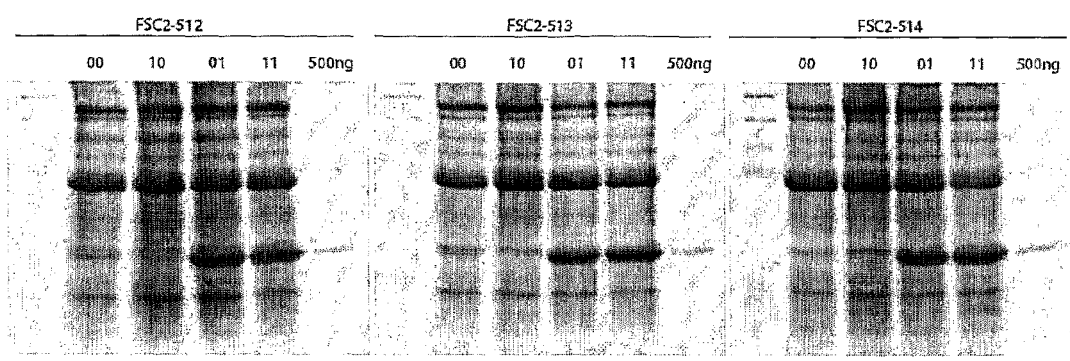
FIG. 2 shows the level of soluble green fluorescent protein (GFP) expressed in plants transfected with the CPMV expression vectors schematically illustrated in FIG. 1. In expression vectors FSC2-512, FSC2-513 and FSC2-514, the gene encoding GFP was inserted after the initiation codon at position 512, 513 and 514, respectively. The lanes of the SDS-PAGE gels are marked 00, 10, 01 and 11, depending on which of the initiation sites in the CPMV vector, at positions 115 and 161, are intact or mutated. The lane marked '500 ng' shows the position of a band corresponding to 500 ng of GFP protein and thus indicates the expected position of GFP protein expressed from the CPMV expression vectors. The left hand lane of each SDS-PAGE gel shows the position of protein size markers.
Figure 3:
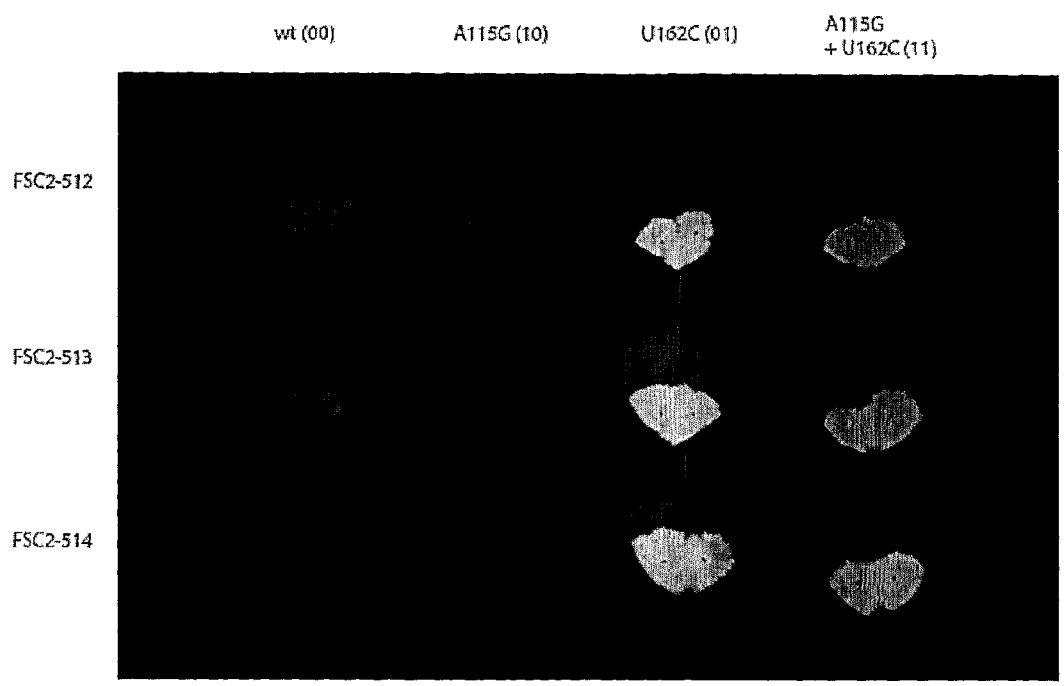
FIG. 3 shows the level of GFP expression in *Nicotiana benthamiana* leaves transfected with the same CPMV expression vectors used in the experiment illustrated in FIG. 2. The pale regions at the tips of the leaves correspond to regions of GFP expression. Mutations made in order to inactivate the initiation sites at positions 115 and/or 161 in expression vectors 10, 01 and 11 are also indicated.
Figure 4:
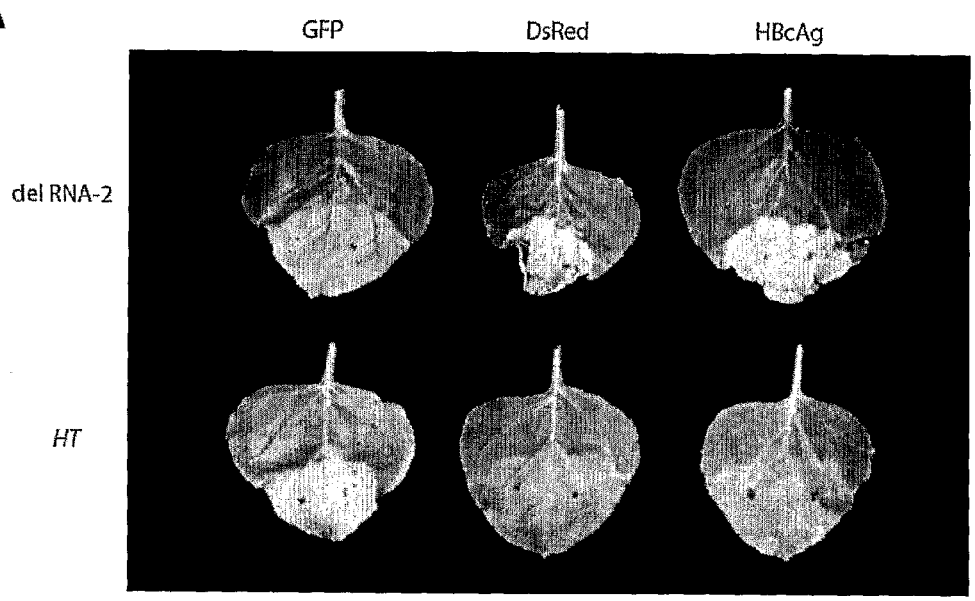
FIG. 4 shows a comparison of Del-RNA-2 (expression vector 00 [FSC2-512] in FIG. 1) and HT (expression vector 01 [FSC2-512] in FIG. 1) for transient expression of green fluorescent protein (GFP), Discosoma red fluorescent protein (DsRed), and the hepatitis B core antigen (HBcAg). del-RNA-2 or HT clones for each protein were infiltrated with the silencing suppressor P19. (A) Tissue 7 days after infiltration with delRNA-2 constructs becomes necrotic when DsRed or HBcAg is expressed whereas this is not the case for HT driven expression. In fact, tissue expressing DsRed by HT looks visibly red under day light conditions. (B) Coomassie-stained SDS-PAGE analysis of protein expression. The prominent bands corresponding to recombinant proteins as indicated were confirmed by western blotting. 1—marker, 2—uninfiltrated tissue, 3—delRNA-2 construct, 4—HT construct, 5—commercial standard where available. Crude extracts from approximately 5 mg of infiltrated tissue were loaded per lane as was 2 µg of GFP standard and 2 µg of HBcAg standard. No standard for DsRed was available at the time.
Figure 4:
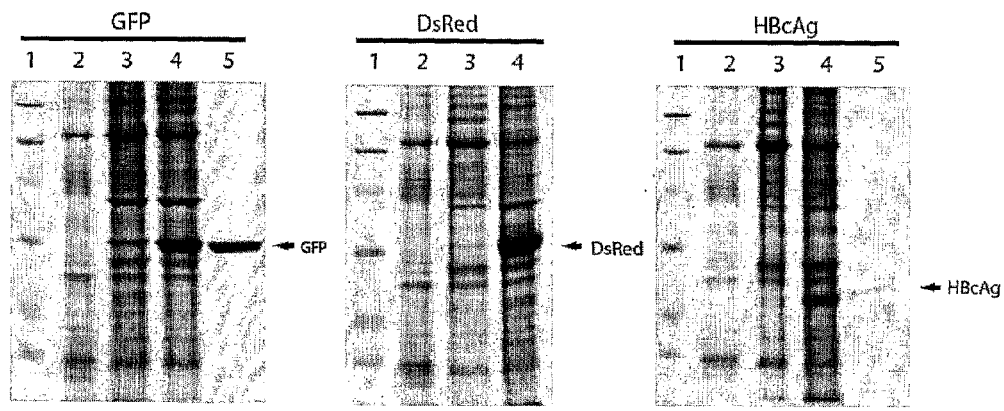
Figure 5:
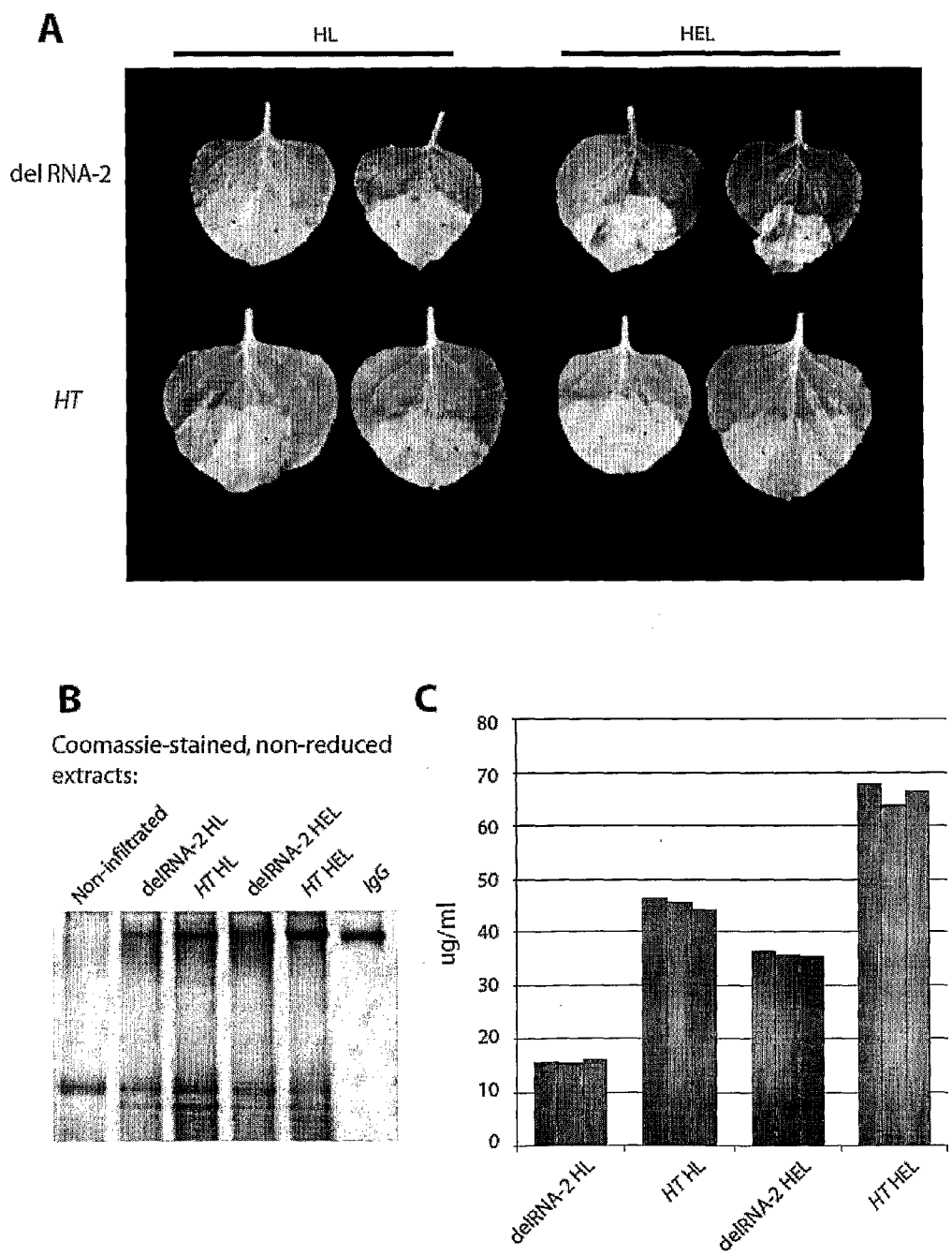
FIG. 5 shows an initial comparison of Del-RNA-2 (expression vector 00 [FSC2-512] in FIG. 1) and HT (expression vector 01 [FSC2-512] in FIG. 1) for transient expression of the human anti-Human Immunodeficiency Virus antibody 2G12. The IgG Heavy chain was either in natural form (HL) or ER-retained (HEL) and infiltrated with the light chain and P19. (A) Expression of 2G12-HEL by del-RNA-2 leads to necrosis of infiltrated tissue whereas this does not occur for HT expression. (B) SOS-PAGE analysis of crude extracts of tissue infiltrated with the antibody heavy chains (delRNA-2 or HT) plus P19. For each sample crude extract from 5 mg of infiltrated tissue was loaded as was 1 µg of standard human IgG. A band corresponding to 2G12 is easily visible after coomassie staining. (C) Accumulation of antibody 2G12 after 5 days was measured by capture to protein A and surface plasmon resonance spectroscopy and represents the concentration following extraction in 2 volumes of buffer (PBS, 5 mM EDTA). Therefore, we can derive fresh weight concentrations approaching 150 mg/kg (for HT HEL) without any optimisation of plant incubation or extraction. Three samples were measured for each treatment.
Figure 6:
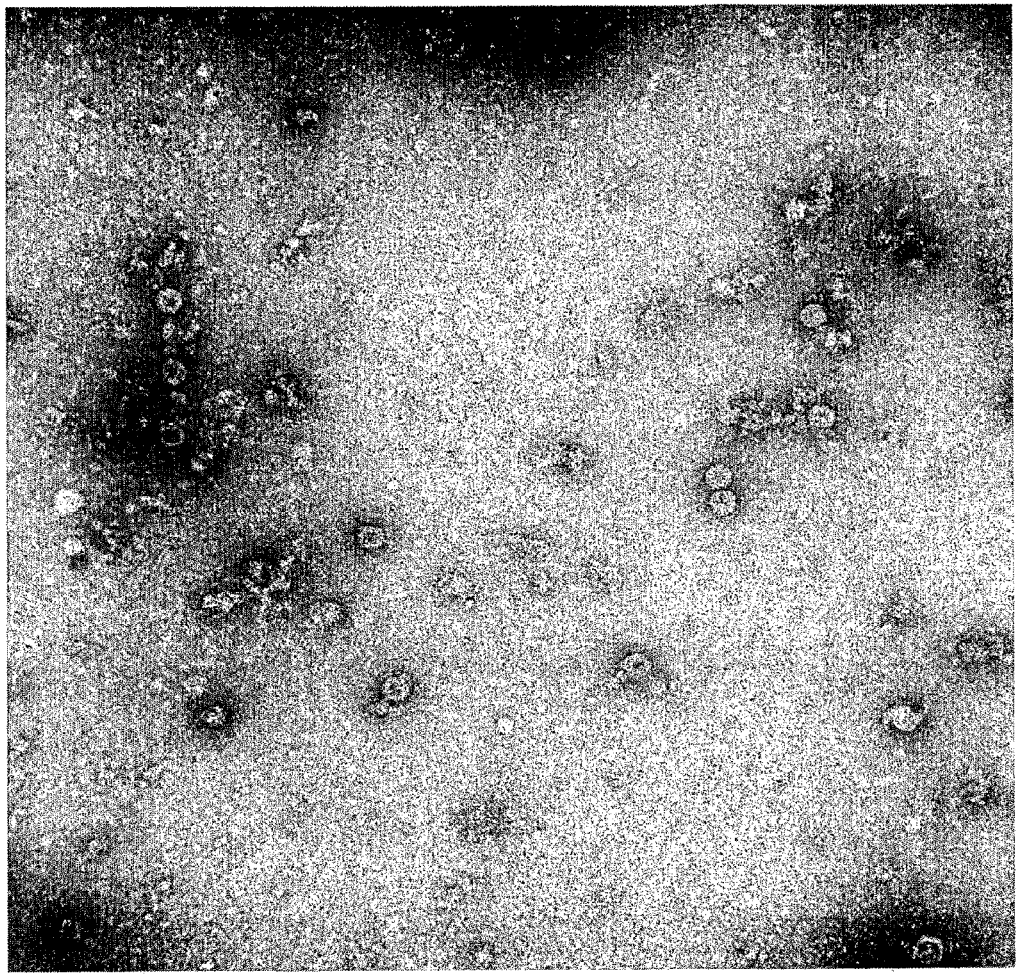
FIG. 6 shows an electron micrograph of assembled HBcAg particles, which were expressed using the HT (expression vector 01 [FSC2-512] in FIG. 1) expression system described herein. The assembled HBcAg particles appear as hollow spheres, about 30 nm in diameter. The sap containing the HBcAg particles was not concentrated before the electron micrograph was taken, although unwanted salts were removed. Therefore, the electron micrograph represents the concentration of HBcAg particles in the sap.

To improve the ease of cloning, expand the choice of applicable restriction enzymes, and to investigate the effect of reading frame on foreign gene expression, the whole RNA-2 ORF was replaced with a short polylinker. A combination of oligonucleotide insertion and site-directed mutagenesis resulted in pM81-FSC-2, which allows cloning with NruI (TCG/CGA) and either XhoI (C/TCGAG) or StuI. The terminal adenine of the NruI site lies at position 512 thereby preserving the AUG found here. The modifications altered nucleotides immediately 5' to the AUG at 512, however, a good context was maintained. Cloning GFP into pM81-FSC-2 such that its translation was initiated from an AUG at 512, 513, 514, or 515 gave the pM81-FSC-1 derived constructs pM81-FSC2-512, pM81-FSC2-513, pM81-FSC2-514, and pM81-FSC2-515. These pM81-based plasmids are the cloning vectors containing the expression cassettes which were then transferred into the binary vector to produce the expression vectors FSC2-512, FSC2-513 and FSC2-514 used in the Experiments shown in FIGS. 2 and 3. Differences between the sequence of the wt RNA-2 genome segment of CPMV and the pM81-FSC1 and pM81-FSC2 vectors are shown in Table 3. Nucleotides altered in the vectors compared with the wt CPMV sequence are shown as capital letters.

Agrobacteria-mediated transient transformation following mobilisation into pBINPLUS (as outlined above for pM81-FSC-1) showed that lower protein levels are obtained when frame continuity between AUG 161 and the downstream AUG is not maintained. There was a significant decrease in the amount of GFP translated from the +1 and +2 positions relative to AUGs 161 and 512, whereas translation from the +3 position (that is, from 515 and back in frame) was as efficient as translation from an AUG at 512. To show that this was not due to weakened contexts of the AUGs at 513 and (to a lesser extent) 514, FSC2-515+ was created to initiate from +3 position but with the same poor context as FSC2-513. Expression from FSC2-515+ was as high as that achieved from FSC2-512 or 515, indicating that inferior context does not explain the reduction in expression from FSC2-513 and 514.

Given that the known mechanisms by which translation can escape the first-AUG rule are not known to require frame continuity, it is intriguing that efficient translation from a deleted RNA-2-based vector depends on frame continuity between AUG 161 and the downstream AUG. In order to understand, and hopefully overcome this phenomenon, a series of mutants were created with modifications to the 5' sequence of RNA-2. Complement pairs of oligonucleotides (see Table 2) were used in the site-directed mutagenesis of pM81-FSC2-512, 513, and 514. The mutations removed either AUG 115 (the start codon for the uORF), AUG 161 (without changing the amino acid sequence of the uORF), or both of these upstream initiation sites. Double mutations were made by mutagenizing the A115G mutants with the U162C oligos (Table 2).

Transient expression from these mutant transcripts was carried out as described for previous pM81-FSC-2 constructs. Analysis of expression of GFP from these mutants using coomassie-stained SDS-PAGE (FIG. 2) or UV light to visualise whole leaves (FIG. 3) shows a strong increase in expression in the absence of the AUG at 161. Furthermore, the removal of AUG 161 alone or both AUGs 115 and 161 alleviates the dependence on frame continuity between AUG 161 and the downstream AUG. In contrast, removal of just AUG 115 appears to enhance this dependency as well as generally inhibit translation. In conclusion, the uORF appears to function to down-regulate translation from AUG 161, which is both generally inhibitory and confers dependence on frame continuity.

Electron Microscopy of Sap Containing HBcAg Particles

The sap used for the electron micrograph of the assembled HBcAg particles shown in FIG. 6 was prepared as follows. Leaf tissue was extracted in 2 volumes of Tris/NaCl buffer and exchanged for TE without concentration on a 100 kDa MWCO column. The final concentration of HBcAg was approximately 0.2 mg/ml as judged by comparison to standard on a coomassie stained SDS-PAGE gel.

1.2 Results (1) Effect of altering relative phases of the initiation sites at position 161 (AUG161) and 512 (AUG512).

To achieve this extra nucleotides were inserted immediately upstream of AUG512 (FSC2-512) to move the AUG to position 513, 514 and 515 (FSC2-513, FSC2-514 and FSC2-515) (FIG. 1). Putting AUG512 out-of-phase with AUG161 (FSC2-513 and FSC2-514) gave less GFP expression as judged by fluorescence (FIG. 3) and Coomassie-stained gels (FIG. 2). Restoring the phase (FSC2-515) brought expression back to levels seen with the natural situation (FSC2-512). The conclusion is that when AUG161 is present, initiation at a downstream AUG is most efficient when it is in-phase with the AUG at position 161.

(2) Removal of the initiation site at position 115 (AUG115) coupled with altering relative phases of the initiation sites at position 161 (AUG161) and 512 (AUG512).

Removal of AUG115 has little or no effect when GFP expression is driven from AUG512 i.e. when this second AUG is in phase with AUG161 (see lanes labelled 10 in FIGS. 2 and 3). However, deletion of AUG115 when the second AUG is out-of-phase with AUG161 (513, 514) results in virtually no GFP expression (see lanes labelled 10 in FIGS. 2 and 3). Conclusion: AUG115 is somehow involved in the ability of ribosomes to by-pass AUG161 and reach AUG512. However, this requires the downstream AUG to be in the correct phase.

(3) Effect of removal of the initiation site at position 161 (AUG 161)

The effect of this mutation is incredibly dramatic with GFP expression levels reaching 20-30 times the amount found when AUG161 is present (see lanes labelled 01 in FIGS. 2 and 3). Furthermore, it no longer appears to matter which phase AUG512 is in, though in the absence of AUG161, the idea of phase does not mean much. In addition the presence or absence of AUG115 makes no difference (see lanes labelled 11 in FIGS. 2 and 3).

When using the delRNA-2 (expression vector 00 [FSC2-512] in FIG. 1) constructs for DsRed and HBcAg expression, within 5 days infiltrated patches have lost turgor pressure and become chlorotic (pale). By 7 days the tissue appears grey and is completely dead. When using HT (expression vector 01 [FSC2-512] in FIG. 1), the tissue remains turgid after 7 days and the only sign of stress is slight chlorosis of HBcAg expressing tissue. When the heavy chain of the 2G12 IgG is expressed by delRNA-2 and retained in the ER, chlorosis is evident after 7 days, whereas for HT this is not observed. The level of necrosis seen in plants when using HT to express a heterologous protein is thus much lower, despite the higher level of heterologous protein expression achieved, than when using delRNA-2 to express the heterologous protein.

Discussion

Very high levels of foreign gene expression can be expressed from the delRNA-2 constructs by deleting AUG161. At present, using GFP, we estimate the levels as 25-30% of total soluble protein (TSP) or approximately 1 gram expressed protein per Kg leaves. This is a tremendous level and the approach we use is extremely simple. The fact that we no longer need to preserve a reading frame means that user-friendly vectors with polylinkers can be produced.

Example 2

2.1 Background

As described in Example 1, to investigate the features necessary for the 5' untranslated region (UTR) of CPMC RNA-2 necessary for efficient expression, the present inventors addressed the role of two AUG codons found within the 5' leader sequence upstream of the main initiation start site. The inventors demonstrated that deletion of an in-frame start codon (161) upstream of the main translation initiation site (512) led to a massive increase in foreign protein accumulation.

Using this system the inventors have shown that by 6 d postinfiltration, a number of unrelated proteins, including a full-size IgG and a self-assembling virus-like particle, were expressed to >10% and 20% of total extractable protein, respectively. Thus, this system provides an ideal vehicle for high-level expression that does not rely on viral replication of transcripts.

Figure 1:
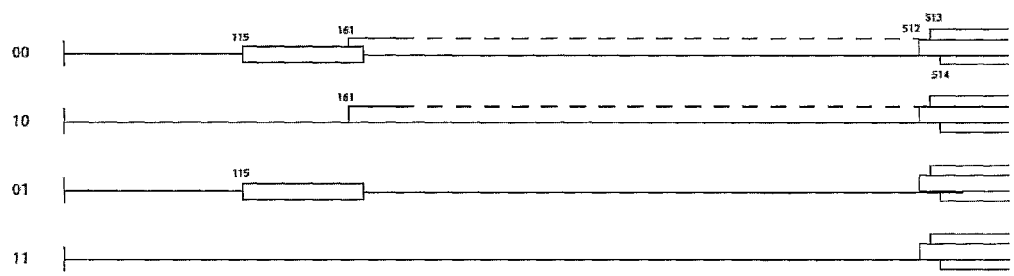
FIG. 1 shows a schematic diagram of CPMV expression vectors 00, 10, 01 and 11. In 00 expression vectors the initiation sites at positions 115 and 161 are intact. In 10 expression vectors the initiation site at positions 115 has been mutated but the initiation site at position 161 is intact. In 01 expression vectors the initiation site at positions 161 has been mutated but the initiation site at position 115 is intact. In 11 expression vectors the initiation sites at positions 115 and 161 are both mutated. CPMV expression vectors 00, 10, 01 and 11 also comprise an initiation site at either position 512 (FSC2-152), 513 (FSC2-513) or 514 (FSC2-514). Bars are used to indicate the initiation sites from which protein expression is expressed to occur.

This new system (as exemplified by expression vector 01 [FSC-512] in FIG. 1) has been called "CPMV-HT" for hypertranslatable Cow Pea Mosaic Virus protein expression system.

The HT-CPMV system shows dramatic increases in protein levels and thus is an excellent method for the rapid, high-level expression of foreign proteins in plants.

A growing array of binary vectors has been developed for plant transformation over the past 25 years (Hellens et al., 2000b; Veluthambi et al., 2003; Lee and Gelvin, 2008). The main aim of these developments has thus far focused on improving stable integration by, for example, expanding the host range for Agrobacteria (Hiei et al., 1994), the creation of a series of vectors that allow a choice of selectable markers, expression cassettes and fusion proteins (exemplified by the pCAMBIA range of open source binary vectors; http://www.cambia.org/daisy/bioforge_legacy/3725.html), or by developing systems for minimising extraneous DNA integration and marker-free transformation (for example pCLEAN; Thole et al., 2007).

Binary vectors have also been engineered to replicate at low copy numbers to reduce the frequency of multiple integration events of the same transgene, as this can lead to gene silencing (Johansen and Carrington, 2001).

However, for transient expression, ensuring efficient integration into the host nucleus and the presence of marker for in planta selection are not strictly required. Furthermore, upon agro-infiltration each cell is flooded with T-DNA molecules, which are thought to be transcriptionally competent in the nucleus even without genome integration (Janssen and Gardner, 1989; Narasimhulu et al., 1996). This suggests that transient expression could benefit from higher copy number binary plasmids.

Another area of improvement of binary vectors has been the reduction in size of the vector backbone. Two prominent examples that continue to demonstrate the benefits of smaller plasmids are pPZP (Hajdukiewicz et al., 1994) and pGREEN (Helens et al., 2000a). In addition to improving the efficiency of cloning procedures and bacterial transformation, these vectors have provided templates for expression systems that rely on multiple cassettes present on a single T-DNA (Tzfira et al., 2005; Thole et al., 2007).

The present example discloses non-obvious refinements of this vector which facilitates its practical use by permitting the cloning to be done in a single step, rather than requiring subcloning of expression cassettes between the cloning vector (e.g. pM81-FSC2) and expression systems (e.g. PBINPLUS). More specifically, the results herein show it was possible to drastically reduce the size of pBINPLUS without compromising performance in terms of replication and TDNA transfer. Furthermore, elements of the CPMV-HT system have been incorporated into the resulting vector in a modular fashion such that multiple proteins can be expressed from a single T-DNA. These improvements have led to the creation of a versatile, high-level expression vector that allows efficient direct cloning of foreign genes.

Figure 9:
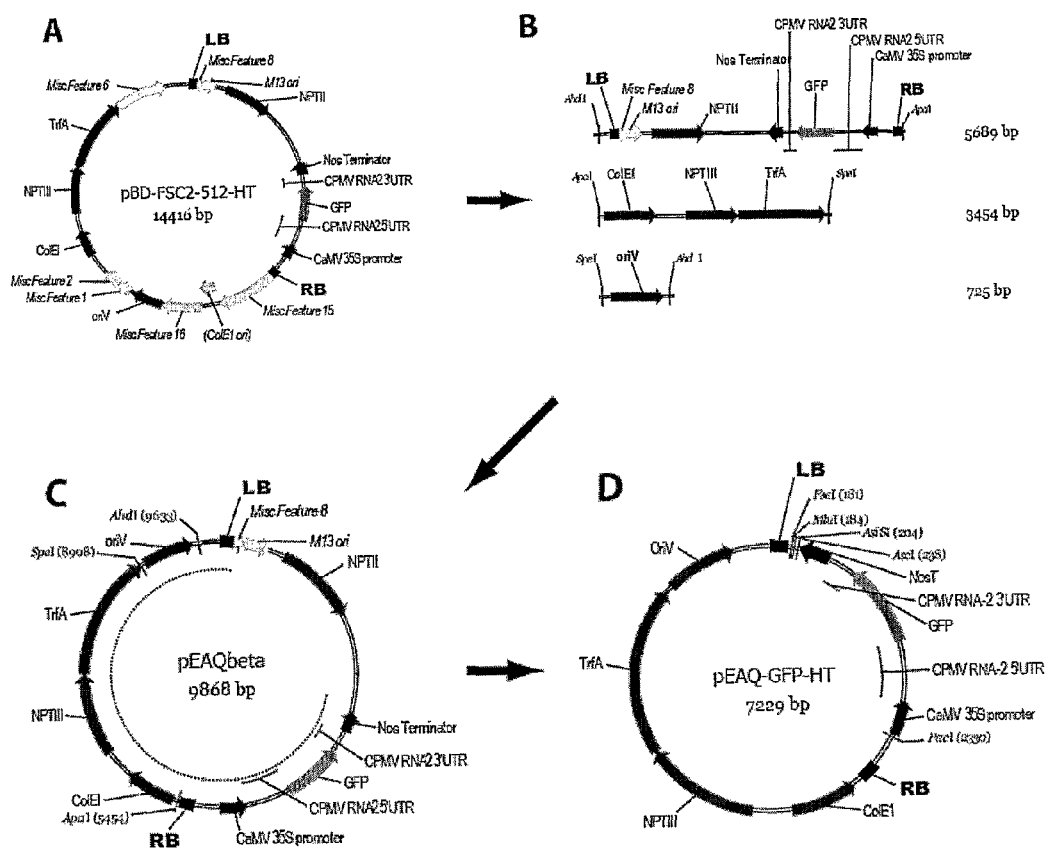
FIG. 9 shows a schematic representation of the construction of pEAQ. (A) Starting pBINPLUS-based plasmid with extraneous sequence shown in grey. (B) PCR products containing essential elements of the binary vector. (C) Intermediate plasmid following 3-part ligation of end-tailored PCR products. (D) Final plasmid following amplification and subsequent ligation of two fragments from the intermediate.

2.2 Materials and Methods pBD-FSC2-512-U162C (HT), contains the FSC2-512-U162C cassette (see Example 1) inserted into the PacI/AscI sites of pBINPLUS (van Engelen et al., 1995). The essential segments of this plasmid (see below) were amplified with the high fidelity polymerase, PHUSION (New England Biolabs) using oligonucleotides encoding unique restriction enzyme sites for re-ligation (Table 4.1). The T-DNA region was amplified with a sense primer homologous to sequence upstream of a unique AhdI site (pBD-LB-F) and an antisense primer that included an ApaI site (pBD-RB-ApaI-R). A region including the ColEI origin of replication, the NPTIII gene, and the TrfA locus was amplified with a sense primer that included an ApaI site (pBD-ColEI-ApaI-F), and an antisense primer that included a SpeI site (pBD-TrfA-SpeI-R). The RK2 origin of replication (OriV) was amplified with a sense primer that included a SpeI site (pBD-oriVSpeI-F) and an antisense primer that included an AhdI site (pBD-oriV-AhdI-R). Following purification, the products were digested according to the unique restriction sites encoded at their termini and mixed for a three-point ligation. This resulted in the plasmid pEAQbeta, for which the ligation junctions were verified by sequencing. A deletion of approximately 1.2 kb from the T-DNA which had removed a portion of the nos terminator of the CPMV-GFP-HT cassette was detected. Therefore, a portion of the terminator including the right border from pBD-FSC2-GFP-HT was re-amplified with primers pMini>pMicroBIN-F2 and pBD-RB-ApaI-R, as was the pEAQbeta backbone, including the right border, using primers pBD-ColEI-ApaI-F and pMini>pMicroBIN-R (Table 4.1). The purified products were digested with ApaI and FseI and ligated to give pEAQ (FIG. 9).

The P19 gene flanked by 35S promoter and 35S terminator was amplified from pBIN61-P19 (Voinnet et al., 2003) using either 35SP19-PacI-F and 35SP19-AscIR, or 35SP19-FseI-F and 35S-P19-FseI-R as primers (Table 4.1). The NPTII gene flanked by the nos promoter and terminator was amplified from pBD-FSC2-GFPHT using primers pBD-NPTII-FseI-F and pBD-NPTII-FseI-R (Table 4.1). Following A-tailing, the amplified cassettes were ligated into pGEM-T easy (Promega). The P19 cassette excised from pGEM-T easy with FseI was ligated into FseI-digested pEAQ-GFP-HT to give pEAQexpress-GFP-HT. The NPTII cassette excised with FseI was ligated into FseI-digested pEAQ-GFP-HT in both directions to give pEAQselectK-GFP-HT and pEAQselectK (rev)-GFP-HT. The NPTII cassette was also excised with PacI/AscI and ligated into the AsiSI/MluI sites of pEAQselectK-GFP-HT to give pEAQspecialK-GFP-HT. The P19 in pGEM-T was subjected to site-directed mutagenesis by the QUICKCHANGE method (Stratagene) to effect the conversion of Arginine-43 to a tryptophan residue using primers P19-R43W-F and P19-R43W-R. The mutant P19 cassette was released with PacI/AscI digest and inserted into the AsiSI/MluI sites of pEAQselectK-GFP-HT to give pEAQspecialKm-GFP-HT.

Oligonucleotides encoding the sense and antisense strands of a short polylinker (Table 4.1) were annealed leaving the downstream half of an NruI site at the 5'end and an overhang matching that of XhoI at the 3' end. The annealed oligos were ligated with NruI/XhoI digested pM81-FSC2-A115G-U162C (see above) to give pM81-FSC2-POW. The NruI site was removed from the P19 cassette in pGEM-T by site-directed mutagenesis (QUICKCHANGE; Stratagene) with the primers P19-ΔNruI-F and P19-ΔNruI-R, and was re-inserted into the AsiSI/MluI sites of pEAQselectK-GFP-HT to give pEAQspecialKΔNruI-GFP-HT which showed no reduction in expression compared to pEAQspecialK-GFP-HT (data not shown). The PacI/AscI fragment from pM81-FSC2-POW was then released and inserted into similarly digested pEAQspecialKΔNruI-GFP-HT thereby replacing the GFP HT expression cassette and yielding pEAQ-HT. GFP was amplified from pBD-FSC2-GFP-HT with a set of four primers (Table 4.1) in three combinations for insertion into pEAQ-HT: GFP-AgeI-F and GFP-XhoI-R; GFP-AgeI-F and GFP-XmaI-R; and GFP-XmaI-F and GFP-XhoI-R. Purified PCR products were digested with the enzymes specified in their primers and inserted into appropriately digested pEAQ-HT to give pEAQ-HT-GFP, pEAQ-HT-GFPHis, and pEAQ-HT-HisGFP.

TABLE 4.1

Oligonucleotides used for amplification and mutagenesis. Restriction enzyme sites, or parts thereof, are shown in lower case, and mutations underlined in bold.

| SEQ ID NO: | Oligo | Sequence | Function |
|---|---|---|---|
| 14 | pBD-LB-F | GCCACTCAGCTTCCTCAGCGGCTTT | Sense primer for amplification of the region 6338-12085 of pBD-FSC2-GFP-HT |
| 15 | pBD-RB-ApaI-R | TATTAgggcccCCGGCGCCAGATCTGGGGAACCCTGTGG | Antisense primer for amplification of the region 6338-12085 of pBD-FSC2-GFP-HT with ApaI site |
| 16 | pBD-ColEI-ApaI-F | GACTTAgggcccGTCCATTTCCGCGCAGACGATGACGTCACT | Sense primer for amplification of the region 1704-5155 of pBD-FSC2-GFP-HT with ApaI site |
| 17 | pBD-TrfA-SpeI-R | GCATTAactagtCGCTGGCTGCTGAACCCCCAGCCGGAACTGACC | Antisense primer for amplification of the region 1704-5155 of pBD-FSC2-GFP-HT with SpeI site |
| 18 | pBD-oriV-SpeI-F | GTAGCactagtGTACATCACCGACGAGCAAGGC | Sense primer for amplification of the region 14373-670 of pBD-FSC2-GFP-HT with SpeI site |
| 19 | pBD-oriV-AhdI-R | CAGTAgacaggctgtcTCGCGGCCGAGGGGCGCAGCCC | Antisense primer for amplification of the region 14373-670 of pBD-FSC2-GFP-HT with AhdI site |
| 20 | pMini>pMicroBIN-F2 | ggccggccacgcgtTATCTGCAGAgcgatcgcGAATTGTGAGCGGATAACAATTTCACACAGGAAACAGCTATGACC | Sense primer for amplification of the region 2969-85 of pEAQbeta with FesI-MluI-AsiSI sites |
| 21 | pMini>pMicroBIN-R | gcgatcgcTCTGCAGATAacgcgtggccggccCTCACTGGTGAAAAGAAAAACCACCCAGTACATTAAAAACGTCC | Antisense primer for amplification of the region 2969-85 of pEAQbeta with AsiSI-MluI-FesIsites |
| 22 | 35SP19-PacI-F | ttaattaaGAATTCGAGCTCGGTACCCCCCTACTCC | Sense primer for amplification of the 35S-P19 cassette with PacI site |
| 23 | 35SP19-AscI-R | ggcgcgccATCTTTTATCTTTAGAGTTAAGAACTCTTTCG | Antisense primer for amplification of the 35S-P19 cassette with AscI site |
| 24 | 35SP19-FseI-F | ggccggccGAATTCGAGCTCGGTACCCCC | Sense primer for amplification of the 35S-P19 cassette with FseI site |
| 25 | 35SP19-FseI-R | ggccggccATCTTTTATCTTTAGAGTTAAG | Antisense primer for amplification of the 35S-P19 cassette with FseI site |
| 26 | pBD-NPTII-FseI-F | ggccggccTACAGTATGAGCGGAGAATTAAGGGAGTCACG | Sense primer for amplification of the NPTII cassette from pBD-FSC2-GFP-HT with FseI site |

TABLE 4.1-continued

Oligonucleotides used for amplification and mutagenesis.
Restriction enzyme sites, or parts thereof, are
shown in lower case, and mutations underlined in bold.

| SEQ ID NO: | Oligo | Sequence | Function |
|---|---|---|---|
| 27 | pBD-NPTII-FseI-R | ggccggccTACAGTCCCGATCTAGTAACATAGATGACACCGCGC | Antisense primer for amplification of the NPTII cassette from pBD-FSC2-GFP-HT with FseI site |
| 28 | P19-R43W-F | CGAGTTGGACTGAGTGGTGGCTACATAACGATGAG | Sense primer for mutagenesis of arginine 43 of P19 to a tryptophan residue |
| 29 | P19-R43W-R | CTCATCGTTATGTAGCCACCACTCAGTCCAACTCG | Antisense primer for mutagenesis of arginine 43 of P19 to a tryptophan residue |
| 30 | P19-ΔNruI-F | CCGTTTCTGGAGGGTCTCGAACTCTTCAGCATC | Sense primer for the silent mutagenesis of the NruI restriction site within P19 |
| 31 | P19-ΔNruI-R | GATGCTGAAGAGTTCGAGACCCTCCAGAAACGG | Antisense primer for the silent mutagenesis of the NruI restriction site within P19 |
| 32 | POW-F | cgaccggtATGCATCACCATCACCATCATcccgggCATCACCATCACCATCACTAGc | Sense oligo for polylinker, POW |
| 33 | POW-R | tcgagCTAGTGATGGTGATGGTGATGcccgggATGATGGTGATGGTGATGCATaccggttcg | Sense oligo for polylinker, POW |
| 34 | GFP-AgeI-F | atcggaccggtatgactagcaaaggagaagaac | Sense oligo for amplification of GFP with AgeI site |
| 35 | GFP-XmaI-F | atccgacccgggactagcaaaggagaagaacttttcac | Sense oligo for amplification of GFP with XmaI site and no start codon |
| 36 | GFP-XmaI-R | atccgacccgggtttgtatagttcatccatgcc | Antisense oligo for amplification of GFP with XmaI site and no termination codon |
| 37 | GFP-XhoI-R | cgatcctcgagttatttgtatagttcatccatgcc | Antisense oligo for amplification of GFP with XhoI site |

2.3 Results 2.3.1 pBINPLUS Contains at Least 7.4 kb of Extraneous Sequence

Expression from CPMV-HT enables the production of extremely high levels of recombinant proteins. Nevertheless it was desired to further improve the system and its use for transient transformation.

The first area of improvement relates to the fact that small plasmids are more efficient than larger ones in ligation reactions and bacterial transformation procedures. Comparisons with the structures of smaller binary vectors indicated that pBINPLUS likely contains significant amounts of extraneous sequence. Four elements of pBINPLUS were determined to be essential for proper function as a binary vector: the T-DNA, the RK2 (OriV) broad host range replication origin, the NPTIII gene conferring resistance to kanamycin (Trieu-Cuot and Courvalin, 1983), and TrfA from RK2 that promotes replication (FIG. 9). Bioinformatic analysis of the remaining backbone sections show them to be artefacts of the construction of pBIN19, which relied on the presence of appropriate restriction sites within parent plasmids (Bevan, 1984). These observations are confirmed by a report on the complete sequencing of pBIN19 (Frisch et al., 1995). pBINPLUS includes the non-essential ColEI replication origin for higher copy number in E. coli. Approximately 2.6 kb of superfluous DNA can be found within the T-DNA. This includes the NPTII selectable marker for plant transformation that is not required for transient expression. Overall, the total amount of extraneous sequence within pBINPLUS appears to be in excess of 7.2 kb.

2.3.2 pEAQ Series Construction

Figure 10:
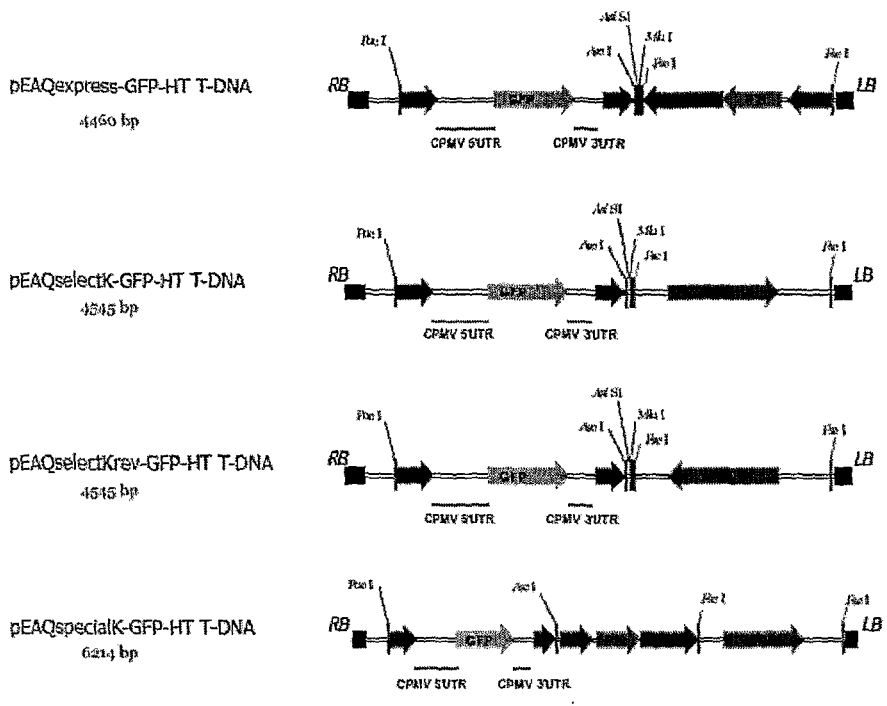
FIG. 10 shows a schematic representation of the T-DNAs of the main pEAQ derivatives. The T-DNAs contain either or both of the P19 and NPTII cassettes as indicated leaving possible cloning into restriction sites as indicated.

In order to monitor the effects on expression resulting from modifications to vector, we chose to start with the pBINPLUS-derived plasmid, pBD-FSC2-512-U162C(HT). Three regions, consisting of the T-DNA, the RK2 (OriV) replication origin, and a segment containing the ColEI origin, NPTIII, and TrfA, were amplified by PCR from pBD-FSC2-GFP-HT. Ligation of these three fragments resulted in the plasmid pEAQbeta (FIG. 9), which is 4584 by smaller than its parent plasmid. A further round of PCR amplification of pEAQbeta removed 2639 by of non-essential sequence from the T-DNA region and inserted three unique restriction sites, AsiSI, MluI, and FseI. AsiSI/MluI digestion is compatible with the insertion of PacI/AscI fragments, and is therefore, extremely useful for cloning multiple cassettes from all previous CPMV cloning vectors. FseI provides a unique 8-base recognition site useful for interchanging different selection markers or silencing suppressor cassettes. The resulting pEAQGFP-HT plasmid is less than half the size of pBINPLUS and without the CPMVHT expression cassette would be only 5137 bp, making it one of the smallest known binary vectors (FIG. 9). The entire pEAQ plasmid was sequenced and it was discovered that the RK2 origin of replication was in the reverse orientation to that previously reported (Frisch et al., 1995) and is therefore indicated in the correct orientation in pEAQ-GFP-HT.

pEAQ-GFP-HT was used as a starting point for the inclusion of various additional features into the T-DNA (FIG. 10). The NPTII cassette from pBINPLUS was re-inserted into the FseI site of pEAQ in both the forward and reverse orientations relative to the GFP-HT cassette to give pEAQselectK-GFP-HT and pEAQselectK(rev)-GFP-HT.

The 35S-P19 cassette was inserted into the FseI site to give pEAQexpress-GFP-HT. Finally, the 35S-P19 cassette was inserted into the MluI/AsiSI sites of pEAQselectK-GFP-HT to give pEAQspecialK-GFP-HT. Thus, a series of small binary vectors for easy and quick transient expression were constructed.

2.3.3 Reduction in Size does not Compromise Transient Expression from pEAQ

Agro-infiltration of the pEAQ series of vectors shows that the large reduction in size does not significantly compromise expression levels in transient assays. Coinfiltration of pEAQ-GFP-HT, and pEAQselectK(rev)-GFP-HT with P19 provided by pBIN61-P19, resulted in levels of expression not significantly different to the co-infiltration of pBD-FSC2-512-HT and P19. This can be seen under UV illumination (FIG. 11A), SDS-PAGE (FIG. 11B), and spectrofluorescence measurements of GFP in protein extracts (FIG. 11C). Interestingly, the orientation of the NPTII cassette within the T-DNA appears to affect expression level. pEAQselectK shows a marked improvement compared to the otherwise identical pEAQselectK(rev), which results in a reduction in GFP accumulation.

Figure 7:
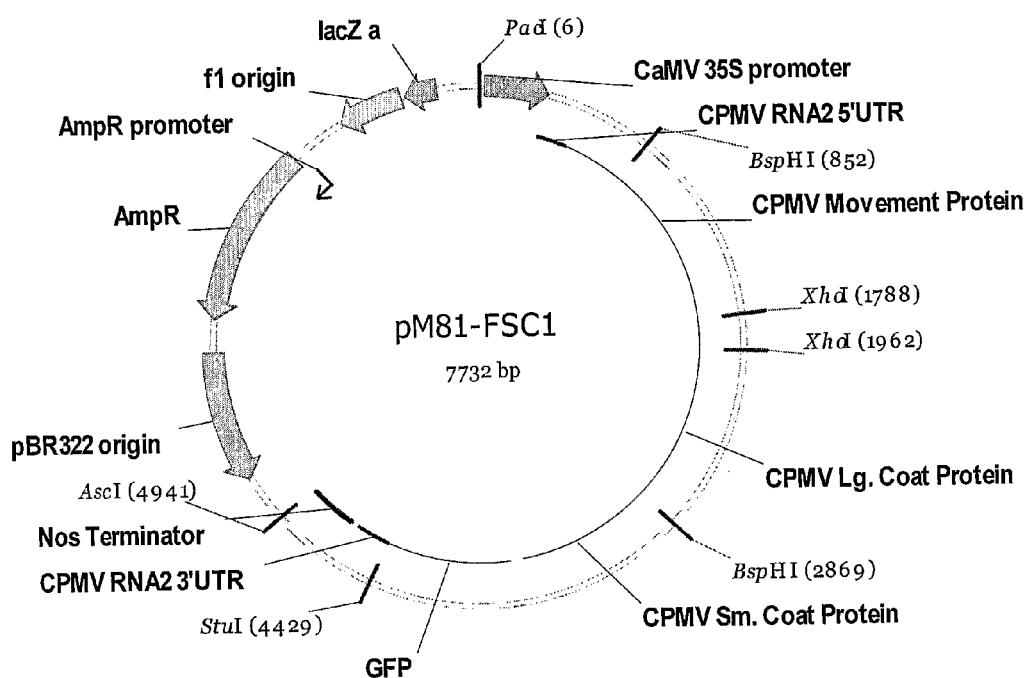
FIG. 7 shows the vector pM81-FSC1.
Figure 8:
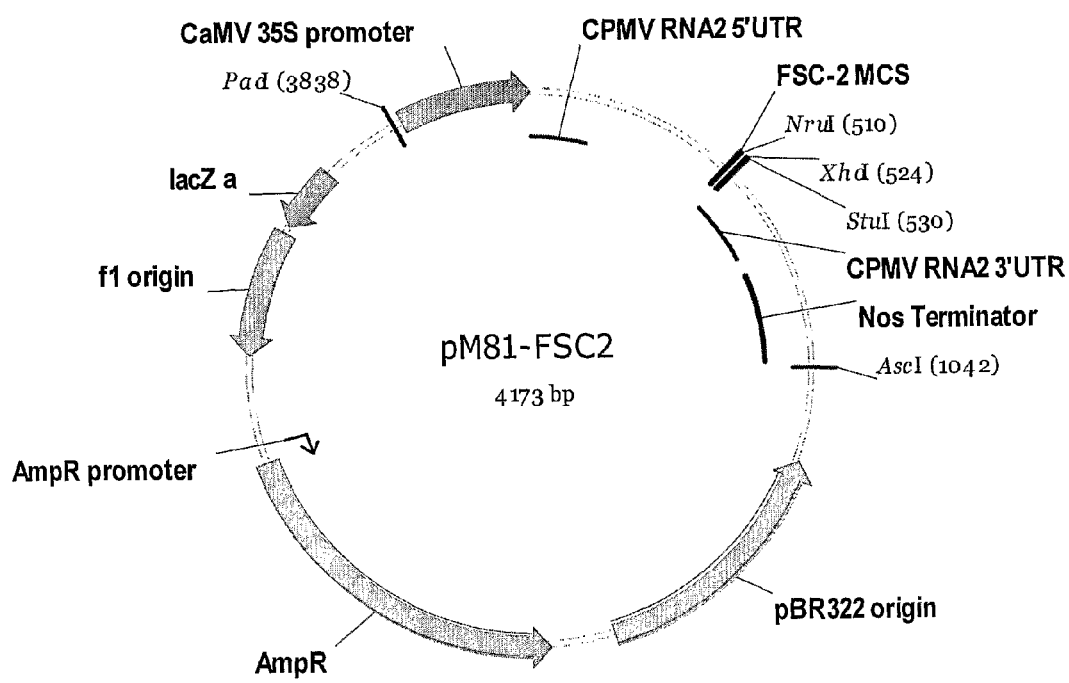
FIG. 8 shows the vector pM81-FSC2.

Theoretically, the incorporation of a suppressor of silencing cassette into pEAQ should not affect its ability to improve transient expression level from a foreign gene to be expressed from the same T-DNA. Indeed, the infiltration of pEAQexpress-GFP-HT alone also resulted in expression levels similar to, or better than, pBD-FSC2-GFP-HT (FIG. 7.3). Furthermore, to test the efficiency of pEAQexpress, the *Agrobacterium* culture was diluted two-fold, such that the final optical density (OD) was that of each individual culture of the coin-filtrations.

Figure 11:
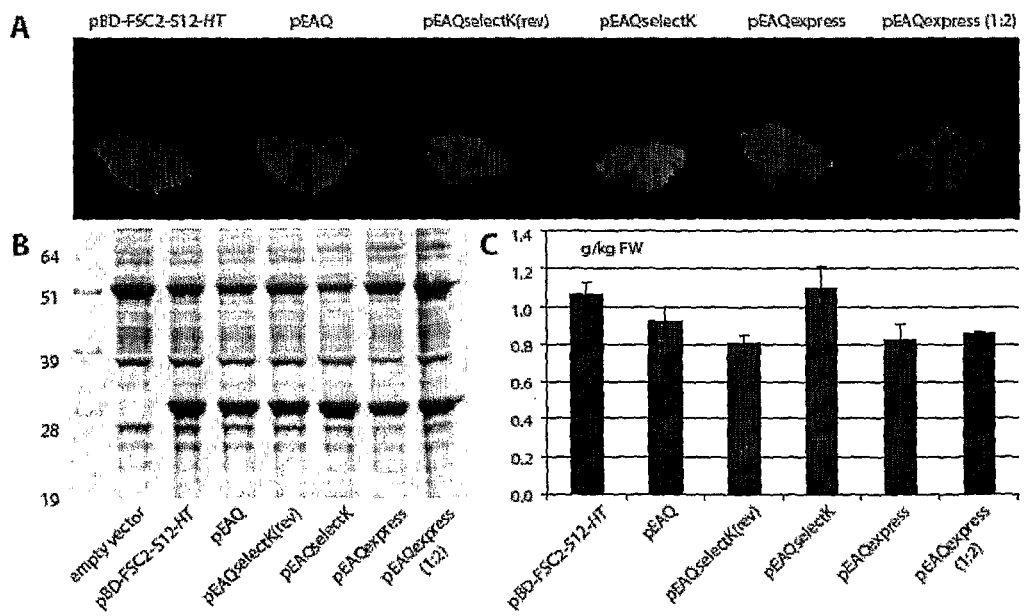
FIG. 11 shows expression levels of GFP generated by pEAQ vectors compared to its parent plasmid pBB-FSC2-512-HT. Tissue was analysed 6 days after infiltration with P19 and the vector indicated except for pEAQexpress, which was infiltrated alone at the standard OD, or at a two-fold dilution. (A) Leaves visualised under UV light, (B) coomassie-stained 12% SDS-PAGE, and (C) spectrofluorometric analysis.

As expected, this resulted in similarly high expression levels and demonstrates that incorporating both the gene of interest and the suppressor of silencing onto the same T-DNA allows the use of half the amount of Agrobacteria (FIG. 11). Therefore, CPMV-HT may be used to express high levels of foreign protein when all components are present on the same T-DNA.

2.3.4 Mutant P19 can Suppress Silencing of a Transgene in a Transient Assay

Figure 12:
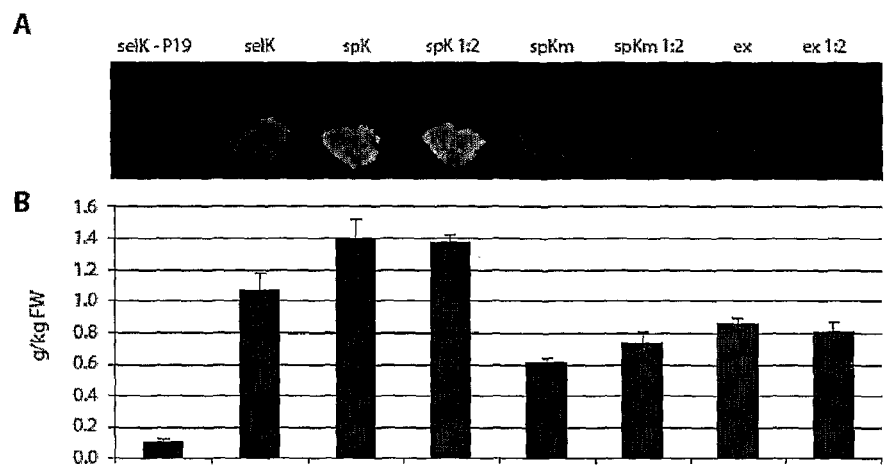
FIG. 12 shows the ability of P19(R43W) to enhance GFP expression compared to wild type P19. Tissue was analysed 6 days after infiltration with pEAQselectK at two-fold dilution (selK-P19), pEAQselectK and P19 (selK), pEAQspecialK (spK), pEAQspecialK at two-fold dilution (spK 1:2), pEAQspecialKm (spKm), pEAQspecialKm at two-fold dilution (spKm 1:2), pEAQexpress (ex), and pEAQexpress at two-fold dilution (ex 1:2). (A) Leaves visualised under UV light and (B) spectrofluorometric analysis.

In order to take advantage of the increase in expression afforded by the forward orientation of the NPTII cassette within the T-DNA, the P19 cassette was inserted between the AsiSI and MluI sites in pEAQselectK-GFP-HT to give pEAQspecialK-GFP-HT (FIG. 10). The presence of P19 on the same T-DNA as the sequence of GFP results in similar levels of expression to pEAQselectK-GFPHT co-infiltrated with P19 (FIG. 12). This is more than the expression generated by pEAQexpress-GFP-HT, and appears to be due to the presence of the NPTII cassette (FIG. 12). On the other hand, the lower expression from pEAQexpress could be due to the different position and orientation of the P19 cassette within the T-DNA. Nevertheless, as with pEAQexpress, pEAQspecialK vectors give high-level expression with Agrobacteria suspensions at half the final OD of that used when two cultures must be co-infiltrated.

Combining the foreign gene expression cassette with a P19 cassette and a selectable marker makes it possible to test the performance of CPMV-HT in transgenic plants. However, the constitutive expression of suppressors of silencing like P19 can result in severe phenotypes due to their interference with endogenous gene silencing associated with developmental processes (Silhavy and Burgyán, 2004). A recently characterised mutation of P19 (R43W) has been proposed to have a reduced activity towards endogenous gene silencing and therefore may be a better candidate for the suppression of transgene silencing in stable transformants (Scholthof, 2007). To investigate the feasibility of stable transformation with the CPMV-HT system, both wt and the mutant P19 were inserted into the T-DNA of pEAQselectK-GFP-HT to assay the variants transiently. As shown by, UV illumination of infiltrated leaves, SDS-PAGE of protein extracts, and spectrofluorometric measurements of GFP levels, the mutant P19 in pEAQspecialKm is approximately half as effective in improving foreign gene expression as the wt P19 in pEAQspecialK (FIG. 12). This represents the first study on the effect of the R43W mutation in P19 on the ability to suppress silencing of a transgene.

Example 3

High Level IgG Expression from a Single Plasmid

Figure 13:
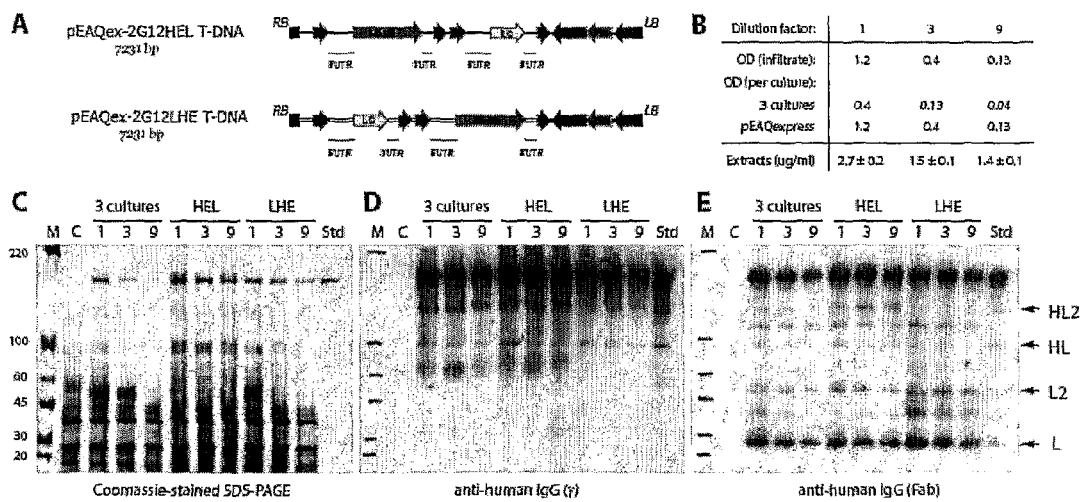
FIG. 13 shows expression of the full size IgG, 2G12, with a single pEAQ plasmid. (A) Schematic representation of the two pEAQexpress-derived plasmids constructed to express 2G12. (B) Infiltration scheme indicating dilutions and their respective ODs for each plasmid combination, and the concentration of protein extracts made after infiltrations at each OD (±SD). (C) Coomassie-stained 12-4% SDS-PAGE analysis and (D) immunological detection of 2G12 heavy (γ) and (E) immunological detection of 2G12 Fab region (Fab) chain 8 days after infiltration. M, marker with sizes indicated; C, control extract; Std, CHO-produced 2G12. For coomassie-staining, protein from the equivalent of 3 mg of infiltrated tissue is loaded in each lane with 1 µg of CHO2G12 and for western blotting the equivalent of 0.75 mg of tissue in each lane with 250 ng of CHO2G12. Estimated assembly/degradation products are indicated.

In order to take advantage of the modular nature of the pEAQ series, CPMV-HT expression cassettes containing the ER-retained heavy chain (HE) and light chain (L) of the human anti-HIV IgG, 2G12 were inserted into the PacI/AscI and AsiSI/MluI sites of pEAQexpress. To determine whether the site of insertion influences expression levels, the L and HE chains were inserted into both positions yielding pEAQex-2G12HEL and pEAQex-2G12LHE (FIG. 13A). Infiltration of *N. benthamiana* with single *Agrobacterium* cultures containing the above plasmids resulted in the formation of fully assembled 2G12 antibodies identical in size to 2G12 produced by mixing three *Agrobacterium* cultures which each expressed the individual components, L, HE and P19 (FIG. 13C). The protein loaded in each lane represents 1/30 of the extract obtained from 90 mg of infiltrated tissue or 1/333 of the protein potentially obtainable from 1 g of tissue. The maximum amount of assembled IgG produced from the 3-strain mixture corresponds to 1 µg of CHO-produced 2G12 on the coomassie-stained non-reduced SDS-PAGE gel. This suggests an expression level of 2G12 in excess of 325 mg/kg of fresh weight tissue, which is in agreement with the SPR-measured concentrations. The use of pEAQex-2G12HEL appears to surpass this already high-level of antibody accumulation.

An advantage of pEAQ-derived vectors is that each component of a multi-chain protein such as an IgG can automatically be delivered to each infected cell. Therefore, high expression levels should be maintained at higher dilutions of Agrobacteria suspensions than if multiple cultures have to be used. To test if this is the case in practice, cultures that were initially resuspended to OD 1.2, and mixed where necessary, were subjected to two serial three-fold dilutions (FIG. 13B). This resulted in final ODs of each individual culture in the three-culture mix being 0.4, 0.13, and 0.04. Single cultures harbouring the pEAQexpress constructs were infiltrated at ODs of 1.2, 0.4, and 0.13. When three separate cultures were used, the level of assembled 2G12 decreases markedly on serial dilution. In contrast, 2G12 expression from pEAQex-2G12HEL and pEAQex-2G12LHE, was maintained at a consistently high level, with any reduction on dilution being very modest (FIG. 13C-E). The lack of sensitivity to dilution confirms the improved efficiency afforded by placing all three expression cassettes on the same T-DNA. Interestingly, the amount of total protein extracted from the infiltrated tissue was almost halved when the OD of the infiltrate was reduced from 1.2 to 0.4. This suggests that a significant fraction of the protein in extracts from tissue in which the higher OD suspension has been infiltrated can consist of Agrobacteria-derived protein or plant proteins produced in response to the higher concentrations of Agrobacteria.

Inspection of FIG. 13C suggests that the relative position of a cassette within the T-DNA can affect the expression levels. The overall expression from pEAQex-2G12LHE was slightly lower than from pEAQex-2G12HEL. This was confirmed by western blotting of the non-reduced samples, which also indicated some differences in the abundance of degradation products and unincorporated immunoglobulin chains (FIG. 13C-E). Tissue infiltrated with pEAQex-2G12LHE appears to lack a heavy chain-specific degradation product of approximately 70 to 80 kDa (FIG. 13D). Also, there appears to be much less of the HL2 assembly intermediate, as well as more free light chain (FIG. 13E). Since, the heavy chain is known to be limiting in 2G12 assembly in plants (Markus Sack, pers. comm., RWTH, Aachen, Germany), which is confirmed by the lack of discernable free heavy chain in all samples, these results indicate that pEAQex-2G12LHE produces less heavy chain than pEAQex-2G12HEL. This could be due to reduced expression from the CPMV-HT cassette closer to the left border of the T-DNA.

In other experiments (data not shown) the CPMV-HT system has also been successfully used in the transient format in *N. benthamiana* to express:

Bluetongue Virus (serotype 10) VP2, VP3, VP5, VP7 and NS1.
Rotavirus NSP5.
Calmodulin from *Medicago truncatula* (which was subsequently purified).
The difficult-to-express ectodomain of human Fc gamma receptor 1 (CD64)—which has been purified and shown to be functional in antibody binding studies.
The CPMV Small (S) and Large (L) coat proteins were co-expressed and shown to assemble into virus-like particles (data not shown)

Example 4

Direct Cloning into a CPMV-HT Expression Vector

Although combining elements of the system on to a single plasmid, the vectors described hereinbefore still required a two-step cloning procedure to introduce a sequence to be expressed into the binary plasmid. The present example provides a binary plasmid into which a gene of interest could be directly inserted. The plasmid incorporates a polylinker that not only permits direct insertion into the pEAQ-based plasmid, but also permits the fusion of a C- or N-terminal histidine tag if desired (pEAQ-HT; FIG. 14A). The polylinker was first inserted as annealed oligonucleotides into pM81-FSC2-512 (A115G)(U162C) giving pM81-FSC-POW. This construct can still be used for the standard two-step cloning procedure for the generation pEAQ-based constructs for the expression of multiple polypeptides. Furthermore, use of the double mutated 5' leader may enable even higher expression levels to be obtained than is possible with the single mutation. The CPMV-HT cassette was then transferred into pEAQspecialK via the PacI/AscI sites to give pEAQ-HT. Insertion of GFP into all three positions within the polylinker of pEAQ-HT resulted in an un-tagged GFP, and 5' (HisGFP) and 3' (GFPHis) His-tag fusions.

As expected, untagged GFP was expressed to a level even higher than that obtained with pEAQspecialK-GFP-HT and in excess of 1.6 g/kg FW tissue (FIG. 14B). This is likely due to the fact that the CPMV 5' leader of pEAQ-HT contains the extra mutation which removes AUG 115 which, when removed in addition to AUG 161, further enhances expression.

The presence of the His-tag as detected by western blotting confirmed the correct fusion at both the N- and C-terminus of the amino acid residues encoded by the polylinker. All three GFP variants were detectable with anti-GFP antibodies whereas only HisGFP and GFPHis were detectable with anti-His antibodies (FIG. 14C), and the presence of the His-tag reduced the mobility of the GFP band in SDS-PAGE by the expected amount. The tag also reduced the amount of GFP detected by the analysis of fluorescence (FIG. 14B). This effect was more pronounced for N-terminal His tag. The intensity of the coomassie-stained bands suggests that this represents a reduction in tagged GFP accumulation (FIG. 14C), rather than interference with the fluorogenic properties of GFP. Nevertheless, the levels of the His-tagged proteins were still very high yielding in excess of 0.6 and 1.0 g of GFP per kg FW tissue.

Discussion of Examples 2-4

To improve the ease of use and performance of the CPMV-HT expression system, a modular set of vectors has been created for easy and quick plant expression.

Removing more than half of the plasmid backbone from the binary vector, pBINPLUS, and some of the T-DNA region not essential for transient expression resulted in one of the smallest binary Ti plasmids known with no compromise on expression levels.

A similar proportion of the backbone had previously been removed from pBIN19 without a loss of performance (Xiang et al., 1999). However, pBINPLUS possesses two significant improvements over pBIN19 (van Engelen et al., 1995); an increased copy number in *E. coli* owing to the addition of the ColEI origin of replication and a reoriented T-DNA ensuring the gene of interest is further from the left border that can suffer extensive deletions in planta (Rossi et al., 1996). While the smaller size of pEAQ plasmids had no noticeable effect on their copy number, they give greatly improved yields during cloning procedures using commercial plasmids extraction kits as these are most efficient for plasmids below 10 kb (data not shown).

The modular nature of the pEAQ binary vector adds functionality to CPMV-HT expression by allowing any silencing suppressor and/or marker gene, if required, to be co-expressed with one or two CPMV-HT cassettes. For example, insertion of a second HT cassette containing a heterologous sequence into the AsiSI/MluI sites of pEAQexpress-GFP-HT would allow tracking of expression with GFP fluorescence.

Furthermore, the flexibility of the vectors simplifies the system for transient expression by only requiring the infiltration of a single *Agrobacterium* construct, and improves efficiency by reducing the amount of infiltrate required in proportion to the number of expression cassettes present within the T-DNA. With P19 occupying the FseI site, the presence of two cloning sites for accepting HT cassettes from cloning vectors (such as pM81-FSC2-U162C) also allows even more efficient expression of multi-subunit proteins such as full-size antibodies.

The effect of P19 on enhancing expression levels of transgenes is well characterised (Voinnet et al., 2003). However, this study presents the first demonstration of its effectiveness when co-delivered to each cell on the same TDNA. A previous study has reported the co-delivery of P19 from a separate TDNA within the same *Agrobacterium* as the transgene-containing T-DNA (Hellens et al., 2005). However, there was no effect of P19 until 6 days after infiltration, suggesting inefficient transfer of T-DNA. The present study also demonstrates the first use of the R43W mutant P19 to enhance the expression of a transgene. The finding that the mutant was about half as effective in enhancing the expression of GFP as wt P19 agrees with its known reduction in activity, which compromises both the infectivity of TBSV (Chu et al., 2000), and the ability of the protein to bind the smaller class (21-22 nts) of short interfering RNAs (Omarov et al., 2006). However, it is possible that this feature potentially makes the R43W mutant more suitable for applications involving stable transformation. The micro RNAs associated with development are also in the smaller size class (Vaucheret, 2006; Zhang et al., 2006) and, therefore, developmental processes may not be as severely affected by the presence of the mutant P19 as they would by the wt version (Scholthof, 2007). Furthermore, the mutant may provide a way of controlling the transient expression of potentially cytotoxic foreign proteins.

The expression of 2G12 from a single plasmid represents the highest reported yield of an antibody from plant tissue infiltrated with a single *Agrobacterium* culture. Apart from using 3 *Agrobacterium* cultures for CPMV-HT expression, the only way of achieving similar levels with another system involved the infiltration of 6 separate cultures and a virus vector approach (Giritch et al., 2006). Furthermore, the use of a single plasmid affords a reduction in the amount of bacteria needed to ensure co-delivery of multiple expression cassettes, which would provide a significant cost saving at industrial production levels. The infiltration process is also physically easier to carry out with more dilute cultures due to less clogging of the intercellular spaces of leaf tissue. In addition, the dilution to a total OD of 0.4 reduced the amount of infiltration-derived protein contaminants. Analysis of nine separate infiltrations at each OD showed a reduction in the protein concentrations of the extracts from 2.7±0.2 to 1.5±0.1 mg/ml when the OD of the cultures was reduced from 1.2 to 0.4. Since the use of pEAQexpress generates as much 2G12 at OD 0.4 as the three-culture system does at an infiltrate OD of 1.2, the recombinant target protein must be purified from only half the amount of contaminating protein using pEAQexpress. This provides a very useful and unexpected advantage for downstream processing. Expression of 2G12 from pEAQexpress also indicates an effect of position of an expression cassette within the T-DNA of pEAQ vectors on the level of expression obtained. The increase in free light chain accumulation from pEAQex-2G12LHE suggests that less heavy chain is expressed with this construct, which appears to result in less assembled antibody. This could be due to the arrangement of expression cassettes on the T-DNA. Alternatively, a proportion of the T-DNAs are susceptible to nucleolytic degradation at the left border (Rossi et al., 1996). The reinsertion of the NPTII cassette within the T-DNA appeared to have a marked effect on expression depending on its orientation. During cloning manipulations it became apparent that pEAQselectK-GFP-HT reached a plasmid copy number in *E. coli* of approximately 1.5 times that of pEAQselectK(rev)-GFP-HT (determined from yield measurements of three separate plasmid preparations performed with the QIAprep kit, QIAGEN). This loosely correlates to the difference in expression levels observed between the two vectors. It is not known what contributes to the increased copy number, or indeed whether the difference also exists when the plasmids are transferred to Agrobacteria. However, these observations suggest that plasmid copy number may be an important for efficient *Agrobacterium* mediated transient expression. In this respect, the use of the RK2 origin (oriV in FIG. 9) by pBIN19 and its derivatives makes it a good choice for transient expression as RK2 plasmids are known to accumulate to 7 to 10 copies in *Agrobacterium* (Veluthambi et al., 1987). This is similar to the pVS1 origin utilised by pPZP and about 2-5 times higher than is generated by the pSa origin (Lee and Gelvin, 2008), which is present in the widely used pGREEN binary vector (Helens et al., 2000). Plasmids containing replication origins that yield higher copy numbers such as pRi-based plasmids (Lee and Gelvin, 2008) may be even better suited to transient expression.

To make high-level expression with pEAQ vectors easily accessible for labs with no previous experience with CPMV-based expression or indeed, plant-based expression in general, a direct cloning version of pEAQ was created. This was achieved by inserting a polylinker between the 5' leader and 3' UTRs of a CPMVHT expression cassette, which was the positioned on a T-DNA which also contained P19 and NPTII cassettes. The NPTII cassette was included because its presence appeared to appreciably enhance expression (see above). The polylinker also encodes two sets of 6× Histidine residues to allow the fusion of N- or C terminal His-tags to facilitate protein purification. The resulting constructs also benefit from the second mutation in the 5' leader which enhances expression relative to HT.

These enhanced expression cassettes may also be subcloned from the cloning vector pM81-FSC-POW into any pEAQ plasmid. The use of pEAQHT led to increased GFP expression compared with pEAQspecialK, which contains just the single mutation (U162C). Furthermore, the polylinker design also allowed the expression of His-tagged variants using a one step cloning procedure. The modular binary vectors presented here are specifically designed for, but not restricted to, use with CPMV-HT expression. Extremely high-level expression has been coupled with improved cloning efficiency and ease of use. The system provides the most effective and straightforward method for transient expression of value-added proteins in plants without the complications of viral amplification. It allows milligram quantities of recombinant protein within two weeks of sequence identification in any molecular biology lab with access to plant growth facilities. Therefore, it is anticipated that it will provide an extremely valuable tool in both academic and industrial settings.

Example 5

Stable Integration with pEAQ Plasmids and Transgenic Plants

Although the pEAQ vector series was designed with transient expression in mind, the reinsertion of the NPTII cassette into the T-DNA to provides a selectable marker for genome integration. This potentially allows these smaller and more useful binary vectors to be used for stable plant and plant cell culture transformation. When used to transform *N. benthamiana* leaf discs, pEAQ vectors containing the NPTII cassette within the T-DNA were able to induce callus formation under selection with the same efficiency as pBINPLUS-based constructs. Furthermore, GFP expression was detectable in these tissues under UV light (data not shown. This demonstrates that multi-cassette T-DNA molecules from pEAQ vectors can stably integrate into the plant genome and drive the expression of foreign genes.

Fluorescent plants have also been regenerated. The leaves of the primary transformants ($T_0$) were fluorescent under uv light indicating high levels of GFP expression. The seed from the self-fertilised $T_0$ plants were viable, and the resulting $T_1$ seedlings harbouring the transgene are also fluorescent (results not shown).

Example 6

Use of the CPMV-Based HT System with Baculovirus Vectors

FIG. 15 shows a construct suitable for utilising the CPMV-based HT system with baculovirus vectors in insect cells. Under control of the p10 promoter, the HyperTrans CPMV RNA-2 UTRs also enhance the expression of GFP in insect cells using the Baculovirus expression system. An approximately 5-fold enhancement of fluorescence levels in baculovirus-infected sf21 cells, as measured by flow cytometry, was obtained in comparison to a construct without the CPMV-HT cassette.

REFERENCES

Alamillo, J. M., Monger, W., Sola, I., García, B., Perrin, Y., Bestagno, M., Burrone, O. R., Plana-Duran, J., Enjuanes, L., Lomonossoff, P. G. and García, J. A. (2006) Use of virus vectors for the expression in plants of active full-length and single chain anticoronavirus antibodies. *Biotechnol. J.* 1, 1103-1111.

Brigneti, G., Voinnet, O., Li, W. X., Ji, L. H., Ding, S. W and Baulcombe, D. C. (1998) Viral pathogenicity determinants are suppressors of transgene silencing in *Nicotiana benthamiana*. EMBO Journal 17: 6739-6746.

Cañizares, M. C., Liu, L, Perrin, Y., Tsakiris, E. and Lomonossoff, G. P. (2006). A bipartite system for the constitutive and inducible expression of high levels of foreign proteins in plants. *Plant Biotechnol. J.* 4, 183-193.

Gopinath, K., Wellink, J., Porta, C., Taylor, K. M., Lomonossoff, G. P. and van Kammen, A. (2000) Engineering cowpea mosaic virus RNA-2 into a vector to express heterologous proteins in plants. Virology 267: 159-173.

Holness, C. L., Lomonossoff, G. P., Evans, D. and Maule, A. J. (1989). Identification of the initiation codons for translation of cowpea mosaic virus middle component RNA using site directed mutagenesis of an infectious cDNA clone. Virology 172, 311 320.

Liu, L. and Lomonossoff, G. P. (2002) Agroinfection as a rapid method for propagating Cowpea mosaic virus-based constructs. *J. Virol. Methods* 105, 343-348.

Liu, L. and Lomonossoff, G. P. (2006) A site-directed mutagenesis method utilising large double-stranded DNA templates for the simultaneous introduction of multiple changes and sequential multiple rounds of mutation: Application to the study of whole viral genomes. *J. Virol. Methods* 137, 63-71.

Liu, L., Canizares, M. C., Monger, W., Perrin, Y., Tsakiris, E., Porta, C., Shariat, N., Nicholson, L. and Lomonossoff, G. P. (2005). Cowpea mosaic virus-based systems for the production of antigens and antibodies in plants. *Vaccine* 23, 1788-1792.

Lomonossoff, G. P. & Shanks, M. (1983). The nucleotide sequence of cowpea mosaic virus B RNA. *EMBO Journal* 2, 2253-2258.

Mechtcheriakova, L A., Eldarov, M. A., Nicholson, L., Shanks, M., Skryabin, K. G. and Lomonossoff, G. P. (2006) The use of viral vectors to produce hepatitis B virus core particles in plants. *J. Virol. Methods* 131, 10-15.

Monger, W., Alamillo, J. M., Sola, I, Perrin, Y., Bestagno, M., Burrone, O. R., Sabella, P., Plana-Duran, J., Enjuanes, L., Garcia, J. A. and Lomonossoff, G. P. (2006) An antibody derivative expressed from viral vectors passively immunizes pigs against transmissible gastroenteritis virus infection when supplied orally in crude plant extracts. *Plant Biotechnol. J.* 4, 623-631.

Rohll, J. B., Holness, C. L., Lomonossoff, G. P. and Maule, A. J. (1993). 3' terminal nucleotide sequences important for the accumulation of cowpea mosaic virus M-RNA. Virology 193, 672-679.

Sainsbury, F., Lavoie, P-O., D'Aoust, M-A., Vezina, L-P. and Lomonossoff, G. P. (2008). Expression of Multiple Proteins Using Full-Length and Deleted Versions of Cowpea Mosaic Virus RNA-2. *Plant Biotechnology Journal*, 6: 82-92.

Sainsbury, F., Cañizares, M. C. and Lomonossoff, G. P. (2007) Cowpea mosaic virus-based expression vectors. In: *Virus Expression Vectors* (Hefferon, K. ed), pp. 339-555. Kerala, India: Transworld Research Network.

Sainsbury, F. and Lomonossoff, G. P. (2008). Extremely high-level and rapid transient protein production in plants without the use of viral replication. *Plant Physiology* 148, 1212-1218.

Sainsbury, F., Liu, L. and Lomonossoff G. P. (2009) Cowpea mosaic virus-based expression of antigens and antibodies in plants. In: *Methods in Molecular Biology* Vol. 483: *Recombinant Pharmaceutical Proteins from Plants* (Faye, L. and Gomord, V. eds), pp 25-39, NY: Humana Press.

van Bokhoven, H., Le Gall, O, Kasteel, D., Verver, J., Wellink, J. and van Kammen, A. (1993). Cis- and Trans-acting Elements in Cowpea Mosaic Virus RNA Replication. Virology 195, 377-386.

Wellink J, Verver J, van Kammen A. (1993). Mutational analysis of AUG codons of cowpea mosaic virus M RNA. Biochimie. 75(8):741-7.

ADDITIONAL REFERENCES

Lee L Y, Gelvin S B (2008) T-DNA binary vectors and systems. Plant Physiology 146: 325-332

Hajdukiewicz P, Svab Z, Mange P (1994) The small, versatile pPZP family of *Agrobacterium* binary vectors for plant transformation. Plant Molecular Biology 25: 989-994

Hellens R, Mullineaux P, Klee H (2000b) A guide to *Agrobacterium* binary Ti vectors. Trends in Plant Science 5: 446-451

Hiei Y, Ohta S, Komari T, Kumashiro T (1994) Efficient transformation of rice (*Oryza-sativa* L) mediated by *Agrobacterium* and sequence-analysis of the boundaries of the T-DNA. Plant Journal 6: 271-282

Veluthambi K, Jayaswal R K, Gelvin S B (1987) Virulence genes-a, gene-G, and gene-D mediate the double-stranded border cleavage of T-DNA from the *Agrobacterium* Ti plasmid. Proceedings of the National Academy of Sciences of the United States of America 84: 1881-1885

Thole V, Worland B, Snape J W, Vain P (2007) The pCLEAN dual binary vector system for *Agrobacterium*-Mediated plant transformation. Plant Physiology 145: 1211-1219

Johansen L K, Carrington J C (2001) Silencing on the spot. Induction and suppression of RNA silencing in the *Agrobacterium*-mediated transient expression system. Plant Physiology 126: 930-938

Janssen B J, Gardner R C (1989) Localized transient expression of Gus in leaf-disks following cocultivation with *Agrobacterium*. Plant Molecular Biology 14: 61-72

Narasimhulu S B, Deng X, Sarria R, Gelvin S B (1996) Early transcription of *Agrobacterium* T-DNA genes in tobacco and maize. Plant Cell 8: 873-886

Hellens R P, Edwards E A, Leyland N R, Bean S, Mullineaux P M (2000a) pGreen: a versatile and flexible binary Ti vector for *Agrobacterium*-mediated plant transformation. Plant Molecular Biology 42: 819-832

Tzfira T, Tian G W, Lacroix B, Vyas S, Li J X, Leitner-Dagan Y, Krichevsky A, Taylor T, Vainstein A, Citovsky V (2005) pSAT vectors: a modular series of plasmids for autofluorescent protein tagging and expression of multiple genes in plants. Plant Molecular Biology 57: 503-516

Voinnet O, Rivas S, Mestre P, Baulcombe D (2003) An enhanced transient expression system in plants based on suppression of gene silencing by the p19 protein of tomato bushy stunt virus. Plant Journal 33: 949-956

Frisch D A, Harrishaller L W, Yokubaitis N T, Thomas T L, Hardin S H, Hall T C (1995) Complete sequence of the binary vector BIN-19. Plant Molecular Biology 27: 405-409

Trieu-cuot P, Courvalin P (1983) Nucleotide-sequence of the *Streptococcus*-faecalis plasmid gene encoding the 3′5″-Aminoglycoside phosphotransferase type-III. Gene 23: 331-341

Bevan M (1984) Binary *Agrobacterium* vectors for plant transformation. Nucleic Acids Research 12: 8711-8721

Silhavy D, Burgyan J (2004) Effects and side-effects of viral RNA silencing suppressors on short RNAs. Trends in Plant Science 9: 76-83

Schoithof H B (2007) Heterologous expression of viral RNA interference suppressors: RISC management. Plant Physiology 145: 1110-1117 van Engelen F A, Molthoff J W, Conner A J, Nap J P, Pereira A, Stiekema W J (1995) pBINPLUS—an improved plant transformation vector based on pBIN19. Transgenic Research 4: 288-290

Rossi L, Hohn B, Tinland B (1996) Integration of complete transferred DNA units is dependent on the activity of virulence E2 protein of *Agrobacterium tumefaciens*. Proceedings of the National Academy of Sciences of the United States of America 93: 126-130

Xiang C B, Han P, Lutziger I, Wang K, Oliver D J (1999) A mini binary vector series for plant transformation. Plant Molecular Biology 40: 711-717

Hellens R P, Allan A C, Friel E N, Bolitho K, Grafton K, Templeton M D, Karunairetnam S, Gleave A P, Laing W A (2005) Transient expression vectors for functional genomics, quantification of promoter activity and RNA silencing in plants. Plant Methods 1: 13

Chu M, Desvoyes B, Turina M, Noad R, Scholthof H B (2000) Genetic dissection of tomato bushy stunt virus p19-protein-mediated host-dependent symptom induction and systemic invasion. Virology 266: 79-87

Omarov R, Sparks K, Smith L, Zindovic J, Scholthof H B (2006) Biological relevance of a stable biochemical interaction between the tombusvirus-encoded P19 and short interfering RNAs. Journal of Virology 80: 3000-3008

Vaucheret H (2006) Post-transcriptional small RNA pathways in plants: mechanisms and regulations. Genes & Development 20: 759-771

Zhang B H, Pan X P, Cobb G P, Anderson T A (2006) Plant microRNA: A small regulatory molecule with big impact. Developmental Biology 289: 3-16

Giritch A, Marillonnet S, Engler C, van Eldik G, Botterman J, Klimyuk V, Gleba Y (2006) Rapid high-yield expression of full-size IgG antibodies in plants coinfected with noncompeting viral vectors. Proceedings of the National Academy of Sciences of the United States of America 103: 14701-14706

TABLE 1

SEQ ID NO: 1
The complete CPMV RNA-2 genome segment
(nucleotides 1 to 3481)

```
  1 tattaaaatc ttaataggtt ttgataaaag cgaacgtggg gaaacccgaa ccaaaccttc 61 ttctaaattc tctctcatct ctcttaaagc aaacttctct cttgtctttc ttgcatgagc 121 gatcttcaac gttgtcagat cgtgcttcgg caccagtaca atgttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt 361 gacgaggtat tgttgcctgt acttcttcct tcttcttctt gctgattggt tctataagaa 421 atctagtatt ttctttgaaa cagagttttc ccgtggtttt cgaacttgga gaaagattgt 481 taagcttctg tatattctgc ccaaatttga aatggaaagc attatgagcc gtggtattcc 541 ttcaggaatt ttggaggaaa aagctattca gttcaaacgt gccaaagaag ggaataaacc 601 cttgaaggat gagattccca agcctgagga tatgtatgtg tctcacactt ctaaatggaa 661 tgtgctcaga aaaatgagcc aaaagactgt ggatctttcc aaagcagctg ctgggatggg
```

TABLE 1-continued

SEQ ID NO: 1
The complete CPMV RNA-2 genome segment
(nucleotides 1 to 3481)

```
 721 attcatcaat aagcatatgc ttacgggcaa catcttggca caaccaacaa cagtcttgga
 781 tattcccgtc acaaaggata aaacacttgc gatggccagt gattttattc gtaaggagaa
 841 tctcaagact tctgccattc acattggagc aattgagatt attatccaga gctttgcttc
 901 ccctgaaagt gatttgatgg gaggcttttt gcttgtggat tctttacaca ctgatacagc
 961 taatgctatt cgtagcattt tgttgctcc aatgcgggga ggaagaccag tcagagtggt
1021 gaccttccca aatacactgg cacctgtatc atgtgatctg aacaatagat tcaagctcat
1081 ttgctcattg ccaaactgtg atattgtcca gggtagccaa gtagcagaag tgagtgtaaa
1141 tgttgcagga tgtgctactt ccatagagaa atctcacacc ccttcccaat gtatacaga
1201 ggaatttgaa aaggagggtg ctgttgttgt agaatactta ggcagacaga cctattgtgc
1261 tcagcctagc aatttaccca cagaagaaaa acttcggtcc cttaagtttg actttcatgt
1321 tgaacaacca agtgtcctga agttatccaa ttcctgcaat gcgcactttg tcaagggaga
1381 aagtttgaaa tactctatttt ctggcaaaga agcagaaaac catgcagttc atgctactgt
1441 ggtctctcga gaaggggctt ctgcggcacc caagcaatat gatcctattt tgggacgggt
1501 gctggatcca cgaaatggga atgtggcttt tccacaaatg gagcaaaact tgtttgccct
1561 ttctttggat gatacaagct cagttcgtgg ttctttgctt gacacaaaat tcgcacaaac
1621 tcgagttttg ttgtccaagg ctatggctgg tggtgatgtg ttattggatg agtatctcta
1681 tgatgtggtc aatggacaag attttagagc tactgtcgct tttttgcgca cccatgttat
1741 aacaggcaaa ataaaggtga cagctaccac caacatttct gacaactcgg gttgttgttt
1801 gatgttggcc ataaatagtg gtgtgagggg taagtatagt actgatgttt atactatctg
1861 ctctcaagac tccatgacgt ggaacccagg gtgcaaaaag aacttctcgt tcacatttaa
1921 tccaaaccct tgtgggggatt cttggtctgc tgagatgata agtcgaagca gagttaggat
1981 gacagttatt tgtgtttcgg gatggacctt atctcctacc acagatgtga ttgccaagct
2041 agactggtca attgtcaatg agaaatgtga gcccaccatt taccacttgg ctgattgtca
2101 gaattggtta ccccttaatc gttggatggg aaaattgact tttccccagg gtgtgacaag
2161 tgaggttcga aggatgcctc tttctatagg aggcggtgct ggtgcgactc aagctttctt
2221 ggccaatatg cccaattcat ggatatcaat gtggagatat tttagaggtg aacttcactt
2281 tgaagttact aaaatgagct ctccatatat taaagccact gttacatttc tcatagcttt
2341 tggtaatctt agtgatgcct ttggttttta tgagagtttt cctcatagaa ttgttcaatt
2401 tgctgaggtt gaggaaaaat gtactttggt tttctcccaa caagagtttg tcactgcttg
2461 gtcaacacaa gtaaacccca gaaccacact tgaagcagat ggttgtccct acctatatgc
2521 aattattcat gatagtacaa caggtacaat ctccggagat tttaatcttg gggtcaagct
2581 tgttggcatt aaggattttt gtggtatagg ttctaatccg ggtattgatg gttcccgctt
2641 gcttggagct atagcacaag gacctgtttg tgctgaagcc tcagatgtgt atagcccatg
2701 tatgatagct agcactcctc ctgctccatt ttcagacgtt acagcagtaa cttttgactt
2761 aatcaacggc aaaataactc ctgttggtga tgacaattgg aatacgcaca tttataatcc
2821 tccaattatg aatgtcttgc gtactgctgc ttggaaatct ggaactattc atgttcaact
2881 taatgttagg ggtgctggtg tcaaaagagc agattgggat ggtcaagtct tgtttacctt
2941 gcgccagtcc atgaaccctg aaagttatga tgcgcggaca tttgtgatct cacaacctgg
```

TABLE 1-continued

SEQ ID NO: 1
The complete CPMV RNA-2 genome segment
(nucleotides 1 to 3481)

```
3001 ttctgccatg ttgaacttct cttttgatat catagggccg aatagcggat ttgaatttgc 3061 cgaaagccca tgggccaatc agaccacctg gtatcttgaa tgtgttgcta ccaatcccag 3121 acaaatacag caatttgagg tcaacatgcg cttcgatcct aatttcaggg ttgccggcaa 3181 tatcctgatg cccccatttc cactgtcaac ggaaactcca ccgttattaa agtttaggtt 3241 tcgggatatt gaacgctcca agcgtagtgt tatggttgga cacactgcta ctgctgctta 3301 actctggttt cattaaattt tctttagttt gaatttactg ttatttggtg tgcatttcta 3361 tgtttggtga gcggttttct gtgctcagag tgtgtttatt ttatgtaatt taatttcttt 3421 gtgagctcct gtttagcagg tcgtcccttc agcaaggaca caaaaagatt ttaattttat 3481 t
```

The start codons at positions 115, 161, 512 and 524 of the CPMV RNA-2 genome segment are shown in bold and underlined.

TABLE 2

Oligonucleotides used in the mutagenesis of the 5' region of pM81-FSC-2 clones

| SEQ ID NO: | Oligo-nucleotide | Sequence | Mutation |
|---|---|---|---|
| 2 | A115G-F | CTTGTCTTTCTTGCGTGAGCGATCTTCAACG | Removes AUG (→GUG) at 115 eliminating translation from uORF |
| 3 | A115G-R | CGTTGAAGATCGCTCACGCAAGAAAGACAAG | |
| 4 | U162C-F | GGCACCAGTACAACGTTTTCTTTCACTGAAGCG | Removes AUG(→ACG) at 161 eliminating translation from AUG 161 while maintaining amino acid sequence of uORF |
| 5 | U162C-R | CGCTTCAGTGAAAGAAAACGTTGTACTGGTGCC | |

The mutant nucleotide of the oligonucleotides used in the mutagenesis of the 5' region of pM81-FSC-2 clones are shown in bold

TABLE 3

| SEQ ID NO: 6 | CPMV wt sequence from Table 1 | tatattctgc ccaaatttga aatggaaagc att atgagcc gtggtattcc |
| --- | --- | --- |
| SEQ ID NO: 7 | Mutated sequence in pM81-FSC-1 | tatattctgc ccaaatttgT CatgAaaagc att atgagcc gtggtattcc<br>509<br>BspH1 |
| SEQ ID NO: 8 | Mutated sequence in pM81-FSC-2 | tatattctgc ccaaattCGC GACGATCGTA CTCTCGAGGC CT<br>507<br>Nru1         Xho1 |

Nucleotide differences between the sequence of the pM81-FSC-1 and pM81-FSC-2 vectors and the CPMV wt sequence from Table 1 and are shown as capital letters.

Nucleotide Sequence of pM81-FSC-1
SEQ ID NO: 9

LOCUS pM81-FSC1 7732 bp DNA circular 10-OCT-2007

| FEATURES | Location/Qualifiers |
| --- | --- |
| 5'UTR | 342 . . . 501<br>/vntifkey = "52"<br>/label = CPMV\RNA2\5'UTR |
| promoter | 27 . . . 341<br>/vntifkey = "29"<br>/label = CaMV\35S\promoter |
| terminator | 4669 . . . 4921<br>/vntifkey = "43"<br>/label = Nos\Terminator |
| mat_peptide | 3712 . . . 4422<br>/vntifkey = "84"<br>/label = GFP |
| 3'UTR | 4432 . . . 4615<br>/vntifkey = "50"<br>/label = CPMV\RNA2\3'UTR |
| CDS | complement(5944 . . . 6804)<br>/vntifkey = "4"<br>/label = AmpR |
| misc_feature | complement(7391 . . . 7546)<br>/vntifkey = "21"<br>/label = lacZ_a |
| promoter | complement(6846 . . . 6874)<br>/vntifkey = "30"<br>/label = AmpR\promoter |
| rep_origin | complement(7067 . . . 7373)<br>/vntifkey = "33"<br>/label = f1_origin |
| rep_origin | complement(5170 . . . 5789)<br>/vntifkey = "33"<br>/label = pBR322_origin |
| mat_peptide | 502 . . . 1878<br>/vntifkey = "84"<br>/label = CPMV\Movement\Protein |
| mat_peptide | 1879 . . . 2999<br>/vntifkey = "84"<br>/label = CPMV\Lg.\Coat\Protein |
| mat_peptide | 3000 . . . 3638<br>/vntifkey = "84"<br>/label = CPMV\Sm.\Coat\Protein |

BASE COUNT 2105 a 1682 c 1770 g 2175 t
ORIGIN

```
  1 ttaattaaga attcgagctc caccgcggaa acctcctcgg attccattgc ccagctatct
 61 gtcactttat tgagaagata gtggaaaagg aaggtggctc ctacaaatgc catcattgcg
121 ataaaggaaa ggccatcgtt gaagatgcct ctgccgacag tggtcccaaa gatggacccc
181 cacccacgag gagcatcgtg gaaaaagaag acgttccaac cacgtcttca aagcaagtgg
241 attgatgtga tatctccact gacgtaaggg atgacgcaca atcccactat ccttcgcaag
301 acccttcctc tatataagga agttcatttc atttggagag gtattaaaat cttaataggt
361 tttgataaaa gcgaacgtgg ggaaacccga accaaacctt cttctaaact ctctctcatc
421 tctcttaaag caaacttctc tcttgtcttt cttgcatgag cgatcttcaa cgttgtcaga
481 tcgtgcttcg gcaccagtac aatgttttct ttcactgaag cgaaatcaaa gatctctttg
```

| Nucleotide Sequence of pM81-FSC-1 SEQ ID NO: 9 |
| --- |

```
 541 tggacacgta gtgcggcgcc attaaataac gtgtacttgt cctattcttg tcggtgtggt
 601 cttgggaaaa gaaagcttgc tggaggctgc tgttcagccc catacattac ttgttacgat
 661 tctgctgact ttcggcgggt gcaatatctc tacttctgct tgacgaggta ttgttgcctg
 721 tacttcttc ttcttcttct tgctgattgg ttctataaga aatctagtat tttctttgaa
 781 acagagtttt cccgtggttt tcgaacttgg agaaagattg ttaagcttct gtatattctg
 841 cccaaatttg tcatgaaaag cattatgagc cgtggtattc cttcaggaat tttggaggaa
 901 aaagctattc agttcaaacg tgccaaagaa gggaataaac ccttgaagga tgagattccc
 961 aagcctgagg atatgtatgt gtctcacact tctaaatgga atgtgctcag aaaaatgagc
1021 caaaagactg tggatctttc caaagcagct gctgggatgg gattcatcaa taagcatatg
1081 cttacgggca acatcttggc acaaccaaca acagtcttgg atattcccgt cacaaaggat
1141 aaaacacttg cgatggccag tgattttatt cgtaaggaga atctcaagac ttctgccatt
1201 cacattggag caattgagat tattatccag agctttgctt cccctgaaag tgatttgatg
1261 ggaggctttt tgcttgtgga ttctttacac actgatacag ctaatgctat tcgtagcatt
1321 tttgttgctc aatgcgggg aggaagacca gtcagagtgg tgaccttccc aaatacactg
1381 gcacctgtat tatgtgatct gaacaataga ttcaagctca tttgctcatt gccaaactgt
1441 gatattgtcc agggtagcca agtagcagaa gtgagtgtaa atgttgcagg atgtgctact
1501 tccatagaga aatctcacac cccttcccaa ttgtatacag aggaatttga aaaggagggt
1561 gctgttgttg tagaatactt aggcagacag acctattgtg ctcagcctag caatttaccc
1621 acagaagaaa aacttcggtc ccttaagttt gactttcatg ttgaacaacc aagtgtcctg
1681 aagttatcca attcctgcaa tgcgcacttt gtcaagggaa aaagtttgaa atactctatt
1741 tctggcaaag aagcagaaaa ccatgcagtt catgctactg tggtctctcg agaagggggct
1801 tctgcggcac ccaagcaata tgatcctatt ttgggacggg tgctggatcc acgaaatggg
1861 aatgtggctt ttccacaaat ggagcaaaac ttgtttgccc tttcttgga tgatacaagc
1921 tcagttcgtg gttctttgct tgacacaaaa ttcgcacaaa ctcgagtttt gttgtccaag
1981 gctatggctg tggtgatgt gttattggat gagtatctct atgatgtggt caatggacaa
2041 gattttagag ctactgtcgc ttttttgcgc acccatgtta taacaggcaa aataaaggtg
2101 acagctacca ccaacatttc tgacaactcg ggttgttgtt tgatgttggc cataaatagt
2161 ggtgtgaggg gtaagtatag tactgatgtt tatactatct gctctcaaga ctccatgacg
2221 tggaacccag ggtgcaaaaa gaacttctcg ttcacattta atccaaaccc ttgtggggat
2281 tcttggtctg ctgagatgat aagtcgaagc agagttagga tgacagttat ttgtgtttcg
2341 ggatggacct tatctcctac cacagatgtg attgccaagc tagactggtc aattgtcaat
2401 gagaaatgtg agcccaccat ttaccacttg gctgattgtc agaattggtt accccttaat
2461 cgttggatgg gaaaattgac tttccccag ggtgtgacaa gtgaggttcg aaggatgcct
2521 ctttctatag gaggcggtgc tggtgcgact caagcttct tggccaatat gcccaattca
2581 tggatatcaa tgtggagata tttagaggt gaacttcact ttgaagttac taaaatgagc
2641 tctccatata ttaaagccac tgttacattt ctcatagctt tggtaatct tagtgatgcc
2701 tttggttttt atgagagttt tcctcataga attgttcaat ttgctgaggt tgaggaaaaa
2761 tgtactttgg ttttctccca acaagagttt gtcactgctt ggtcaacaca agtaaaccc
2821 agaaccacac ttgaagcaga tggttgtccc tacctatatg caattattca tgatagtaca
```

Nucleotide Sequence of pM81-FSC-1
SEQ ID NO: 9

```
2881  acaggtacaa tctccggaga ttttatcttg gggtcaagct tgttggcatt aaggattttt
2941  gtggtatagg ttctaatccg ggtattgatg gttcccgctt gcttggagct atagcacaag
3001  gacctgtttg tgctgaagcc tcagatgtgt atagcccatg tatgatagct agcactcctc
3061  ctgctccatt ttcagacgtc acagcagtaa acttttgact taatcaacgg caaataact
3121  cctgttggtg atgacaattg gaatacgcac atttataatc ctccaattat gaatgtcttg
3181  cgtactgctg cttggaaatc tggaactatt catgttcaac ttaatgttag gggtgctggt
3241  gtcaaaagag cagattggga tggtcaagtc tttgtttacc tgcgccagtc catgaaccct
3301  gaaagttatg atgcgcggac atttgtgatc tcacaacctg gttctgccat gttgaacttc
3361  tcttttgata tcatagggcc gaatagcgga tttgaatttg ccgaaagccc atgggccaat
3421  cagaccacct ggtatcttga atgtgttgct accaatccca gacaaataca gcaatttgag
3481  gtcaacatgc gcttcgatcc taatttcagg gttgccggca atatcctgat gcccccattt
3541  ccactgtcaa cggaaactcc accgttatta agtttaggt ttcgggatat tgaacgctcc
3601  aagcgtagtg ttatggttgg acacactgct actgctgcag cgcctgcaaa acagctctta
3661  aactttgacc tacttaagtt agcaggtgac gttgagtcca accctgggcc cagtaaagga
3721  gaagaacttt tcactggagt tgtcccaatt cttgttgaat tagatggtga tgttaatggg
3781  cacaaatttt ctgtcagtgg agagggtgaa ggtgatgcaa catacggaaa acttacccttt
3841  aaatttattt gcactactgg aaaactacct gttccatggc caacacttgt cactactttc
3901  tcttatggtg ttcaatgctt ttcaagatac ccagatcata tgaaacggca tgactttttc
3961  aagagtgcca tgcccgaagg ttatgtacag gaaagaacta tattttttcaa ggatgacggg
4021  aactacaaga cacgtgctga agtcaagttt gaaggtgata cccttgttaa tagaatcgag
4081  ttaaaaggta ttgattttaa agaagatgga acattcttg gacacaaatt ggaatacaac
4141  tataactcac acaatgtata catcatggca gacaaacaaa gaatggaat caaagttaac
4201  ttcaaaatta gacacaacat tgaagatgga agcgttcaac tagcagacca ttatcaacaa
4261  aatactccaa ttggcgatgg ccctgtcctt ttaccagaca accattacct gtccacacaa
4321  tctgcccttt cgaaagatcc caacgaaaag agagaccaca tggtccttct tgagtttgta
4381  acagctgctg ggattacaca tggcatggat gaactataca ataaaggcc tttaactctg
4441  gtttcattaa attttcttta gtttgaattt actgttattc ggtgtgcatt tctatgtttg
4501  gtgagcggtt ttctgtgctc agagtgtgtt tattttatgt aatttaattt ctttgtgagc
4561  tcctgtttag caggtcgtcc cttcagcaag gacacaaaaa gatttaattt ttattaaaaa
4621  aaaaaaaaaa aaagaccggg aattcgatat caagcttatc gacctgcaga tcgttcaaac
4681  atttggcaat aaagtttctt aagattgaat cctgttgccg tcttgcgat gattatcata
4741  taattctgt tgaattacgt taagcatgta ataattaaca tgtaatgcat gacgttattt
4801  atgagatggg ttttttatgat tagagtcccg caattataca tttaatacgc gatagaaaac
4861  aaaatatagc gcgcaaacta ggataaatta tcgcgcgcgg tgtcatctat gttactagat
4921  ctctagagtc tcaagcttgg cgcgccagct gcattaatga atcggccaac gcgcggggag
4981  aggcggtttg cgtattgggc gctcttccgc ttcctcgctc actgactcgc tgcgctcggt
5041  cgttcggctg cggcgagcgg tatcagctca ctcaaaggcg gtaatacggt tatccacaga
5101  atcaggggat aacgcaggaa agaacatgtg agcaaaaggc cagcaaaagg ccaggaaccg
```

-continued

Nucleotide Sequence of pM81-FSC-1
SEQ ID NO: 9

```
5161 taaaaaggcc gcgttgctgg cgttttttcca taggctccgc cccctgacg agcatcacaa
5221 aaatcgacgc tcaagtcaga ggtggcgaaa cccgacagga ctataaagat accaggcgtt
5281 tccccctgga agctccctcg tgcgctctcc tgttccgacc ctgccgctta ccggatacct
5341 gtccgccttt ctcccttcgg gaagcgtggc gctttctcat agctcacgct gtaggtatct
5401 cagttcggtg taggtcgttc gctccaagct gggctgtgtg cacgaacccc ccgttcagcc
5461 cgaccgctgc gccttatccg gtaactatcg tcttgagtcc aacccggtaa gacacgactt
5521 atcgccactg gcagcagcca ctggtaacag gattagcaga gcgaggtatg taggcggtgc
5581 tacagagttc ttgaagtggt ggcctaacta cggctacact agaagaacag tatttggtat
5641 ctgcgctctg ctgaagccag ttaccttcgg aaaaagagtt ggtagctctt gatccggcaa
5701 acaaaccacc gctggtagcg gtggtttttt tgtttgcaag cagcagatta cgcgcagaaa
5761 aaaaggatct caagaagatc ctttgatctt ttctacgggg tctgacgctc agtggaacga
5821 aaactcacgt taagggattt tggttatgag attatcaaaa aggatcttca cctagatcct
5881 tttaaattaa aaatgaagtt ttaaatcaat ctaaagtata tatgagtaaa cttggtctga
5941 cagttaccaa tgcttaatca gtgaggcacc tatctcagcg atctgtctat ttcgttcatc
6001 catagttgcc tgactccccg tcgtgtagat aactacgata cgggagggct taccatctgg
6061 ccccagtgct gcaatgatac cgcgagaccc acgctcaccg gctccagatt tatcagcaat
6121 aaaccagcca gccggaaggg ccgagcgcag aagtggtcct gcaactttat ccgcctccat
6181 ccagtctatt aattgttgcc gggaagctag agtaagtagt tcgccagtta atagtttgcg
6241 caacgttgtt gccattgcta caggcatcgt ggtgtcacgc tcgtcgtttg gtatggcttc
6301 attcagctcc ggttcccaac gatcaaggcg agttacatga tcccccatgt tgtgcaaaaa
6361 agcggttagc tccttcggtc ctccgatcgt tgtcagaagt aagttggccg cagtgttatc
6421 actcatggtt atggcagcac tgcataattc tcttactgtc atgccatccg taagatgctt
6481 ttctgtgact ggtgagtact caaccaagtc attctgagaa tagtgtatgc ggcgaccgag
6541 ttgctcttgc ccggcgtcaa tacgggataa taccgcgcca catagcagaa ctttaaaagt
6601 gctcatcatt ggaaaacgtt cttcggggcg aaaactctca aggatcttac cgctgttgag
6661 atccagttcg atgtaaccca ctcgtgcacc caactgatct tcagcatctt ttactttcac
6721 cagcgtttct gggtgagcaa aaacaggaag gcaaaatgcc gcaaaaaagg gaataagggc
6781 gacacggaaa tgttgaatac tcatactctt cctttttcaa tattattgaa gcatttatca
6841 gggttattgt cttatgagcg gatacatatt tgaatgtatt tagaaaaata aacaaatagg
6901 ggttccgcgc acatttcccc gaaaagtgcc acctaaattg taagcgttaa tattttgtta
6961 aaattcgcgt taaattttg ttaaatcagc tcattttta accaataggc cgaaatcggc
7021 aaaatccctt ataaatcaaa agaatagacc gagataggg tgagtgttgt tccagtttgg
7081 aacaagagtc cactattaaa gaacgtggac tccaacgtca aagggcgaaa aaccgtctat
7141 cagggcgatg gcccactacg tgaaccatca ccctaatcaa gttttttggg gtcgaggtgc
7201 cgtaaagcac taaatcggaa ccctaaaggg agcccccgat ttagagcttg acggggaaag
7261 ccggcgaacg tggcgagaaa ggaagggaag aaagcgaaag gagcgggcgc tagggcgctg
7321 gcaagtgtag cggtcacgct gcgcgtaacc accacacccg ccgcgcttaa tgcgccgcta
7381 cagggcgcgt cccattcgcc attcaggctg cgcaactgtt gggaagggcg atcggtgcgg
7441 gcctcttcgc tattacgcca gctggcgaaa gggggatgtg ctgcaaggcg attaagttgg
```

Nucleotide Sequence of pM81-FSC-1
SEQ ID NO: 9

-continued

```
7501 gtaacgccag ggttttccca gtcacgacgt tgtaaaacga cggccagtga gtactttggc 7561 gtaatcatgg tcatagctgt ttcctgtgtg aaattgttat ccgctcacaa ttccacacaa 7621 catacgagcc ggaagcataa agtgtaaagc ctggggtgcc taatgagtga gctaactcac 7681 attaattgcg ttgcgctcac tgcccgcttt ccagtcggga aacctggcgc gc
//
```

Nucleotide sequence of pM81-FSC-2
SEQ ID NO: 10

LOCUS pM81-FSC2 4173 bp DNA circular
10-OCT-2007

| FEATURES | Location/Qualifiers |
|---|---|
| rep_origin | complement(1271 . . . 1890)<br>/vntifkey = "33"<br>/label = pBR322_origin |
| rep_origin | complement(3168 . . . 3474)<br>/vntifkey = "33"<br>/label = f1_origin |
| promoter | complement(2947 . . . 2975)<br>/vntifkey = "30"<br>/label = AmpR\promoter |
| misc_feature | complement(3492 . . . 3647)<br>/vntifkey = "21"<br>/label = lacZ_a |
| CDS | complement(2045 . . . 2905)<br>/vntifkey = "4"<br>/label = AmpR |
| 3'UTR | 533 . . . 716<br>/vntifkey = "50"<br>/label = CPMV\RNA2\3'UTR |
| terminator | 770 . . . 1022<br>/vntifkey = "43"<br>/label = Nos\Terminator |
| promoter | 3859 . . . 4173<br>/vntifkey = "29"<br>/label = CaMV\35S\promoter |
| 5'UTR | 1 . . . 160<br>/vntifkey = "52"<br>/label = CPMV\RNA2\5'UTR |
| misc_feature | 507 . . . 532<br>/vntifkey = "21"<br>/label = FSC-2\MCS |

```
BASE COUNT 1090 a 969 c 982 g 1132 t
ORIGIN
   1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg caccagtaca atgttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt
```

-continued

Nucleotide sequence of pM81-FSC-2
SEQ ID NO: 10

```
 361 gacgaggtat tgttgcctgt acttctttct tcttcttctt gctgattggt tctataagaa
 421 atctagtatt ttctttgaaa cagagttttc ccgtggtttt cgaacttgga gaaagattgt
 481 taagcttctg tatattctgc ccaaattcgc gacgatcgta ctctcgaggc cttaactct
 541 ggtttcatta aattttcttt agtttgaatt tactgttatt cggtgtgcat ttctatgttt
 601 ggtgagcggt tttctgtgct cagagtgtgt ttattttatg taatttaatt tctttgtgag
 661 ctcctgttta gcaggtcgtc ccttcagcaa ggacacaaaa agattttaat tttattaaaa
 721 aaaaaaaaaa aaaagaccgg gaattcgata tcaagcttat cgacctgcag atcgttcaaa
 781 catttggcaa taaagtttct taagattgaa tcctgttgcc ggtcttgcga tgattatcat
 841 ataatttctg ttgaattacg ttaagcatgt aataattaac atgtaatgca tgacgttatt
 901 tatgagatgg gttttatga ttagagtccc gcaattatac atttaatacg cgatagaaaa
  61 caaatatag cgcgcaaact aggataaatt atcgcgcgcg gtgtcatcta tgttactaga
1021 tctctagagt ctcaagcttg gcgcgccagc tgcattaatg aatcggccaa cgcgcgggga
1081 gaggcggttt gcgtattggg cgctcttccg cttcctcgct cactgactcg ctgcgctcgg
1141 tcgttcggct gcggcgagcg gtatcagctc actcaaaggc ggtaatacgg ttatccacag
1201 aatcagggga taacgcagga aagaacatgt gagcaaaagg ccagcaaaag gccaggaacc
1261 gtaaaaaggc cgcgttgctg gcgttttttcc ataggctccg cccccctgac gagcatcaca
1321 aaaatcgacg ctcaagtcag aggtggcgaa acccgacagg actataaaga taccaggcgt
1381 ttccccctgg aagctccctc gtgcgctctc ctgttccgac cctgccgctt accggatacc
1441 tgtccgcctt tctcccttcg ggaagcgtgg cgctttctca tagctcacgc tgtaggtatc
1501 tcagttcggt gtaggtcgtt cgctccaagc tgggctgtgt gcacgaaccc cccgttcagc
1561 ccgaccgctg cgccttatcc ggtaactatc gtcttgagtc caacccggta agacacgact
1621 tatcgccact ggcagcagcc actggtaaca ggattagcag agcgaggtat gtaggcggtg
1681 ctacagagtt cttgaagtgg tggcctaact acggctacac tagaagaaca gtatttggta
1741 tctgcgctct gctgaagcca gttaccttcg gaaaaagagt tggtagctct tgatccggca
1801 aacaaaccac cgctggtagc ggtggttttt tgtttgcaa gcagcagatt acgcgcagaa
1861 aaaaaggatc tcaagaagat cctttgatct tttctacggg gtctgacgct cagtggaacg
1921 aaaactcacg ttaagggatt ttggttatga gattatcaaa aaggatcttc acctagatcc
1981 ttttaaatta aaaatgaagt tttaaatcaa tctaaagtat atatgagtaa acttggtctg
2041 acagttacca atgcttaatc agtgaggcac ctatctcagc gatctgtcta tttcgttcat
2101 ccatagttgc ctgactcccc gtcgtgtaga taactacgat acgggagggc ttaccatctg
2161 gccccagtgc tgcaatgata ccgcgagacc cacgctcacc ggctccagat ttatcagcaa
2221 taaaccagcc agccggaagg gccgagcgca gaagtggtcc tgcaacttta tccgcctcca
2281 tccagtctat taattgttgc cgggaagcta gagtaagtag ttcgccagtt aatagtttgc
2341 gcaacgttgt tgccattgct acaggcatcg tggtgtcacg ctcgtcgttt ggtatggctt
2401 cattcagctc cggttcccaa cgatcaaggc gagttacatg atccccccatg ttgtgcaaaa
2461 aagcggttag ctccttcggt cctccgatcg ttgtcagaag taagttggcc gcagtgttat
2521 cactcatggt tatggcagca ctgcataatt ctcttactgt catgccatcc gtaagatgct
2581 tttctgtgac tggtgagtac tcaaccaagt cattctgaga atagtgtatg cggcgaccga
```

Nucleotide sequence of pM81-FSC-2
SEQ ID NO: 10

```
2641 gttgctcttg cccggcgtca atacgggata ataccgcgcc acatagcaga actttaaaag
2701 tgctcatcat tggaaaacgt tcttcggggc gaaaactctc aaggatctta ccgctgttga
2761 gatccagttc gatgtaaccc actcgtgcac ccaactgatc ttcagcatct tttactttca
2821 ccagcgtttc tgggtgagca aaaacaggaa ggcaaaatgc cgcaaaaaag ggaataaggg
2881 cgacacggaa atgttgaata ctcatactct tcctttttca atattattga agcatttatc
2941 agggttattg tcttatgagc ggatacatat ttgaatgtat ttagaaaaat aaacaaatag
3001 gggttccgcg cacatttccc cgaaaagtgc cacctaaatt gtaagcgtta atattttgtt
3061 aaaattcgcg ttaaattttt gttaaatcag ctcatttttt aaccaatagg ccgaaatcgg
3121 caaaatccct tataaatcaa agaatagacc gagataggg ttgagtgttg ttccagtttg
3181 gaacaagagt ccactattaa agaacgtgga ctccaacgtc aaagggcgaa aaaccgtcta
3241 tcagggcgat ggcccactac gtgaaccatc accctaatca agttttttgg ggtcgaggtg
3301 ccgtaaagca ctaaatcgga accctaaagg agccccccga tttagagctt gacggggaaa
3361 gccggcgaac gtggcgagaa aggaagggaa gaaagcgaaa ggagcgggcg ctagggcgct
3421 ggcaagtgta gcggtcacgc tgcgcgtaac caccacaccc gccgcgctta atgcgccgct
3481 acagggcgcg tcccattcgc cattcaggct gcgcaactgt tgggaagggc gatcggtgcg
3541 ggcctcttcg ctattacgcc agctggcgaa aggggggatgt gctgcaaggc gattaagttg
3601 ggtaacgcca gggttttccc agtcacgacg ttgtaaaacg acggccagtg agtactttgg
3661 cgtaatcatg gtcatagctg tttcctgtgt gaaattgtta tccgctcaca attccacaca
3721 acatacgagc cggaagcata aagtgtaaag cctggggtgc ctaatgagtg agctaactca
3781 cattaattgc gttgcgctca ctgcccgctt tccagtcggg aaacctggcc gcttaattaa
3841 gaattcgagc tccaccgcgg aaacctcctc ggattccatt gcccagctat ctgtcacttt
3901 attgagaaga tagtggaaaa ggaaggtggc tcctacaaat gccatcattg cgataaagga
3961 aaggccatcg ttgaagatgc ctctgccgac agtggtccca agatggaccc ccacccacg
4021 aggagcatcg tggaaaaaga agacgttcca accacgtctt caaagcaagt ggattgatgt
4081 gatatctcca ctgacgtaag ggatgacgca caatcccact atccttcgca agacccttcc
4141 tctatataag gaagttcatt tcatttggag agg
//
```

The invention claimed is:

1. A gene expression construct comprising:
(a) an expression enhancer sequence derived from the RNA-2 genome segment of a Comoviridae bipartite RNA virus, in which a target initiation site having the sequence AUG in the RNA-2 genome segment has been mutated,
wherein the RNA2 genome segment of the Comoviridae virus encodes two carboxy coterminal proteins through two different translation initiation sites located in the same triplet reading frame,
wherein the mutated target initiation site is the first of these two initiation sites and thus corresponds to the initiation site at position 161 in the wild-type RNA-2 segment of cowpea mosaic virus (CPMV) shown in SEQ ID NO: 1; and
wherein the enhancer sequence has at least 90% identity to nucleotides 1 to 507 of the CPMV RNA-2 genome segment sequence shown in Table 1, and
(b) a heterologous sequence for facilitating insertion of a gene encoding a protein of interest into the gene expression construct, wherein the heterologous sequence is located downstream of the mutated target initiation site in the enhancer sequence; and optionally
(c) a 3' UTR.

2. A gene expression system comprising an expression construct according to claim 1.

3. A gene expression system comprising:
(a) an expression enhancer sequence derived from the RNA-2 genome segment of a Comoviridae bipartite RNA virus, in which a target initiation site having the sequence AUG in the RNA-2 genome segment has been mutated,
wherein the RNA2 genome segment of the Comoviridae virus encodes two carboxy coterminal proteins through two different translation initiation sites located in the same triplet reading frame,
wherein the mutated target initiation site is the first of these two initiation sites and thus corresponds to the initiation site at position 161 in the wild-type RNA-2 segment of cowpea mosaic virus (CPMV) shown in SEQ ID NO: 1; and
wherein the enhancer sequence has at least 90% identity to nucleotides 1 to 507 of the CPMV RNA-2 genome segment sequence shown in Table 1, and
(b) a heterologous gene encoding a protein of interest, wherein the gene encoding the protein of interest is located downstream of the enhancer sequence.

4. A gene expression system according to claim 3, wherein the gene encoding the protein of interest is operably linked to promoter and terminator sequences.

5. A gene expression system according to claim 4, wherein the gene encoding the protein of interest is located downstream of the enhancer sequence and upstream of the terminator sequence.

6. A gene expression system according to claim 3 further comprising a 3' UTR which is optionally derived from the same bipartite RNA virus.

7. A gene expression system according to claim 3, wherein the comovirus is CPMV.

8. A gene expression system according to claim 3, wherein the enhancer sequence comprises at least nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of a comoviral RNA-2 genome segment sequence with said mutated target initiation site.

9. A gene expression system according to claim 7, wherein the enhancer sequence comprises nucleotides 10 to 512, 20 to 512, 30 to 512, 40 to 512, 50 to 512, 100 to 512, 150 to 512, 1 to 514, 10 to 514, 20 to 514, 30 to 514, 40 to 514, 50 to 514, 100 to 514, 150 to 514, 1 to 511, 10 to 511, 20 to 511, 30 to 511, 40 to 511, 50 to 511, 100 to 511, 150 to 511, 1 to 509, 10 to 509, 20 to 509, 30 to 509, 40 to 509, 50 to 509, 100 to 509, 150 to 509, 1 to 507, 10 to 507, 20 to 507, 30 to 507, 40 to 507, 50 to 507, 100 to 507, or 150 to 507 of the CPMV RNA-2 genome segment sequence shown in Table 1, wherein the target initiation site at position 161 in the wild-type CPMV RNA-2 genome segment has been mutated.

10. A gene expression system according to claim 3, wherein the enhancer sequence has at least 99%, 98%, 97%, 96%, or 95% identity to nucleotides 1 to 507 of the CPMV RNA-2 genome segment sequence shown in Table 1, wherein the target initiation site at position 161 in the wild-type CPMV RNA-2 genome segment has been mutated.

11. A gene expression system comprising:
(a) a promoter;
(b) nucleotides 1 to 507 of the cowpea mosaic virus RNA-2 genome segment sequence shown in Table 1, wherein the AUG at position 161 has been mutated as shown in Table 2, located downstream of the promoter;
(c) a heteroloqous gene encoding a protein of interest located downstream of the sequence defined in (b);
(d) nucleotides 3302 to 3481 of the cowpea mosaic virus RNA-2 genome segment sequence shown in Table 1, located downstream of the gene encoding the protein of interest; and
(e) a nopaline synthase terminator located downstream of the sequence defined in (d).

12. A gene expression system, wherein the gene expression system comprises:
(a) a promoter;
(b) an expression enhancer sequence with at least 90% identity to nucleotides 1 to 507 of the cowpea mosaic virus RNA-2 genome segment sequence shown in Table 1, wherein the AUG at position 161 has been mutated, located downstream of the promoter;

(c) a heterologous gene encoding a protein of interest located downstream of the sequence defined in (b);

(d) nucleotides 3302 to 3481 of the cowpea mosaic virus RNA-2 genome segment sequence shown in Table 1, located downstream of the gene encoding the protein of interest; and (e) a nopaline synthase terminator located downstream of the sequence defined in (d).

13. A process for increasing the expression or translational enhancing activity of a sequence derived from an RNA-2 genome segment of a Comoviridae bipartite RNA virus, comprising mutating a target initiation site therein, wherein the RNA2 genome segment of the Comoviridae virus encodes two carboxy coterminal proteins through two different translation initiation sites located in the same triplet reading frame, wherein the mutated initiation site is the first of these two initiation sites and thus corresponds to the initiation site at position 161 in the wild-type RNA-2 segment of CPMV shown in SEQ ID NO: 1, wherein the derived sequence has at least 90% identity to nucleotides 1 to 507 of the CPMV RNA-2 genome segment sequence shown in Table 1, wherein said mutation enhances the expression of a heterologous ORF to which the sequence is attached.

14. A process according to claim 13, wherein the comovirus is CPMV.

15. A method for expressing a protein of interest in a host organism using a gene expression system according to claim 2 which method comprises introducing the gene expression system into the host organism so that the protein of interest is expressed in the host organism.

16. A method according to claim 15, wherein the host organism is a eukaryotic host selected from the group consisting of a plant and an insect.

17. A method of enhancing the translation of a heterologous protein of interest from a gene or open reading frame (ORF) encoding the same which is operably linked to an RNA2-genome segment of a Comoviridae bipartite virus derived sequence, wherein the RNA2 genome segment of the Comoviridae virus encodes two carboxy coterminal proteins through two different translation initiation sites located in the same triplet reading frame, said method comprising mutating a target initiation site in the RNA2-derived sequence which is the first of these two initiation sites and thus corresponds to the initiation site at position 161 in the wild-type RNA-2 segment of CPMV, wherein the derived sequence has at least 90% identity to nucleotides 1 to 507 of the CPMV RNA-2 genome segment sequence shown in Table 1.

18. A gene expression system comprising:

(a) a first gene construct comprising a sequence derived from a truncated RNA-2 of a Comoviridae bipartite virus genome carrying at least one foreign gene encoding a heterologous protein of interest operably linked to promoter and terminator sequences, wherein the gene construct comprises a mutated target initiation site upstream of the foreign gene, wherein the RNA2 genome segment of the Comoviridae virus encodes two carboxy coterminal proteins through two different translation initiation sites located in the same triplet reading frame, wherein the mutated initiation site is the first of these two initiation sites and thus corresponds to the initiation site at position 161 in the wild-type RNA-2 segment of CPMV, wherein the derived sequence has at least 90% identity to nucleotides 1 to 507 of the CPMV RNA-2 genome segment sequence shown in Table 1;

and optionally (b) a second gene construct optionally incorporated within said first gene construct comprising a suppressor of gene silencing operably linked to promoter and terminator sequences.

19. A method of expressing a protein in a plant comprising the steps of:

(a) introducing a gene expression construct into a plant cell, said gene expression construct comprising (i) a first gene construct comprising a sequence derived from a truncated RNA-2 of a Comoviridae bipartite virus genome carrying at least one foreign gene encoding a heterologous protein of interest operably linked to promoter and terminator sequences, wherein the sequence derived from a truncated RNA-2 of a Comoviridae bipartite virus genome comprises a mutated target initiation site upstream of the foreign gene and which RNA-2 genome segment of the Comoviridae virus also encodes two carboxy coterminal proteins through two different translation initiation sites located in the same triplet reading frame, wherein the mutated initiation site is the first of these two initiation sites and thus corresponds to the initiation site at position 161 in the wild type RNA-2 segment of CPMV, and wherein the derived sequence has at least 90% identity to nucleotides 1 to 507 of the CPMV RNA-2 genome segment sequence shown in Table 1; and optionally (b) introducing a second gene construct comprising a suppressor of gene silencing operably linked to promoter and terminator sequences, into the plant cell, said second gene construct optionally incorporated within said first gene construct.

20. A host organism obtained by the method according to claim 19, said host organism comprising the gene expression construct, wherein the gene encoding the protein of interest is expressed at an enhanced level compared with expression of the same protein from a gene expression system differing only in that the target initiation site has not been mutated.

21. A host organism transiently transfected with a gene expression system according to claim 2 and comprising said gene expression system.

22. A host organism according to claim 20, wherein the host organism is a plant or plant cell.

23. A transgenic host organism stably transformed with a gene expression system according to claim 2.

24. A method for generating a protein of interest, comprising using a host organism according to claim 20 and optionally harvesting a tissue in which the protein of interest has been expressed and isolating the protein of interest from the tissue.

25. A gene expression system as claimed in claim 3 which is comprised in a DNA binary vector.

* * * * *

UNITED STATES PATENT AND TRADEMARK OFFICE
CERTIFICATE OF CORRECTION

Page 1 of 1

PATENT NO. : 8,674,084 B2
APPLICATION NO. : 12/812165
DATED : March 18, 2014
INVENTOR(S) : Frank Sainsbury and George Peter Lomonossoff It is certified that error appears in the above-identified patent and that said Letters Patent is hereby corrected as shown below:

On the Title Page, Item (54) and in the Specification, Column 1, Line 1, Title, please delete "PROTEIN EXPRESSION SYSTEM", and insert --PROTEIN EXPRESSION SYSTEMS--.

On the Title Page:

The first or sole Notice should read --

Subject to any disclaimer, the term of this patent is extended or adjusted under 35 U.S.C. 154(b) by 192 days.

Signed and Sealed this
Thirteenth Day of January, 2015

Michelle K. Lee
*Deputy Director of the United States Patent and Trademark Office*

SEQUENCE LISTING

<160> NUMBER OF SEQ ID NOS: 37

<210> SEQ ID NO 1
<211> LENGTH: 3481
<212> TYPE: DNA
<213> ORGANISM: Cowpea mosaic virus

<400> SEQUENCE: 1

```
tattaaaatc ttaataggtt ttgataaaag cgaacgtggg gaaacccgaa ccaaaccttc    60
ttctaaattc tctctcatct ctcttaaagc aaacttctct cttgtctttc ttgcatgagc   120
gatcttcaac gttgtcagat cgtgcttcgg caccagtaca atgttttctt tcactgaagc   180
```

```
gaaatcaaag atctctttgt ggacacgtag tgcggcgcca ttaaataacg tgtacttgtc    240
ctattcttgt cggtgtggtc ttgggaaaag aaagcttgct ggaggctgct gttcagcccc    300
atacattact tgttacgatt ctgctgactt tcggcgggtg caatatctct acttctgctt    360
gacgaggtat tgttgcctgt acttcttcct tcttcttctt gctgattggt tctataagaa    420
atctagtatt ttctttgaaa cagagttttc ccgtggtttt cgaacttgga gaaagattgt    480
taagcttctg tatattctgc ccaaatttga aatggaaagc attatgagcc gtggtattcc    540
ttcaggaatt ttggaggaaa agctattcca gttcaaacgt gccaagaag ggaataaacc     600 cttgaaggat gagattccca gcctgaggga tatgtatgtg tctcacactt ctaaatggaa    660
tgtgctcaga aaaatgagcc aaaagactgt ggatctttcc aaagcagctg ctgggatggg    720
attcatcaat aagcatatgc ttacgggcaa catcttggca caaccaacaa cagtcttgga    780
tattcccgtc acaaaggata aaacacttgc gatggccagt gatttattc gtaaggagaa     840 tctcaagact tctgccattc acattggagc aattgagatt attatccaga gctttgcttc    900
ccctgaaagt gatttgatgg gaggcttttt gcttgtggat tctttacaca ctgatacagc    960
taatgctatt cgtagcattt tgttgctcc aatgcgggga ggaagaccag tcagagtggt    1020
gaccttccca aatacactgg cacctgtatc atgtgatctg aacaatagat tcaagctcat   1080
ttgctcattg ccaaactgtg atattgtcca gggtagccaa gtagcagaag tgagtgtaaa   1140
tgttgcagga tgtgctactt ccatagagaa atctcacacc ccttcccaat tgtatacaga   1200
ggaatttgaa aaggagggtg ctgttgttgt agaatactta gcagacaga cctattgtgc    1260 tcagcctagc aatttacccca cagaagaaaa acttcggtcc cttaagtttg actttcatgt   1320
tgaacaacca agtgtcctga agttatccaa ttcctgcaat gcgcactttg tcaagggaga   1380
aagtttgaaa tactctattt ctggcaaaga agcagaaaac catgcagttc atgctactgt   1440
ggtctctcga aaggggctt ctgcggcacc caagcaatat gatcctattt tgggacgggt    1500
gctggatcca cgaaatggga atgtggcttt tccacaaatg gagcaaaact tgtttgccct   1560
ttctttggat gatacaagct cagttcgtgg ttctttgctt gacacaaaat tcgcacaaac   1620
tcgagttttg ttgtccaagg ctatggctgg tggtgatgtg ttattggatg agtatctcta   1680
tgatgtggtc aatggacaag attttagagc tactgtcgct ttttttgcgca cccatgttat   1740 aacaggcaaa ataaaggtga cagctaccac caacatttct gacaactcgg ttgttgtt    1800 gatgttggcc ataaatagtg gtgtgagggg taagtatagt actgatgttt atactatctg   1860
ctctcaagac tccatgacgt ggaacccagg gtgcaaaaag aacttctcgt tcacatttaa   1920
tccaaaccct tgtggggatt cttggtctgc tgagatgata agtcgaagca gagttaggat   1980
gacagttatt tgtgtttcgg gatggacctt atctcctacc acagatgtga ttgccaagct   2040
agactggtca attgtcaatg agaaatgtga gcccaccatt taccacttgg ctgattgtca   2100
gaattggtta cccctaatc gttggatggg aaaattgact tttccccagg gtgtgacaag    2160
tgaggttcga aggatgcctc tttctatagg aggcggtgct ggtgcgactc aagctttctt   2220
ggccaatatg cccaattcat ggatatcaat gtggagatat tttagaggtg aacttcactt   2280
tgaagttact aaaatgagct ctccatatat taaagccact gttacatttc tcatagcttt   2340
tggtaatctt agtgatgcct ttggtttta tgagagtttt cctcatagaa ttgttcaatt    2400
tgctgaggtt gaggaaaaat gtactttggt tttctcccaa caagagtttg tcactgcttg   2460
gtcaacacaa gtaaacccca gaaccacact tgaagcagat ggttgtccct acctatatgc   2520
aattattcat gatagtacaa caggtacaat ctccggagat tttaatcttg gggtcaagct   2580
```

```
tgttggcatt aaggattttt gtggtatagg ttctaatccg ggtattgatg gttcccgctt    2640
gcttggagct atagcacaag gacctgtttg tgctgaagcc tcagatgtgt atagcccatg    2700
tatgatagct agcactcctc ctgctccatt ttcagacgtt acagcagtaa cttttgactt    2760
aatcaacggc aaaataactc ctgttggtga tgacaattgg aatacgcaca tttataatcc    2820
tccaattatg aatgtcttgc gtactgctgc ttggaaatct ggaactattc atgttcaact    2880
taatgttagg ggtgctggtg tcaaaagagc agattgggat ggtcaagtct ttgtttacct    2940
gcgccagtcc atgaaccctg aaagttatga tgcgcggaca tttgtgatct cacaacctgg    3000
ttctgccatg ttgaacttct cttttgatat catagggccg aatagcggat ttgaatttgc    3060
cgaaagccca tgggccaatc agaccacctg gtatcttgaa tgtgttgcta ccaatcccag    3120
acaaatacag caatttgagg tcaacatgcg cttcgatcct aatttcaggg ttgccggcaa    3180
tatcctgatg ccccattttc cactgtcaac ggaaactcca ccgttattaa agtttaggtt    3240
tcgggatatt gaacgctcca agcgtagtgt tatggttgga cacactgcta ctgctgctta    3300
actctggttt cattaaattt tctttagttt gaatttactg ttatttggtg tgcatttcta    3360
tgtttggtga gcggttttct gtgctcagag tgtgttatt ttatgtaatt taatttcttt    3420
gtgagctcct gtttagcagg tcgtcccttc agcaaggaca caaaaagatt ttaattttat    3480
t                                                                    3481

<210> SEQ ID NO 2
<211> LENGTH: 31
<212> TYPE: DNA
<213> ORGANISM: Artificial sequence
<220> FEATURE:
<223> OTHER INFORMATION: Synthetic sequence: Oligonucleotide A115G-F

<400> SEQUENCE: 2
cttgtctttc ttgcgtgagc gatcttcaac g                                    31

<210> SEQ ID NO 3
<211> LENGTH: 31
<212> TYPE: DNA
<213> ORGANISM: Artificial sequence
<220> FEATURE:
<223> OTHER INFORMATION: Synthetic sequence: Oligonucleotide A115G-R

<400> SEQUENCE: 3
cgttgaagat cgctcacgca agaaagacaa g                                    31

<210> SEQ ID NO 4
<211> LENGTH: 33
<212> TYPE: DNA
<213> ORGANISM: Artificial sequence
<220> FEATURE:
<223> OTHER INFORMATION: Synthetic sequence: Oligonucleotide U162C-F

<400> SEQUENCE: 4
ggcaccagta caacgttttc tttcactgaa gcg                                  33

<210> SEQ ID NO 5
<211> LENGTH: 33
<212> TYPE: DNA
<213> ORGANISM: Artificial sequence
<220> FEATURE:
<223> OTHER INFORMATION: Synthetic sequence: Oligonucleotide U162C-R

<400> SEQUENCE: 5
cgcttcagtg aaagaaaacg ttgtactggt gcc                                  33
```

<210> SEQ ID NO 6
<211> LENGTH: 50
<212> TYPE: DNA
<213> ORGANISM: Cowpea mosaic virus

<400> SEQUENCE: 6
tatattctgc ccaaatttga aatggaaagc attatgagcc gtggtattcc 50

<210> SEQ ID NO 7
<211> LENGTH: 50
<212> TYPE: DNA
<213> ORGANISM: Artificial sequence
<220> FEATURE:
<223> OTHER INFORMATION: Synthetic sequence: Mutated sequence in pM81-FSC-1

<400> SEQUENCE: 7
tatattctgc ccaaatttgt catgaaaagc attatgagcc gtggtattcc 50

<210> SEQ ID NO 8
<211> LENGTH: 42
<212> TYPE: DNA
<213> ORGANISM: Artificial sequence
<220> FEATURE:
<223> OTHER INFORMATION: Synthetic sequence: Mutated sequence in pM81-FSC-2

<400> SEQUENCE: 8
tatattctgc ccaaattcgc gacgatcgta ctctcgaggc ct 42

<210> SEQ ID NO 9
<211> LENGTH: 7732
<212> TYPE: DNA
<213> ORGANISM: Artificial sequence
<220> FEATURE:
<223> OTHER INFORMATION: Synthetic sequence: pM81-FSC-1

<400> SEQUENCE: 9
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcatgag cgatcttcaa cgttgtcaga 480
tcgtgcttcg gcaccagtac aatgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcatgaaaag cattatgagc cgtggtattc cttcaggaat tttggaggaa 900
aaagctattc agttcaaacg tgccaaagaa gggaataaac ccttgaagga tgagattccc 960
aagcctgagg atatgtatgt gtctcacact tctaaatgga atgtgctcag aaaaatgagc 1020

```
caaaagactg tggatctttc caaagcagct gctgggatgg gattcatcaa taagcatatg    1080
cttacgggca acatcttggc acaaccaaca acagtcttgg atattcccgt cacaaaggat    1140
aaaacacttg cgatggccag tgattttatt cgtaaggaga atctcaagac ttctgccatt    1200
cacattggag caattgagat tattatccag agctttgctt ccctgaaag tgatttgatg     1260 ggaggctttt tgcttgtgga ttctttacac actgatacag ctaatgctat tcgtagcatt    1320
tttgttgctc caatgcgggg aggaagacca gtcagagtgg tgaccttccc aaatacactg    1380
gcacctgtat tatgtgatct gaacaataga ttcaagctca tttgctcatt gccaaactgt    1440
gatattgtcc agggtagcca agtagcagaa gtgagtgtaa atgttgcagg atgtgctact    1500
tccatagaga aatctcacac cccttcccaa ttgtatacag aggaatttga aaaggagggt    1560
gctgttgttg tagaatactt aggcagacag acctattgtg ctcagcctag caatttaccc    1620
acagaagaaa aacttcggtc ccttaagttt gactttcatg ttgaacaacc aagtgtcctg    1680
aagttatcca attcctgcaa tgcgcacttt gtcaagggaa aaagtttgaa atactctatt    1740
tctggcaaag aagcagaaaa ccatgcagtt catgctactg tggtctctcg agaaggggct    1800
tctgcggcac ccaagcaata tgatcctatt ttgggacggg tgctggatcc acgaaatggg    1860
aatgtggctt ttccacaaat ggagcaaaac ttgtttgccc tttctttgga tgatacaagc    1920
tcagttcgtg gttctttgct tgacacaaaa ttcgcacaaa ctcgagtttt gttgtccaag    1980
gctatggctg gtggtgatgt gttattggat gagtatctct atgatgtggt caatggacaa    2040
gattttagag ctactgtcgc ttttttgcgc acccatgtta taacaggcaa aataaaggtg    2100
acagctacca ccaacatttc tgacaactcg ggttgttgtt tgatgttggc cataaatagt    2160
ggtgtgaggg gtaagtatag tactgatgtt tatactatct gctctcaaga ctccatgacg    2220
tggaacccag ggtgcaaaaa gaacttctcg ttcacattta atccaaaccc ttgtggggat    2280
tcttggtctg ctgagatgat aagtcgaagc agagttagga tgcagttat ttgtgtttcg     2340 ggatggacct tatctcctac cacagatgtg attgccaagc tagactggtc aattgtcaat    2400
gagaaatgtg agcccaccat ttaccacttg gctgattgtc agaattggtt accccttaat    2460
cgttggatgg gaaaattgac ttttccccag ggtgtgacaa gtgaggttcg aaggatgcct    2520
ctttctatag gaggcggtgc tggtgcgact caagctttct tggccaatat gcccaattca    2580
tggatatcaa tgtggagata ttttagaggt gaacttcact ttgaagttac taaaatgagc    2640 ctccatata ttaaagccac tgttacattt ctcatagctt ttggtaatct tagtgatgcc     2700
tttggttttt atgagagttt tcctcataga attgttcaat ttgctgaggt tgaggaaaaa    2760
tgtactttgg ttttctccca acaagagttt gtcactgctt ggtcaacaca agtaaacccc    2820
agaaccacac ttgaagcaga tggttgtccc tacctatatg caattattca tgatagtaca    2880
acaggtacaa tctccggaga ttttatcttg gggtcaagct tgttggcatt aaggattttt    2940
gtggtatagg ttctaatccg ggtattgatg gttcccgctt gcttggagct atagcacaag    3000
gacctgtttg tgctgaagcc tcagatgtgt atagcccatg tatgatagct agcactcctc    3060
ctgctccatt ttcagacgtc acagcagtaa acttttgact taatcaacgg caaaataact    3120
cctgttggtg atgacaattg gaatacgcac atttataatc ctccaattat gaatgtcttg    3180
cgtactgctg cttggaaatc tggaactatt catgttcaac ttaatgttag gggtgctggt    3240
gtcaaaagag cagattggga tggtcaagtc tttgtttacc tgcgccagtc catgaaccct    3300
gaaagttatg atgcgcggac atttgtgatc tcacaacctg gttctgccat gttgaacttc    3360
tcttttgata tcatagggcc gaatagcgga tttgaatttg ccgaaagccc atgggccaat    3420
```

```
cagaccacct ggtatcttga atgtgttgct accaatccca gacaaataca gcaatttgag   3480
gtcaacatgc gcttcgatcc taatttcagg gttgccggca atatcctgat gcccccattt   3540
ccactgtcaa cggaaactcc accgttatta aagtttaggt ttcgggatat tgaacgctcc   3600
aagcgtagtg ttatggttgg acacactgct actgctgcag cgcctgcaaa acagctctta   3660
aactttgacc tacttaagtt agcaggtgac gttgagtcca accctgggcc cagtaaagga   3720
gaagaacttt tcactggagt tgtcccaatt cttgttgaat tagatggtga tgttaatggg   3780
cacaaatttt ctgtcagtgg agagggtgaa ggtgatgcaa catacggaaa acttacccct   3840
aaatttattt gcactactgg aaaactacct gttccatggc caacacttgt cactactttc   3900
tcttatggtg ttcaatgctt ttcaagatac ccagatcata tgaaacggca tgacttttc   3960 aagagtgcca tgcccgaagg ttatgtacag gaaagaacta tatttttcaa ggatgacggg   4020
aactacaaga cacgtgctga agtcaagttt gaaggtgata cccttgttaa tagaatcgag   4080
ttaaaaggta ttgattttaa agaagatgga acattcttg gacacaaatt ggaatacaac   4140
tataactcac acaatgtata catcatggca gacaaacaaa agaatggaat caaagttaac   4200
ttcaaaatta gacacaacat tgaagatgga agcgttcaac tagcagacca ttatcaacaa   4260
aatactccaa ttggcgatgg ccctgtcctt ttaccagaca accattacct gtccacacaa   4320
tctgcccttt cgaaagatcc caacgaaaag agagaccaca tggtccttct tgagtttgta   4380
acagctgctg ggattacaca tggcatggat gaactataca ataaaggcc tttaactctg   4440 gtttcattaa attttcttta gtttgaattt actgttattc ggtgtgcatt tctatgtttg   4500
gtgagcggtt ttctgtgctc agagtgtgtt tattttatgt aatttaattt ctttgtgagc   4560
tcctgtttag caggtcgtcc cttcagcaag gacacaaaaa gattttaatt ttattaaaaa   4620
aaaaaaaaaa aaagaccggg aattcgatat caagcttatc gacctgcaga tcgttcaaac   4680
atttggcaat aaagtttctt aagattgaat cctgttgccg tcttgcgat gattatcata   4740 taatttctgt tgaattacgt taagcatgta ataattaaca tgtaatgcat gacgttattt   4800
atgagatggg ttttttatgat tagagtcccg caattataca tttaatacgc gatagaaaac   4860
aaaatatagc gcgcaaacta ggataaatta tcgcgcgcgg tgtcatctat gttactagat   4920
ctctagagtc tcaagcttgg cgcgccagct gcattaatga atcggccaac gcgcggggag   4980
aggcggtttg cgtattgggc gctcttccgc ttcctcgctc actgactcgc tgcgctcggt   5040
cgttcggctg cggcgagcgg tatcagctca ctcaaaggcg gtaatacggt tatccacaga   5100 atcagggat aacgcaggaa agaacatgtg agcaaaaggc cagcaaaagg ccaggaaccg   5160
taaaaaggcc gcgttgctgg cgttttttcca taggctccgc ccccctgacg agcatcacaa   5220
aaatcgacgc tcaagtcaga ggtggcgaaa cccgacagga ctataaagat accaggcgtt   5280
tccccctgga agctccctcg tgcgctctcc tgttccgacc ctgccgctta ccggatacct   5340
gtccgccttt ctcccttcgg gaagcgtggc gctttctcat agctcacgct gtaggtatct   5400
cagttcggtg taggtcgttc gctccaagct gggctgtgtg cacgaacccc ccgttcagcc   5460
cgaccgctgc gccttatccg gtaactatcg tcttgagtcc aacccggtaa gacacgactt   5520
atcgccactg gcagcagcca ctggtaacag gattagcaga gcgaggtatg taggcggtgc   5580
tacagagttc ttgaagtggt ggcctaacta cggctacact agaagaacag tatttggtat   5640
ctgcgctctg ctgaagccag ttaccttcgg aaaagagtt ggtagctctt gatccggcaa   5700
acaaaccacc gctggtagcg gtggtttttt tgtttgcaag cagcagatta cgcgcagaaa   5760
aaaaggatct caagaagatc ctttgatctt ttctacgggg tctgacgctc agtggaacga   5820
```

```
aaactcacgt taagggattt tggttatgag attatcaaaa aggatcttca cctagatcct      5880
tttaaattaa aaatgaagtt ttaaatcaat ctaaagtata tatgagtaaa cttggtctga      5940
cagttaccaa tgcttaatca gtgaggcacc tatctcagcg atctgtctat ttcgttcatc      6000
catagttgcc tgactccccg tcgtgtagat aactacgata cgggagggct taccatctgg      6060
ccccagtgct gcaatgatac cgcgagaccc acgctcaccg gctccagatt tatcagcaat      6120
aaaccagcca gccggaaggg ccgagcgcag aagtggtcct gcaactttat ccgcctccat      6180
ccagtctatt aattgttgcc gggaagctag agtaagtagt tcgccagtta atagtttgcg      6240
caacgttgtt gccattgcta caggcatcgt ggtgtcacgc tcgtcgtttg gtatggcttc      6300
attcagctcc ggttcccaac gatcaaggcg agttacatga tcccccatgt tgtgcaaaaa      6360
agcggttagc tccttcggtc ctccgatcgt tgtcagaagt aagttggccg cagtgttatc      6420
actcatggtt atggcagcac tgcataattc tcttactgtc atgccatccg taagatgctt      6480
ttctgtgact ggtgagtact caaccaagtc attctgagaa tagtgtatgc ggcgaccgag      6540
ttgctcttgc ccggcgtcaa tacgggataa taccgcgcca catagcagaa ctttaaaagt      6600
gctcatcatt ggaaaacgtt cttcggggcg aaaactctca aggatcttac cgctgttgag      6660
atccagttcg atgtaaccca ctcgtgcacc caactgatct tcagcatctt ttactttcac      6720
cagcgtttct gggtgagcaa aaacaggaag gcaaaatgcc gcaaaaaagg gaataagggc      6780
gacacggaaa tgttgaatac tcatactctt cctttttcaa tattattgaa gcatttatca      6840
gggttattgt cttatgagcg gatacatatt tgaatgtatt tagaaaaata aacaaatagg      6900
ggttccgcgc acatttcccc gaaaagtgcc acctaaattg taagcgttaa tattttgtta      6960
aaattcgcgt taaattttg ttaaatcagc tcattttta accaataggc cgaaatcggc      7020
aaaatccctt ataaatcaaa agaatagacc gagatagggt tgagtgttgt tccagtttgg      7080
aacaagagtc cactattaaa gaacgtggac tccaacgtca aagggcgaaa aaccgtctat      7140
cagggcgatg gcccactacg tgaaccatca ccctaatcaa gttttttggg gtcgaggtgc      7200
cgtaaagcac taaatcggaa ccctaaaggg agcccccgat ttagagcttg acggggaaag      7260
ccggcgaacg tggcgagaaa ggaagggaag aaagcgaaag gagcgggcgc tagggcgctg      7320
gcaagtgtag cggtcacgct gcgcgtaacc accacacccg ccgcgcttaa tgcgccgcta      7380
cagggcgcgt cccattcgcc attcaggctg cgcaactgtt gggaagggcg atcggtgcgg      7440
gcctcttcgc tattacgcca gctggcgaaa ggggatgtg ctgcaaggcg attaagttgg      7500
gtaacgccag ggttttccca gtcacgacgt tgtaaaacga cggccagtga gtactttggc      7560
gtaatcatgg tcatagctgt ttcctgtgtg aaattgttat ccgctcacaa ttccacacaa      7620
catacgagcc ggaagcataa agtgtaaagc ctggggtgcc taatgagtga gctaactcac      7680
attaattgcg ttgcgctcac tgcccgcttt ccagtcggga aacctggcgc gc             7732
```

<210> SEQ ID NO 10
<211> LENGTH: 4173
<212> TYPE: DNA
<213> ORGANISM: Artificial sequence
<220> FEATURE:
<223> OTHER INFORMATION: Synthetic sequence: pM81-FSC-2

<400> SEQUENCE: 10

```
tattaaaatc ttaataggtt ttgataaaag cgaacgtggg gaaacccgaa ccaaaccttc        60
ttctaaactc tctctcatct ctcttaaagc aaacttctct cttgtctttc ttgcatgagc       120
gatcttcaac gttgtcagat cgtgcttcgg caccagtaca atgttttctt tcactgaagc       180
```

```
gaaatcaaag atctctttgt ggacacgtag tgcggcgcca ttaaataacg tgtacttgtc      240
ctattcttgt cggtgtggtc ttgggaaaag aaagcttgct ggaggctgct gttcagcccc      300
atacattact tgttacgatt ctgctgactt tcggcgggtg caatatctct acttctgctt      360
gacgaggtat tgttgcctgt acttctttct tcttcttctt gctgattggt tctataagaa      420
atctagtatt ttctttgaaa cagagttttc ccgtggtttt cgaacttgga gaaagattgt      480
taagcttctg tatattctgc ccaaattcgc gacgatcgta ctctcgaggc ctttaactct      540
ggtttcatta aattttcttt agtttgaatt tactgttatt cggtgtgcat ttctatgttt      600
ggtgagcggt tttctgtgct cagagtgtgt ttattttatg taatttaatt tctttgtgag      660
ctcctgttta gcaggtcgtc ccttcagcaa ggacacaaaa agattttaat tttattaaaa      720
aaaaaaaaaa aaaagaccgg gaattcgata tcaagcttat cgacctgcag atcgttcaaa      780
catttggcaa taaagtttct taagattgaa tcctgttgcc ggtcttgcga tgattatcat      840
ataatttctg ttgaattacg ttaagcatgt aataattaac atgtaatgca tgacgttatt      900
tatgagatgg gttttatga ttagagtccc gcaattatac atttaatacg cgatagaaaa      960
caaaatatag cgcgcaaact aggataaatt atcgcgcgcg tgtcatcta tgttactaga     1020 tctctagagt ctcaagcttg gcgcgccagc tgcattaatg aatcggccaa cgcgcgggga     1080
gaggcggttt gcgtattggg cgctcttccg cttcctcgct cactgactcg ctgcgctcgg     1140
tcgttcggct gcggcgagcg gtatcagctc actcaaaggc ggtaatacgg ttatccacag     1200
aatcagggga taacgcagga agaacatgt gagcaaaagg ccagcaaaag gccaggaacc     1260
gtaaaaaggc cgcgttgctg cgttttttcc ataggctccg ccccctgac gagcatcaca     1320 aaaatcgacg ctcaagtcag aggtggcgaa acccgacagg actataaaga taccaggcgt     1380
ttccccctgg aagctccctc gtgcgctctc ctgttccgac cctgccgctt accggatacc     1440
tgtccgcctt tctcccttcg ggaagcgtgg cgctttctca tagctcacgc tgtaggtatc     1500
tcagttcggt gtaggtcgtt cgctccaagc tgggctgtgt gcacgaaccc cccgttcagc     1560
ccgaccgctg cgccttatcc ggtaactatc gtcttgagtc aacccggta agacacgact     1620 tatcgccact ggcagcagcc actggtaaca ggattagcag agcgaggtat gtaggcggtg     1680
ctacagagtt cttgaagtgg tggcctaact acggctacac tagaagaaca gtatttggta     1740
tctgcgctct gctgaagcca gttaccttcg gaaaaagagt tggtagctct tgatccggca     1800
aacaaaccac cgctggtagc ggtggttttt ttgtttgcaa gcagcagatt acgcgcagaa     1860
aaaaaggatc tcaagaagat cctttgatct tttctacggg gtctgacgct cagtggaacg     1920
aaaactcacg ttaagggatt ttggttatga gattatcaaa aaggatcttc acctagatcc     1980
ttttaaatta aaaatgaagt tttaaatcaa tctaaagtat atatgagtaa acttggtctg     2040
acagttacca atgcttaatc agtgaggcac ctatctcagc gatctgtcta tttcgttcat     2100
ccatagttgc ctgactcccc gtcgtgtaga taactacgat acgggagggc ttaccatctg     2160
gccccagtgc tgcaatgata ccgcgagacc cacgctcacc ggctccagat ttatcagcaa     2220
taaaccagcc agccggaagg gccgagcgca gaagtggtcc tgcaacttta tccgcctcca     2280
tccagtctat taattgttgc cgggaagcta gagtaagtag ttcgccagtt aatagtttgc     2340
gcaacgttgt tgccattgct acaggcatcg tggtgtcacg ctcgtcgttt ggtatggctt     2400
cattcagctc cggttcccaa cgatcaaggc gagttacatg atccccatg ttgtgcaaaa     2460 aagcggttag ctccttcggt cctccgatcg ttgtcagaag taagttggcc gcagtgttat     2520
cactcatggt tatggcagca ctgcataatt ctcttactgt catgccatcc gtaagatgct     2580
```

-continued

```
tttctgtgac tggtgagtac tcaaccaagt cattctgaga atagtgtatg cggcgaccga    2640
gttgctcttg cccggcgtca atacgggata ataccgcgcc acatagcaga actttaaaag    2700
tgctcatcat tggaaaacgt tcttcggggc gaaaactctc aaggatctta ccgctgttga    2760
gatccagttc gatgtaaccc actcgtgcac ccaactgatc ttcagcatct tttactttca    2820
ccagcgtttc tgggtgagca aaaacaggaa ggcaaaatgc cgcaaaaaag gaataagggc    2880 gacacggaa atgttgaata ctcatactct ccttttttca atattattga agcatttatc    2940
agggttattg tcttatgagc ggatacatat ttgaatgtat ttagaaaaat aaacaaatag    3000
gggttccgcg cacatttccc cgaaaagtgc cacctaaatt gtaagcgtta atattttgtt    3060
aaaattcgcg ttaaattttt gttaaatcag ctcattttttt aaccaatagg ccgaaatcgg    3120
caaaatccct tataaatcaa agaatagac cgagataggg ttgagtgttg ttccagtttg    3180
gaacaagagt ccactattaa agaacgtgga ctccaacgtc aaagggcgaa aaaccgtcta    3240
tcagggcgat ggcccactac gtgaaccatc accctaatca agttttttgg ggtcgaggtg    3300
ccgtaaagca ctaaatcgga accctaaagg gagcccccga tttagagctt gacggggaaa    3360
gccggcgaac gtggcgagaa aggaagggaa gaaagcgaaa ggagcgggcg ctagggcgct    3420
ggcaagtgta gcggtcacgc tgcgcgtaac caccacaccc gccgcgctta atgcgccgct    3480
acagggcgcg tcccattcgc cattcaggct gcgcaactgt tgggaagggc gatcggtgcg    3540
ggcctcttcg ctattacgcc agctggcgaa aggggggatgt gctgcaaggc gattaagttg    3600
ggtaacgcca gggttttccc agtcacgacg ttgtaaaacg acggccagtg agtactttgg    3660
cgtaatcatg gtcatagctg tttcctgtgt gaaattgtta tccgctcaca attccacaca    3720
acatacgagc cggaagcata aagtgtaaag cctggggtgc ctaatgagtg agctaactca    3780
cattaattgc gttgcgctca ctgcccgctt tccagtcggg aaacctggcc gcttaattaa    3840
gaattcgagc tccaccgcgg aaacctcctc ggattccatt gcccagctat ctgtcacttt    3900
attgagaaga tagtggaaaa ggaaggtggc tcctacaaat gccatcattg cgataaagga    3960
aaggccatcg ttgaagatgc ctctgccgac agtggtccca agatggaccc cccacccacg    4020
aggagcatcg tggaaaaaga agacgttcca accacgtctt caaagcaagt ggattgatgt    4080
gatatctcca ctgacgtaag ggatgacgca caatcccact atccttcgca agacccttcc    4140
tctatataag gaagttcatt tcatttggag agg                                  4173
```

<210> SEQ ID NO 11
<211> LENGTH: 69
<212> TYPE: DNA
<213> ORGANISM: Artificial Sequence
<220> FEATURE:
<223> OTHER INFORMATION: Synthetic sequence: Polylinker
<220> FEATURE:
<221> NAME/KEY: CDS
<222> LOCATION: (3)..(68)

<400> SEQUENCE: 11

```
tc gcg acc ggt atg cat cac cat cac cat ccc ggg cat cac cat         47
   Ala Thr Gly Met His His His His His Pro Gly His His His
   1               5                   10                  15 cac cat cac tag ctc gag gcc t                                      69
His His His     Leu Glu Ala
```

<210> SEQ ID NO 12
<211> LENGTH: 18
<212> TYPE: PRT
<213> ORGANISM: Artificial Sequence
<220> FEATURE:

<223> OTHER INFORMATION: Synthetic sequence: Polylinker

<400> SEQUENCE: 12

Ala Thr Gly Met His His His His His His Pro Gly His His His
1               5                   10                  15

His His

<210> SEQ ID NO 13
<211> LENGTH: 69
<212> TYPE: DNA
<213> ORGANISM: Artificial Sequence
<220> FEATURE:
<223> OTHER INFORMATION: Synthetic sequence: Polylinker

<400> SEQUENCE: 13
aggcctcgag ctagtgatgg tgatggtgat gcccgggatg atggtgatgg tgatgcatac    60
cggtcgcga                                                            69

<210> SEQ ID NO 14
<211> LENGTH: 25
<212> TYPE: DNA
<213> ORGANISM: Artificial sequence
<220> FEATURE:
<223> OTHER INFORMATION: Synthetic sequence: Oligonucleotide pBD-LB-F

<400> SEQUENCE: 14
gccactcagc ttcctcagcg ctttt                                          25

<210> SEQ ID NO 15
<211> LENGTH: 39
<212> TYPE: DNA
<213> ORGANISM: Artificial sequence
<220> FEATURE:
<223> OTHER INFORMATION: Synthetic sequence: Oligonucleotide pBD-RB-
    ApaI-R

<400> SEQUENCE: 15
tattagggcc cccggcgcca gatctgggga accctgtgg                           39

<210> SEQ ID NO 16
<211> LENGTH: 42
<212> TYPE: DNA
<213> ORGANISM: Artificial sequence
<220> FEATURE:
<223> OTHER INFORMATION: Synthetic sequence: Oligonucleotide pBD-ColEI-
    ApaI-F

<400> SEQUENCE: 16
gacttagggc ccgtccattt ccgcgcagac gatgacgtca ct                       42

<210> SEQ ID NO 17
<211> LENGTH: 45
<212> TYPE: DNA
<213> ORGANISM: Artificial sequence
<220> FEATURE:
<223> OTHER INFORMATION: Synthetic sequence: Oligonucleotide pBD-TrfA-
    SpeI-R

<400> SEQUENCE: 17
gcattaacta gtcgctggct gctgaacccc cagccggaac tgacc                    45

<210> SEQ ID NO 18
<211> LENGTH: 33
<212> TYPE: DNA
<213> ORGANISM: Artificial sequence
<220> FEATURE:

```
<223> OTHER INFORMATION: Synthetic sequence: Oligonucleotide pBD-oriV-
      SpeI-F

<400> SEQUENCE: 18
gtagcactag tgtacatcac cgacgagcaa ggc                              33

<210> SEQ ID NO 19
<211> LENGTH: 38
<212> TYPE: DNA
<213> ORGANISM: Artificial sequence
<220> FEATURE:
<223> OTHER INFORMATION: Synthetic sequence: Oligonucleotide pBD-oriV-
      AhdI-R

<400> SEQUENCE: 19
cagtagacag gctgtctcgc ggccgagggg cgcagccc                         38

<210> SEQ ID NO 20
<211> LENGTH: 77
<212> TYPE: DNA
<213> ORGANISM: Artificial sequence
<220> FEATURE:
<223> OTHER INFORMATION: Synthetic sequence: Oligonucleotide pMini>pMicr
      oBIN-F2

<400> SEQUENCE: 20
ggccggccac gcgttatctg cagagcgatc gcgaattgtg agcggataac aatttcacac  60
aggaaacagc tatgacc                                                77

<210> SEQ ID NO 21
<211> LENGTH: 77
<212> TYPE: DNA
<213> ORGANISM: Artificial sequence
<220> FEATURE:
<223> OTHER INFORMATION: Synthetic sequence: Oligonucleotide pMini>pMicr
      oBIN-R

<400> SEQUENCE: 21
gcgatcgctc tgcagataac gcgtggccgg ccctcactgg tgaaagaaa aaccacccca   60 gtacattaaa aacgtcc                                                77

<210> SEQ ID NO 22
<211> LENGTH: 36
<212> TYPE: DNA
<213> ORGANISM: Artificial sequence
<220> FEATURE:
<223> OTHER INFORMATION: Synthetic sequence: Oligonucleotide 35SP19-
      PacI-F

<400> SEQUENCE: 22
ttaattaaga attcgagctc ggtaccccccc tactcc                          36

<210> SEQ ID NO 23
<211> LENGTH: 40
<212> TYPE: DNA
<213> ORGANISM: Artificial sequence
<220> FEATURE:
<223> OTHER INFORMATION: Synthetic sequence: Oligonucleotide 35SP19-
      AscI-R

<400> SEQUENCE: 23
ggcgcgccat cttttatctt tagagttaag aactctttcg                       40

<210> SEQ ID NO 24
<211> LENGTH: 29
<212> TYPE: DNA
```

<213> ORGANISM: Artificial sequence
<220> FEATURE:
<223> OTHER INFORMATION: Synthetic sequence: Oligonucleotide 35SP19-
      FseI-F

<400> SEQUENCE: 24
ggccggccga attcgagctc ggtaccccc                                         29

<210> SEQ ID NO 25
<211> LENGTH: 30
<212> TYPE: DNA
<213> ORGANISM: Artificial sequence
<220> FEATURE:
<223> OTHER INFORMATION: Synthetic sequence: Oligonucleotide 35SP19-
      FseI-R

<400> SEQUENCE: 25
ggccggccat cttttatctt tagagttaag                                        30

<210> SEQ ID NO 26
<211> LENGTH: 40
<212> TYPE: DNA
<213> ORGANISM: Artificial sequence
<220> FEATURE:
<223> OTHER INFORMATION: Synthetic sequence: Oligonucleotide pBD-NPTII-
      FseI-F

<400> SEQUENCE: 26
ggccggccta cagtatgagc ggagaattaa gggagtcacg                             40

<210> SEQ ID NO 27
<211> LENGTH: 44
<212> TYPE: DNA
<213> ORGANISM: Artificial sequence
<220> FEATURE:
<223> OTHER INFORMATION: Synthetic sequence: Oligonucleotide pBD-NPTII-
      FseI-R

<400> SEQUENCE: 27
ggccggccta cagtcccgat ctagtaacat agatgacacc gcgc                        44

<210> SEQ ID NO 28
<211> LENGTH: 35
<212> TYPE: DNA
<213> ORGANISM: Artificial sequence
<220> FEATURE:
<223> OTHER INFORMATION: Synthetic sequence: Oligonucleotide P19-R43W-F

<400> SEQUENCE: 28
cgagttggac tgagtggtgg ctacataacg atgag                                  35

<210> SEQ ID NO 29
<211> LENGTH: 35
<212> TYPE: DNA
<213> ORGANISM: Artificial sequence
<220> FEATURE:
<223> OTHER INFORMATION: Synthetic sequence: Oligonucleotide P19-R43W-R

<400> SEQUENCE: 29
ctcatcgtta tgtagccacc actcagtcca actcg                                  35

<210> SEQ ID NO 30
<211> LENGTH: 33
<212> TYPE: DNA
<213> ORGANISM: Artificial sequence
<220> FEATURE:
<223> OTHER INFORMATION: Synthetic sequence: Oligonucleotide P19-
      deltaNruI-F

```
<400> SEQUENCE: 30
ccgtttctgg agggtctcga actcttcagc atc                              33

<210> SEQ ID NO 31
<211> LENGTH: 33
<212> TYPE: DNA
<213> ORGANISM: Artificial sequence
<220> FEATURE:
<223> OTHER INFORMATION: Synthetic sequence: Oligonucleotide P19-
      deltaNruI-R

<400> SEQUENCE: 31
gatgctgaag agttcgagac cctccagaaa cgg                              33

<210> SEQ ID NO 32
<211> LENGTH: 57
<212> TYPE: DNA
<213> ORGANISM: Artificial sequence
<220> FEATURE:
<223> OTHER INFORMATION: Synthetic sequence: Oligonucleotide POW-F

<400> SEQUENCE: 32
cgaccggtat gcatcaccat caccatcatc ccgggcatca ccatcaccat cactagc    57

<210> SEQ ID NO 33
<211> LENGTH: 62
<212> TYPE: DNA
<213> ORGANISM: Artificial sequence
<220> FEATURE:
<223> OTHER INFORMATION: Synthetic sequence: Oligonucleotide POW-R

<400> SEQUENCE: 33
tcgagctagt gatggtgatg gtgatgcccg ggatgatggt gatggtgatg cataccggtt 60
cg                                                                62

<210> SEQ ID NO 34
<211> LENGTH: 33
<212> TYPE: DNA
<213> ORGANISM: Artificial sequence
<220> FEATURE:
<223> OTHER INFORMATION: Synthetic sequence: Oligonucleotide GFP-AgeI-F

<400> SEQUENCE: 34
atcggaccgg tatgactagc aaaggagaag aac                              33

<210> SEQ ID NO 35
<211> LENGTH: 38
<212> TYPE: DNA
<213> ORGANISM: Artificial sequence
<220> FEATURE:
<223> OTHER INFORMATION: Synthetic sequence: Oligonucleotide GFP-XmaI-F

<400> SEQUENCE: 35
atccgacccg ggactagcaa aggagaagaa cttttcac                         38

<210> SEQ ID NO 36
<211> LENGTH: 33
<212> TYPE: DNA
<213> ORGANISM: Artificial sequence
<220> FEATURE:
<223> OTHER INFORMATION: Synthetic sequence: Oligonucleotide GFP-XmaI-R

<400> SEQUENCE: 36
atccgacccg ggtttgtata gttcatccat gcc                              33
```

```
<210> SEQ ID NO 37
<211> LENGTH: 35
<212> TYPE: DNA
<213> ORGANISM: Artificial sequence
<220> FEATURE:
<223> OTHER INFORMATION: Synthetic sequence: Oligonucleotide GFP-XhoI-R

<400> SEQUENCE: 37
cgatcctcga gttatttgta tagttcatcc atgcc                              35
```